(12) United States Patent
Gordeev et al.

(10) Patent No.: US 8,530,452 B2
(45) Date of Patent: Sep. 10, 2013

(54) TRICYCLIC BORON COMPOUNDS FOR ANTIMICROBIAL THERAPY

(71) Applicant: Micurx Pharmaceuticals, Inc., George Town (KY)

(72) Inventors: Mikhail Fedorovich Gordeev, Castro Valley, CA (US); Jinqian Liu, Fremont, CA (US); Zhengyu Yuan, Palo Alto, CA (US); Xinghai Wang, Shanghai (CN)

(73) Assignee: MicuRx Pharmaceuticals, Inc., George Town (KY)

( * ) Notice: Subject to any disclaimer, the term of this patent is extended or adjusted under 35 U.S.C. 154(b) by 0 days.

(21) Appl. No.: 13/722,912

(22) Filed: Dec. 20, 2012

(65) Prior Publication Data

US 2013/0165411 A1   Jun. 27, 2013

Related U.S. Application Data

(60) Provisional application No. 61/579,271, filed on Dec. 22, 2011.

(51) Int. Cl.
*A61K 31/69* (2006.01)

(52) U.S. Cl.
USPC .............................. 514/64; 549/213

(58) Field of Classification Search
USPC .......................... 514/64; 549/213
See application file for complete search history.

(56) References Cited

U.S. PATENT DOCUMENTS

| | | | |
|---|---|---|---|
| 2009/0227541 | A1 | 9/2009 | Baker et al. |
| 2009/0239824 | A1 | 9/2009 | Lee et al. |

FOREIGN PATENT DOCUMENTS

| | | | |
|---|---|---|---|
| WO | WO 2005/013892 | A2 | 2/2005 |
| WO | WO 2007/131072 | A2 | 11/2007 |
| WO | WO 2008/157726 | A1 | 12/2008 |
| WO | WO 2009/140309 | A2 | 11/2009 |
| WO | WO 2010/022337 | A2 | 2/2010 |
| WO | WO 2010/080558 | A1 | 7/2010 |
| WO | WO 2011/017125 | A1 | 2/2011 |
| WO | WO 2011/127143 | A1 | 10/2011 |
| WO | WO 2012/033858 | A2 | 3/2012 |

OTHER PUBLICATIONS

International Search Report and Written Opinion in PT/IB2012/002880, mailed Apr. 15, 2013, 15 pages.
Ye et al., "Convenient and versatile synthesis of formyl-substituted benzoxaboroles", *Tetrahedron* (2009) 65:8738-8744.
Bakalarz-Jeziorna et al., "Synthesis of multifunctionalized phosphonic acid esters via opening of oxiranes and azetidinium salts with phosphoryl-substituted carbanions", *J Chem Soc., Perkin Trans 1* (2001) 1:1086-1090.
Li et al., "Synthesis and antibacterial evaluation of a novel tricyclic oxaborole-fused fluoroquinolone", *Bioorg Med Chem Lett* (2013) 23:963-966.
Meanwell, "Synopsis of some recent tactical application of bioisosteres in drug design", *J Med Chem* (2011) 54:2529-2591.
Zane et al., "Safety, tolerability, and pharmacokinetics of a novel Gram-negative antimicrobial", GSK2251052, Healthy Subjects, 21st European Congress of Clinical Microbiology and Infectious Diseases, 2011, Milan, Italy, 1 page.

*Primary Examiner* — Samantha Shterengarts
(74) *Attorney, Agent, or Firm* — Squire Sanders (US) LLP

(57) ABSTRACT

Provided herein are antimicrobial tricyclic boron compounds of the following formula I:

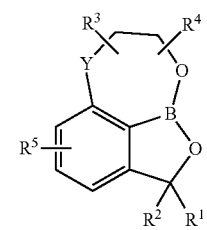

or pharmaceutically acceptable salts, complexes, or tautomers thereof that are antibacterial agents, pharmaceutical compositions containing them, methods for their use, and methods for preparing these compounds.

14 Claims, 1 Drawing Sheet

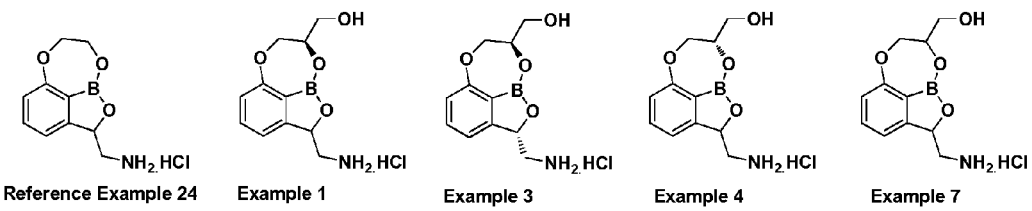
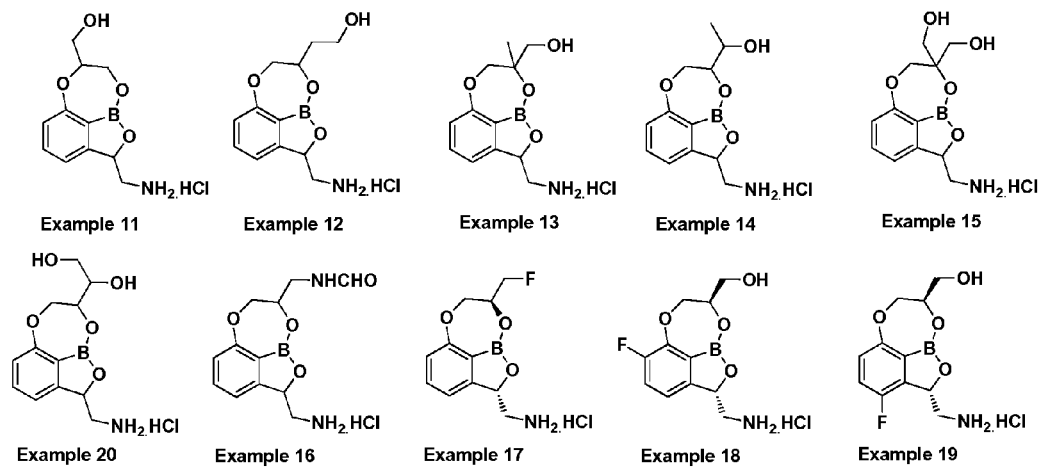

TRICYCLIC BORON COMPOUNDS FOR ANTIMICROBIAL THERAPY

CROSS-REFERENCE TO RELATED APPLICATION

This application claims the benefit under 35 U.S.C. §119 of, and priority to, provisional application No. 61/579,271 entitled "Novel Tricyclic Boron Compounds for Antimicrobial Therapy", filed Dec. 22, 2011, the content of which is hereby incorporated by reference in its entirety.

FIELD

Provided herein are antimicrobial boron-organic compounds, pharmaceutical compositions thereof, methods for their use, and methods for preparing of the same. The compounds provided herein possess useful activity against bacterial species.

BACKGROUND

Owing to an increasing bacterial resistance, novel classes of antibacterial compounds are needed for the treatment of microbial infections. Agents acting via a new mechanism of action are desired to avoid undesired cross-resistance with existing drugs. Said agents are required to possess useful activity against key mammalian pathogens, including Gram-negative bacteria, including *Pseudomonas aeruginosa, Acinetobacter baumannii, Escherichia coli,* and *Klebsiela pneumoniae,* as well as key Gram-positive bacteria such as multidrug-resistant staphylococci and streptococci, certain anaerobe pathogens such as *bacteroides* and *clostridia* species, such as *Clostridium difficile,* and acid-fast microorganisms, including *Mycobacterium tuberculosis* and *Mycobacterium avium.* These agents are also needed for treatment of serious parasitic infections, such as Trypanosomanaiasis.

Several antibacterial boron-organic compounds have been previously described in the publications PCT WO 2005/013892, PCT WO 2007/131072, PCT WO 2008/157726, US 2009/0227541, US 2009/0239824, WO 2009/140309, PCT WO 2010/080558, PCT WO 2011/017125, and PCT WO 2012/033858. To date, no compound of this class has been approved for anti-infective therapy in human.

None of the aforementioned specifically contemplates any compound provided herein, its combination therapy, and/or its composition.

SUMMARY

Provided herein are pharmaceutical compounds with high antibacterial activity, including activity against Gram-negative and Gram-positive microorganisms, as well as against mycobacteria. These compounds are particularly active against Gram-negative bacteria such as *Pseudomonas aeruginosa, Acinetobacter baumannii, Escherichia coli,* and *Klebsiela pneumoniae.* Said compounds are also active against yeast and fungi microorganism, such as *Candida albicans* or *Cryptococcus neoformans.* Certain compounds provided herein are also active against parasitic protozoan pathogens, such as *Trypanosoma brucei gambiense* or *Trypanosoma brucei rhodesiens.*

Provided herein are compounds of the following formula A or B:

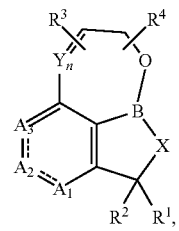

A

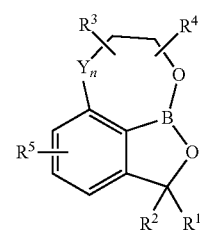

B or a pharmaceutically acceptable salt, complex, or tautomer thereof, wherein:

$R^1$ and $R^2$ are independently H, F, $C_{1-6}$alkyl, $C_{1-6}$heteroalkyl, $C_{3-6}$cycloalkyl, $C_{1-6}$(amino)alkyl, aminomethyl, hydroxymethyl, $C_{1-6}$alkylNH$_2$, $C_{1-6}$alkylOH, $C_{1-6}$alkylNR$_2$, OC$_{1-6}$alkylNH$_2$, $C_{1-6}$alkylCH=NOR, $C_{1-6}$alkyl(imidazole), $C_{1-6}$alkyl(guanidine), $C_{1-6}$alkylC(=NH)NH$_2$, $C_{1-6}$alkylC(=NOH)NH$_2$; and wherein R is H, $C_{1-6}$alkyl, $C_{1-6}$heteroalkyl, $C_{1-6}$alkoxy, $C_{1-6}$alkylS(O)$_m$; wherein m is 0, 1, or 2; and wherein X is O, S, or NR', wherein R' is C(=O)$C_{1-6}$alkyl, C(=O)OC$_{1-6}$alkyl, C(=O)OC$_{1-6}$(hydroxyl)alkyl, C(=O)NH$_2$, C(=O)NHC$_{1-6}$alkyl, SO$_2$Ar, or SO$_2$C$_{1-6}$alkyl; and wherein $R^3$ and $R^4$ are independently a single substituent or multiple substituents independently selected from H, halo, CN, $C_{1-6}$alkyl, $C_{1-6}$alkylamino, $C_{1-6}$alkoxy, $C_{2-6}$alkenyl, $C_{1-6}$heteroalkyl, $C_{1-6}$haloalkyl, $C_{1-6}$(hydroxy)alkyl, $C_{1-6}$(hydroxy)alkenyl, $C_{1-6}$(amino)alkyl, OC(=O)NH$_2$, OC(=O)NHC$_{1-6}$alkyl; or $R^3$ and $R^4$ taken together form $C_{3-6}$cycloalkyl group; and wherein $R^5$ is H, halo, CN, OH, NH$_2$, $C_{1-6}$alkyl, $C_{1-6}$alkoxy, $C_{1-6}$alkylamino, $C_{1-6}$(hydroxy)alkyl, $C_{1-6}$(amino)alkyl, C(=O)NHC$_{1-6}$alkyl, C(=O)NH-aryl; or NHC(=O)OC$_{1-6}$alkyl group; and wherein Y is O, CH, CH$_2$, CF, CHF, CF$_2$, or S(O)$_m$; wherein m is 0, 1, or 2; and wherein $A_1, A_2,$ and $A_3$ are independently N, O, S, NH, N—$C_{1-6}$alkyl, N—(CO)$C_{1-6}$alkoxy, N—SO$_2$C$_{1-6}$alkyl, or C—$R^5$; wherein $R^5$ for each of $A_1$-$A_3$ is independently selected from H, halo, CN, OH, NH$_2$, $C_{1-6}$alkyl, $C_{1-6}$alkoxy, $C_{1-6}$alkylamino, $C_{2-6}$alkenyl, $C_{1-6}$heteroalkyl, $C_{1-6}$(hydroxy)alkyl, $C_{1-6}$(amino)alkyl, $C_{1-6}$alkylCH=NOR, $C_{1-6}$alkylCH=NOH, $C_{1-6}$alkylC(=NOH)NH$_2$, $C_{1-6}$alkylC(=NH)NH$_2$, or $C_{1-6}$alkyl(guanidine), C(=O)NH$_2$, C(=O)NHC$_{1-6}$alkyl, C(=O)NH-aryl; NHC(=O)OC$_{1-6}$alkyl, pyridyl, triazolyl, oxazolyl, pyrazolyl, imidazolyl, or aryl group; and wherein each bond with a dotted line is independently either a single bond or a double bond; and wherein n is 0 or 1.

The alkyl, alkenyl, or cycloalkyl groups at each occurrence above independently are optionally substituted with one, two, or three substituents selected from the group consisting of halo, aryl, Het$^1$, and Het$^2$. Het$^1$ at each occurrence is independently a C-linked 5- or 6-membered heterocyclic ring having 1 to 4 heteroatoms selected from the group consisting of oxygen, nitrogen, and sulfur within the ring. Het$^2$ at each occurrence is independently a N-linked 5 or 6 membered heterocyclic ring having 1 to 4 nitrogen and optionally having one oxygen or sulfur within the ring.

In one embodiment, provided is a compound of formula A or B excluding generally class-related specific examples described in publications PCT WO 2008/157726, US 2009/0227541, and PCT WO 2009/140309.

In another embodiment, provided are compounds of formula A or B and with a proviso that when X is O; and wherein $R^1$, $R^3$, and $R^4$ are all H; and wherein $R^2$ is $CH_2NH_2$; and wherein $A_1$, $A_2$, and $A_3$ are all CH; and wherein bonds with dotted lines connecting $A_1$-$A_3$ comprise a benzene aromatic system; and wherein the bond with a dotted line connected to the group Y is a single bond; and wherein n is 1; then Y is other than O.

Also provided herein are compounds of the following formula I:

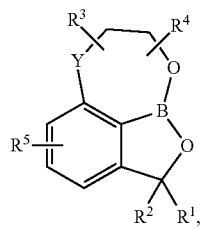

or a pharmaceutically acceptable salt, complex, or tautomer thereof, wherein:

$R^1$ and $R^2$ are independently H, F, $C_{1-6}$alkyl, $C_{1-6}$(amino)alkyl, aminomethyl, or $C_{1-6}$alkyl$NH_2$; and wherein $R^3$ and $R^4$ are independently a single substituent or multiple substituents independently selected from H, halo, CN, $C_{1-6}$alkyl, $C_{1-6}$(hydroxy)alkyl, $C_{1-6}$alkylamino, $C_{1-6}$alkoxy, $C_{1-6}$heteroalkyl, $C_{1-6}$haloalkyl, or $C_{1-6}$(amino)alkyl; and wherein Y is O, S, $CH_2$, CHF, or $CF_2$; and wherein $R^5$ is H, halo, CN, OH, or $NH_2$.

In one preferred embodiment, $R^1$ in a compound of formula I is H, and the chiral group $CHR^2$ has (S)-configuration of the chiral center.

In one aspect, provided is a compound of formula I and with a proviso that when $R^1$, $R^3$, $R^4$, and $R^5$ are all H; and wherein $R^2$ is $CH_2NH_2$; then Y is other than O. Further provided herein are compounds of formula I wherein $R^1$, $R^3$, $R^4$, and $R^5$ are all H; wherein $R^2$ is $CH_2NH_2$; and wherein Y is S, $CH_2$, CHF, or $CF_2$. Further provided herein are compounds of formula I wherein $R^1$, $R^3$, $R^4$, and $R^5$ are all H; wherein $R^2$ is $CH_2NH_2$; wherein Y is O; and wherein at least one of $R^3$ and $R^4$ is other than H.

In a preferred aspect, provided is a compound of formula I and excluding generally related specific example(s) described in publications 2008/157726, US 2009/0227541, and PCT WO 2009/140309. In certain embodiments, provided herein are compounds of formula I other than the following:

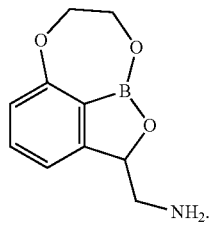 [SMILES: NCC1OB2OCCOc3cccc1c32]

In additional preferred aspect, provided herein are compounds of formula I wherein $R^1$ is H; and wherein the chiral group $CR^1R^2$ has (S)-configuration.

In one preferred aspect, provided is a compound of formula I wherein $R^1$, $R^3$, and $R^5$ are all H; $R^2$ is $CH_2NH_2$, and $R^4$ is $CH_2OH$ group attached to the carbon atom of the ring fragment CH—O—B.

In yet another preferred aspect, provided is a compound of formula I wherein $R^1$, $R^3$, and $R^5$ are all H; $R^2$ is $CH_2NH_2$, and $R^4$ is $CH_2OH$ group attached to the carbon atom of the ring fragment CH—O—B, and wherein the resulted chiral group $CHR^4$ has (R)-configuration It is understood that any salts, solvates and coordination compounds, complexes, tautomers, ring-opened forms, and prodrugs of said compounds of formula I are also within the scope of the compounds provided herein.

In another aspect, provided herein are pharmaceutical compositions comprising a compound of formula I, or a pharmaceutically acceptable salt thereof, and a pharmaceutically acceptable carrier.

In an additional aspect, provided herein are methods for treating Gram-negative or Gram-positive microbial infections in humans or other warm-blooded animals by administering to the subject in need a therapeutically effective amount of a compound of formula I or a pharmaceutically acceptable salt thereof. The compound of formula I may be administered orally, parenterally, transdermally, topically, rectally, or intranasally in a pharmaceutical composition.

In another aspect, provided herein are compositions and methods for the treatment of microbial infections caused by microorganisms selected from *Pseudomonas aeruginosa*, *Acinetobacter baumannii*, *Escherichia coli*, or *Klebsiela pneumoniae*.

In additional aspect, provided herein is a method for the treatment of a skin, soft tissue, respiratory, or an eye infection.

In yet another aspect, provided herein are intermediates and processes for preparing compounds of formula I.

BRIEF DESCRIPTION OF THE FIGURE

FIG. 1. Tricyclic boron compounds possessing and lacking therapeutic activity (potency expressed in MIC) against Gram-negative bacterial pathogen *A. baumannii*.

DETAILED DESCRIPTION OF THE DISCLOSURE

Unless otherwise stated, the following terms used in the specification and Claims have the meanings given below:

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The terms alkyl, alkenyl, etc. refer to both straight and branched groups, but reference to an individual radical such as "propyl" embraces only the straight chain radical, a branched chain isomer such as "isopropyl" being specifically referred to. The alkyl, alkenyl, etc. group may be optionally substituted with one, two, or three substituents selected from the group consisting of halo, aryl, Het$^1$, or Het$^2$. Representative examples include, but are not limited to, difluoromethyl, 2-fluoroethyl, trifluoroethyl. —CH CH-aryl, —CH CH-Het$^1$, —CH$_2$-phenyl, and the like.

The term "cycloalkyl" means a cyclic saturated monovalent hydrocarbon group of three to six carbon atoms, e.g., cyclopropyl, cyclohexyl, and the like. The cycloalkyl group may be optionally substituted with one, two, or three substituents selected from the group consisting of halo, aryl, Het$^1$, or Het$^2$.

The term "heteroalkyl" means an alkyl or cycloalkyl group, as defined above, having a substituent containing a heteroatom selected from N, O, or S(O)$_n$, where n is an integer from 0 to 2, including, hydroxy (OH), C$_{1-4}$alkoxy, amino, thio (—SH), and the like. Representative substituents include —NR$_a$R$_b$, —OR$_a$, or —S(O)$_n$R$_c$, wherein R$_a$ is hydrogen, C$_{1-4}$alkyl, C$_{3-6}$cycloalkyl, optionally substituted aryl, optionally substituted heterocyclic, or —COR (where R is C$_{1-4}$alkyl); R$_b$ is hydrogen, C$_{1-4}$alkyl, —SO$_2$R (where R is C$_{1-4}$alkyl or C$_{1-4}$hydroxyalkyl), —SO$_2$NRR' (where R and R' are independently of each other hydrogen or C$_{1-4}$alkyl), —CONR'R" (where R' and R" are independently of each other hydrogen or C$_{1-4}$alkyl); n is an integer from 0 to 2; and R$_c$ is hydrogen, C$_{1-4}$alkyl, C$_{3-6}$cycloalkyl, optionally substituted aryl, or NR$_a$R$_b$ where R$_a$ and R$_b$ are as defined above. Representative examples include, but are not limited to 2-methoxyethyl (—CH$_2$CH$_2$OCH$_3$), 2-hydroxyethyl (—CH$_2$CH$_2$OH), hydroxymethyl (—CH$_2$OH), 2-aminoethyl (—CH$_2$CH$_2$NH$_2$), 2-dimethylaminoethyl (—CH$_2$CH$_2$NHCH$_3$), benzyloxymethyl, thiophen-2-ylthiomethyl, and the like.

The term "halo" refers to fluoro (F), chloro (Cl), bromo (Br), or iodo (I).

The term aryl refers to phenyl, biphenyl, or naphthyl, optionally substituted with 1 to 3 substituents independently selected from halo, —C$_{1-4}$alkyl, —OH, —OC$_{1-4}$alkyl, —S(O)$_n$C$_{1-4}$alkyl wherein n is 0, 1, or 2, —C$_{1-4}$alkylNH$_2$, —NHC$_{1-4}$alkyl, —C(O)H, or —CN—OR$_d$ wherein R$_d$ is hydrogen or —C$_{1-4}$alkyl.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds may possess one or more asymmetric centers; such compounds can therefore be produced as individual (R)- or (S)-stereoisomers or as mixtures thereof. Unless indicated otherwise, the description or naming of a particular compound in the specification and Claims is intended to include both individual enantiomers and mixtures, racemic or otherwise, thereof. The methods for the determination of stereochemistry and the separation of stereoisomers are well-known in the art (see discussion in Chapter 4 of *Advanced Organic Chemistry*, 4th edition J. March, John Wiley and Sons, New York, 1992).

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and Claims includes both one and more than one such carrier.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "complex" means a composition comprising a compound provided herein and an additional other ingredient(s) that may be bound or coordinated to said compound in a way of a solvate (such as a hydrate formed with water), and/or by forming at least one coordination or ionic bond between the compound and the complexing ingredient(s). Thus, the boron atom can change its coordination number (or valency) from three (in a non-complexed compound) to four (in its complex) by accepting additional electron density from a donor atom of the complexing ingredient, as observed for trigonal (tri-valent) boron compounds often existing in a complexed tetragonal form (as described by Hall in *Boronic Acids: Preparation, Applications in Organic Syntheses and Medicine*. Ed. Dennis G. Hall, Wiley-VCH Verlag GmbH & Co., 2005, pp. 1-26). Two examples of such complex compounds that may be formed by an exemplary compound provided herein and a nitrogen (amine) or oxygen (water, alcohol or ether) compound is illustrated below.

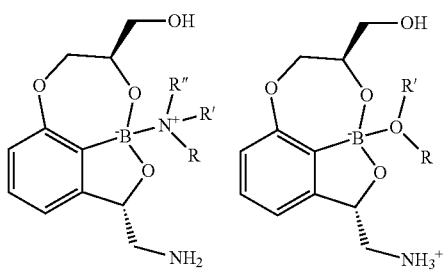

The complexing ingredients (such as ingredients R(R') NR" or ROR' in exemplary structures above) may be used to improve certain useful physico-chemical and/or biological properties of the compounds provided herein, including but not limited to solubility, stability, pharmacokinetics, or antimicrobial activity and antibacterial spectrum. For example, a complex of the compound provided herein with an amine-type antimicrobial agent such as aminoglycoside, colistin, and/or polymixin may be used to improve the therapeutic effect in the resulted complex, such as antibacterial effect on resistant pathogens not sufficiently eradicated by each of the complexed component alone.

The term "tautomers" means two or more forms or isomers of an organic compound that could be interconverted into each other via a common chemical reaction called tautomerization, generally analogous to that described by Smith et al., in *Advanced Organic Chemistry*. 2001, 5th Ed. NY: Wiley Interscience, pp. 1218-1223. The concept of tautomerizations is called tautomerism. The tautomerism may be accompanied by a change from a ring structure to an open structure, as observed, for example, for interconversion between the cyclic pyran form and the open chain form of glucose via formation and breaking of a C—O bond. The degree of tautomerism is often affected by a solvent effect, such as a hydration with water, and the media acidity. A related process concerning cyclic boron compounds may involve formation and breaking of a B—O bond as exemplified below:

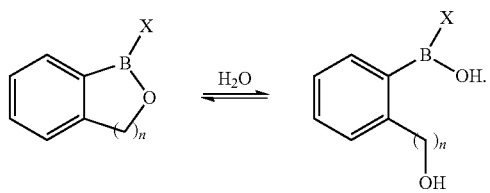

Any ring-opened forms of the tricyclic boron compounds provided herein, including any hydrated (water-added) forms are treated herein as "tautomers" and are within the scope of this application. In general, a material comprised of tautomers is commonly treated as a single chemical entity, such as acetone that exists in two interchangeable forms due to keto-enol tautomerization.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Leaving group" has the meaning conventionally associated with it in synthetic organic chemistry, i.e., an atom or group capable of being displaced by a nucleophile and includes halogen, $C_{1-4}$alkylsulfonyloxy, ester, or amino such as chloro, bromo, iodo, mesyloxy, tosyloxy, trifluorosulfonyloxy, methoxy, N,O-dimethylhydroxyl-amino, and the like.

"Prodrug" means any compound which releases an active parent drug according to a compound provided herein in vivo when such prodrug is administered to a mammalian subject. Prodrugs of a compound provided herein are prepared by modifying functional groups present in a compound provided herein in such a way that the modifications may be cleaved in vivo to release the parent compound. Prodrugs include compounds provided herein wherein a hydroxy, sulfhydryl, amido or amino group in the compound is bonded to any group that may be cleaved in vivo to regenerate the free hydroxyl, amido, amino, or sulfhydryl group, respectively. Examples of prodrugs include, but are not limited to esters (e.g., acetate, propionate, butyrate, formate, benzoate, phosphate or phosphonate derivatives), carbamates (e.g., N,N-dimethylaminocarbonyl) of hydroxy functional groups in compounds provided herein, and the like. It is understood that prodrugs could be utilized, for example, to improve oral bioavailability of a drug, direct the drug to a particular target organ, enhance stability for a particular administration route (e.g., aerosol), or improve its solubility, as reviewed, for example, by Ettmayer et al. in *J. Med. Chem.* 2004, vol. 47, pp 2393-2404.

The term "mammal" refers to all mammals including humans, livestock, and companion animals.

The compounds provided herein are generally named according to the IUPAC or CAS nomenclature system. Abbreviations which are well known to one of ordinary skill in the art may be used (e.g. "Ar" for aryl, "Ph" for phenyl, "Me" for methyl, "Et" for ethyl, "h" for hour or hours and "rt" or "r.t." for room temperature).

Illustrative Embodiments

Within the broadest definition provided herein, certain compounds of the compounds of formula I may be preferred. Specific and preferred values listed below for radicals, substituents, and ranges, are for illustration only; they do not exclude other defined values or other values within defined ranges for the radicals and substituents.

In some preferred compounds provided herein $C_{1-4}$alkyl can be methyl, ethyl, propyl, isopropyl, butyl, iso-butyl, sec-butyl, and isomeric forms thereof.

In some preferred compounds provided herein $C_{2-4}$alkenyl can be vinyl, propenyl, allyl, butenyl, and isomeric forms thereof (including cis and trans isomers).

In some preferred compounds provided herein, $R^1$ is H, and the chiral group $CHR^2$ has (S)-configuration.

In some preferred compounds, $R^1$ is H, and the chiral group $CR^1R^2$ has (S)-configuration.

In some preferred compounds provided herein, $R^1$, $R^3$, and $R^5$ are all H, $R^2$ is $CH_2NH_2$, and $R^4$ is $CH_2OH$ group attached to the carbon atom of the ring fragment CH—O—B.

In other preferred compounds provided herein, $R^1$, $R^3$, and $R^5$ are all H; $R^2$ is $CH_2NH_2$, and $R^4$ is $CH_2OH$ group attached to the carbon atom of the ring fragment CH—O—B, and the resulted chiral group $CHR^4$ has (R)-configuration.

In some preferred compounds provided herein $C_{3-6}$cycloalkyl can be cyclopropyl, cyclobutyl, cyclopentyl, cyclohexyl, and isomeric forms thereof.

In some preferred compounds provided herein $C_{1-4}$ heteroalkyl can be hydroxymethyl, hydroxyethyl, and 2-methoxyethyl.

In some preferred compounds provided herein halo can be fluoro (F) or chloro (Cl).

In some preferred compounds provided herein $R^1$ is H, and $R^2$ is $CH_2NH_2$.

In some preferred embodiments, group $R^3$ is H, and $R^4$ is $CH_2OH$.

One preferred group of compounds provided herein is illustrated below.

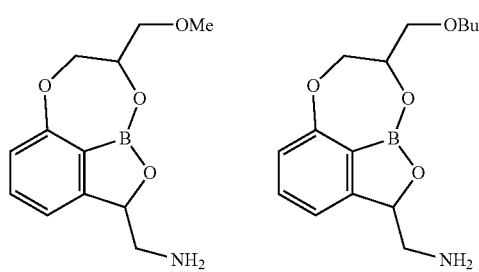

Additional group of compounds provided herein is illustrated below.

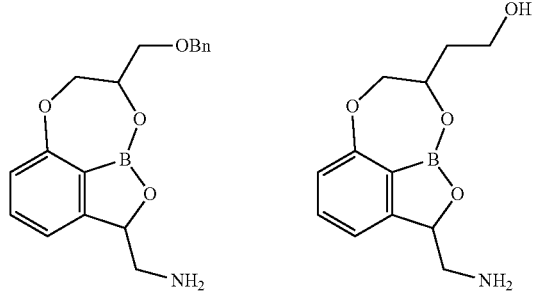

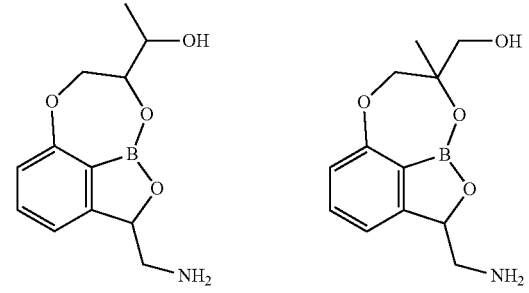

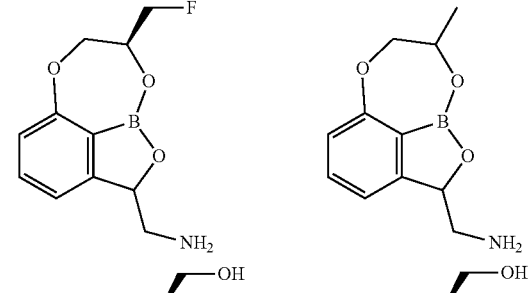

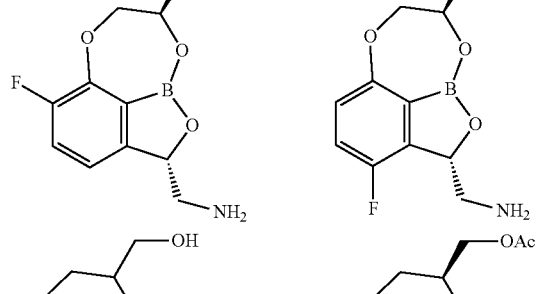

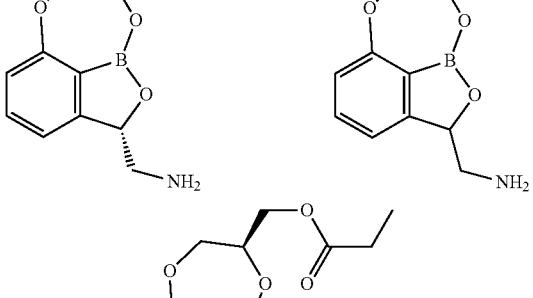

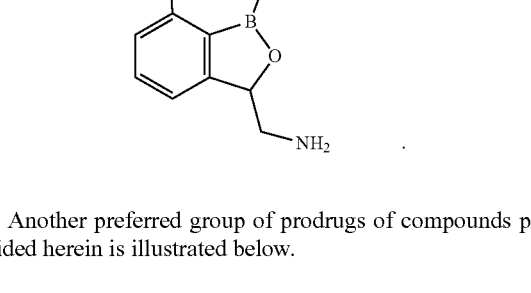

Another preferred group of prodrugs of compounds provided herein is illustrated below.

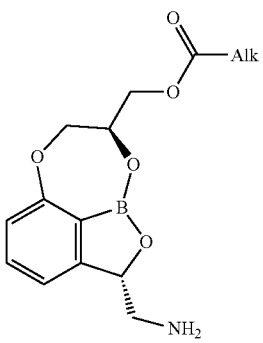

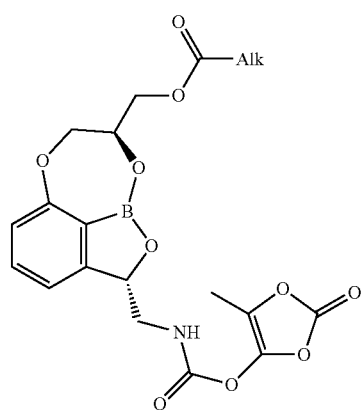

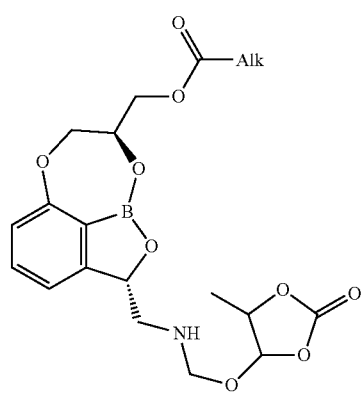

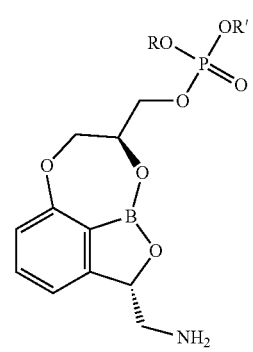

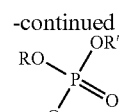
-continued

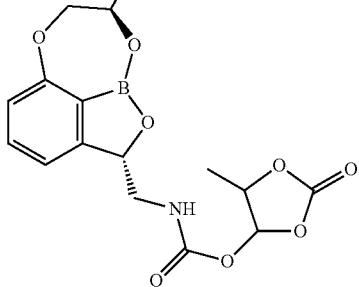

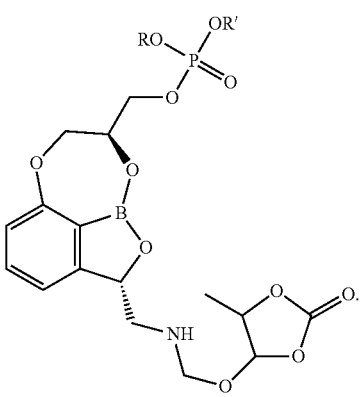

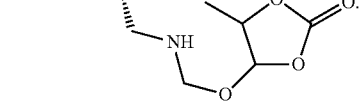

General Synthetic Methods

The compounds provided herein can be prepared in accordance with one or more of Schemes discussed below. Multitude of well-established methods for preparing boron compounds has been reviewed in a comprehensive monograph *Boronic Acids: Preparation, Applications in Organic Syntheses and Medicine*. Ed. Dennis G. Hall, Wiley-VCH Verlag GmbH & Co., 2005, pp. 1-549. These methods can be used either directly or with obvious variations to a trained chemist to prepare key intermediates and certain compounds provided herein.

Additional general methods for preparation of some bicyclic boron compounds have been described, for example, in publications WO 2010/080558 and US 2009/0227541.

It is also understood that, if so required, any racemic compound(s) or intermediate(s) provided herein can be separated into asymmetric chiral materials of a desired optically active isomers using conventional means, including but not limited to chiral liquid chromatography or co-crystallization with a chiral auxiliary reagent, such as a conventional commercial chiral acid or amine.

Suitable synthetic sequences are readily selected per specific structures provided herein, but within the art known to individuals practicing organic synthesis, such as methods summarized in available chemistry data bases, such as in CAS Scifinder and Elesevier Reaxys. Based on these general methods, the enablement for making the compounds provided herein is straightforward and can be practiced within a common professional knowledge. Some general synthetic methods to prepare the compounds provided herein are illustrated below in Schemes 1-6 (non-limiting, for illustration only).

One general approach to the compounds provided herein is illustrated in general Scheme 1.

Scheme 1. General synthesis of tricyclic dioxaboron compounds from aromatic or heteroaromatic alcohols.

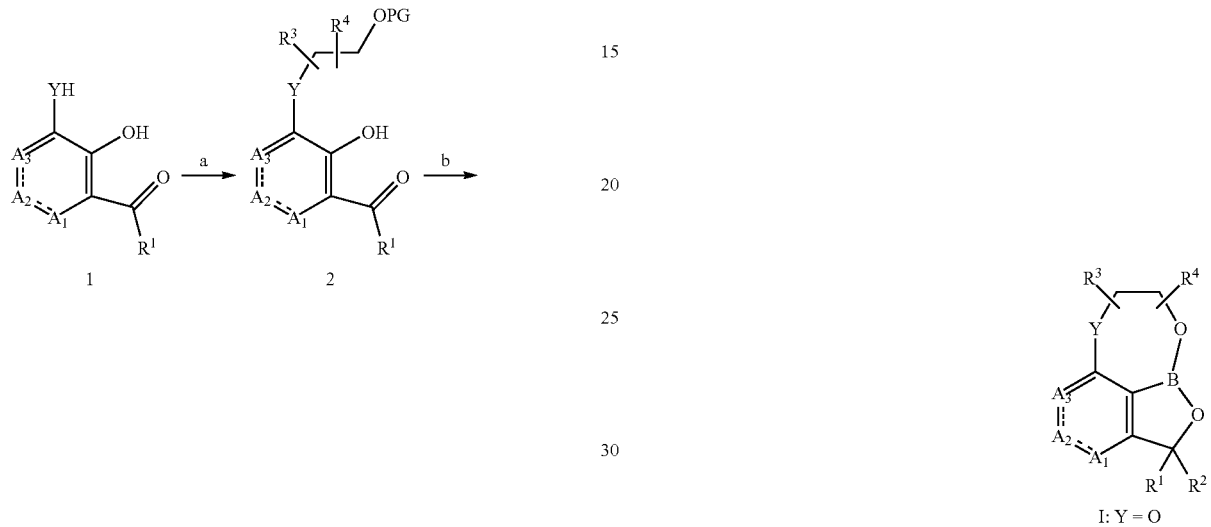

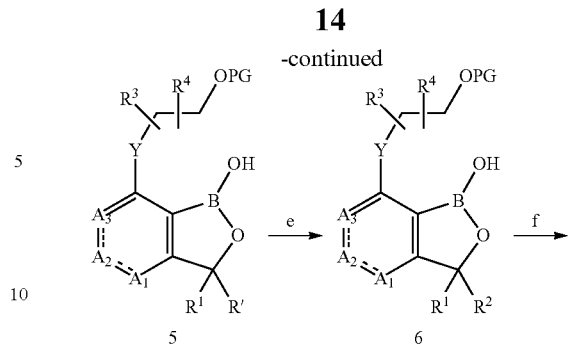

a) Alkylating agent such as halide, mesylate, or alike; base: K₂CO₃, LiOH, TEA, DBU, or alike; Mitsunobu reaction for alkylating with an alcohol reagent; b) triflating reagent: Tf₂O, 2-Tf₂N-5-Cl-pyridine, or alike; base K₂CO₃, TEA, DBU, or alike; c) Pd catalyst: Pd(dppf)₂Cl₂ DCM, Pd(OAc)₂, or alike; bis(pinacolato)diboron; base: KOAc, Na₂CO₃, or alike; d) methylene-active reagent Me—R': e.g. MeNO₂, MeCN, or alike; base: K₂CO₃, NaOH, TEA, DBU, or alike; e) R²-unmasking method, e.g. reduction for R' = NO₂: such as Raney-Ni/H₂, Pd/C/H₂, NiCl₂/NaBH₄, and alike; f) protective group (PG) deprotection method, e.g. Pd/C/H₂ for PG = Bn; Bu₄N⁺F⁻ or LiF for PG = TBS; trifluoroacetic acid (TFA) for PG = trityl, and alike.

Another general synthesis of the compounds provided herein is illustrated in Scheme 2. A multitude of the requisite aromatic and heteroaromatic bromides of the type 7 is commercially available or can be readily prepared using literature methods.

Scheme 2. General synthesis of tricyclic dioxaboron compounds from aromatic or heteroaromatic halides (exemplified for halide = bromide).

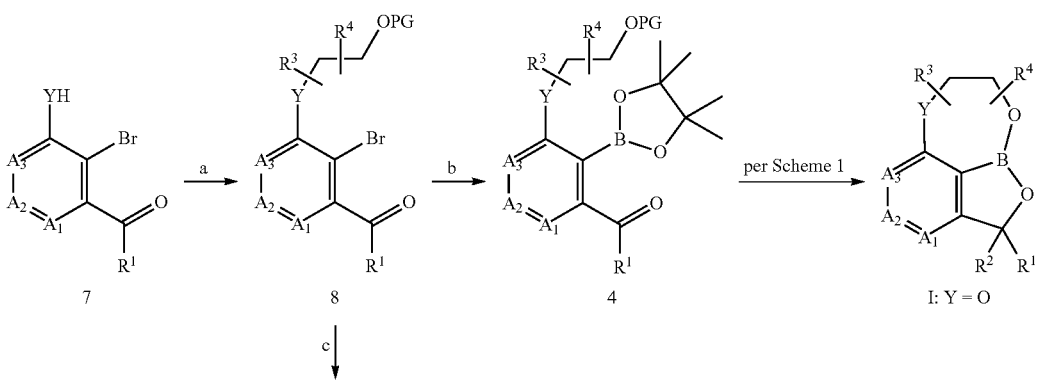

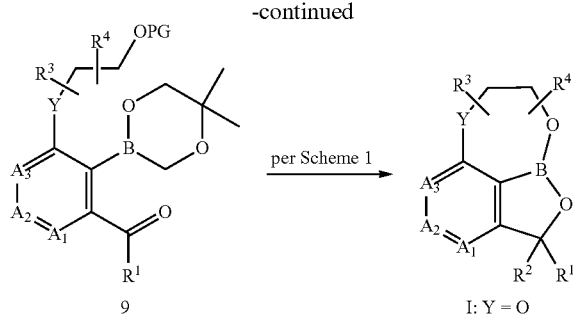

a) Alkylating agent such as halide, mesylate, or alike; base: K₂CO₃, LiOH, TEA, DBU, or alike; Mitsunobu reaction for alkylating with an alchohol reagent; b) Pd catalyst: Pd(dppf)₂Cl₂ DCM, Pd(OAc)₂, or alike; bis(pinacolato)diboron; base: KOAc, Na₂CO₃, or alike; c) Pd catalyst: Pd(dppf)₂Cl₂ DCM, Pd(OAc)₂, or alike; bis(neopentylglycolate)diboron; base: KOAc, Na₂CO₃, or alike.

Additional general methods for synthesis of compounds provided herein are exemplified by general Scheme 3.

Scheme 3. General synthesis of tricyclic oxazaboron compounds from aromatic or heteroaromatic halides (exemplified for halide = bromide).

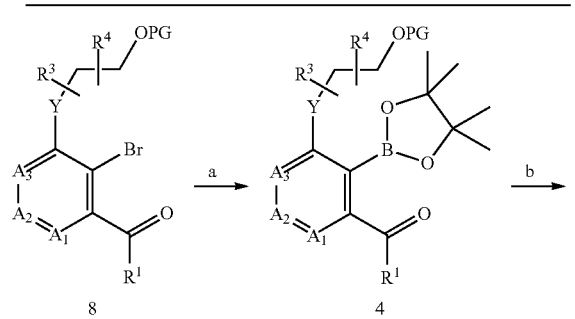

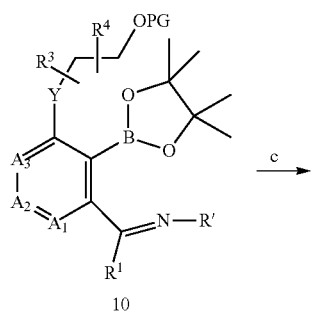

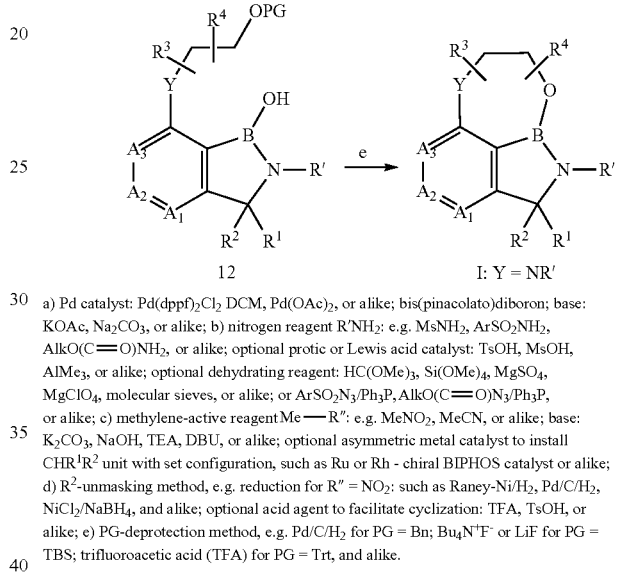

a) Pd catalyst: Pd(dppf)₂Cl₂ DCM, Pd(OAc)₂, or alike; bis(pinacolato)diboron; base: KOAc, Na₂CO₃, or alike; b) nitrogen reagent R'NH₂: e.g. MsNH₂, ArSO₂NH₂, AlkO(C=O)NH₂, or alike; optional protic or Lewis acid catalyst: TsOH, MsOH, AlMe₃, or alike; optional dehydrating reagent: HC(OMe)₃, Si(OMe)₄, MgSO₄, MgClO₄, molecular sieves, or alike; or ArSO₂N₃/Ph₃P, AlkO(C=O)N₃/Ph₃P, or alike; c) methylene-active reagent Me—R'': e.g. MeNO₂, MeCN, or alike; base: K₂CO₃, NaOH, TEA, DBU, or alike; optional asymmetric metal catalyst to install CHR¹R² unit with set configuration, such as Ru or Rh - chiral BIPHOS catalyst or alike; d) R²-unmasking method, e.g. reduction for R'' = NO₂: such as Raney-Ni/H₂, Pd/C/H₂, NiCl₂/NaBH₄, and alike; optional acid agent to facilitate cyclization: TFA, TsOH, or alike; e) PG-deprotection method, e.g. Pd/C/H₂ for PG = Bn; Bu₄N⁺F⁻ or LiF for PG = TBS; trifluoroacetic acid (TFA) for PG = Trt, and alike.

Another general approach to the compounds provided herein is illustrated in general Scheme 4.

Scheme 4. General synthesis of tricyclic benzo[cd] azulene dioxaboron compounds.

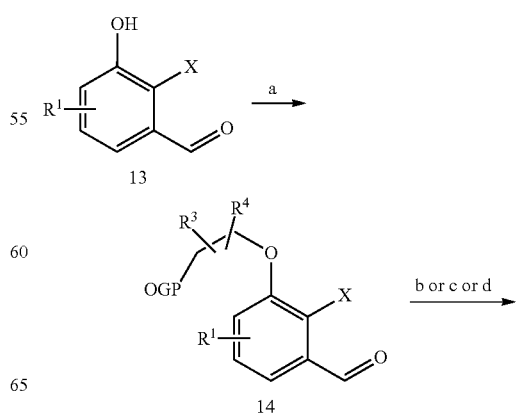

17
-continued

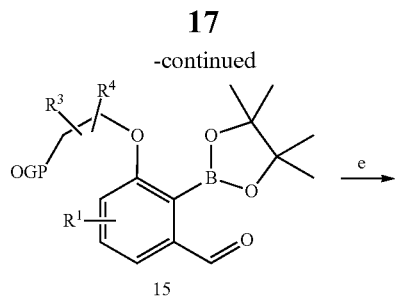

18
-continued

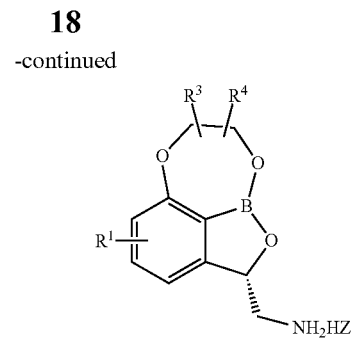

I: Y = O a) Alkylating agent such as halide mesylate, or alike; base: K₂CO₃, LiOH, TEA, DBU, or alike; Mitsunobu reaction for alkylating with an alcohol reagent; b) for X = halide (such as bromide): Pd catalyst: Pd(dppf)₂Cl₂ DCM, Pd((OAc)₂, or alike; bis(pinacoloato)diboron; base: KOAc, Na₂CO₃, or alike; c) for X = H: lithiation reagent such BuLi, LDA, or alike; trialkyl broate; d) for X = OH: triflating reagent: Tf₂O, 2-Tf₂N-5-Cl-pyridine, or alike; base: K₂CO₃, TEA, DBU, or alike; then same as in method (b); e) nitromethane or equivalent thereof; with or without base such as NaOH, K₂CO₃, and alike; f) PG-deprotection method, e.g. Pd/C/H₂ for PG = Bn; Bu₄N⁺F⁻ or LiF for PG TBS; trifluoroacetic acid (TFA) for PG = Trt, aq. LiOH for ester, and alike; g) reducing agent(s) and an amine protecting agent: H₂/Pd/C, NaBH₄, SnCl₂, or alike, then with Boc₂O, or CbzCl, or aromatic aldehyde; h) primary amine protection group PG′ removal reagent(s): acid for trityl, or Boc; H₂/Pd/C for benzyl or Cbz; aqueous base for amide, sulfonamide or carbamate, then salt-forming acid, such as aq. HCl, MsOH, or alike.

Yet another general synthesis of compounds provided herein is illustrated by Scheme 5.

Scheme 5. General synthesis of tricyclic dioxaborepine compounds.

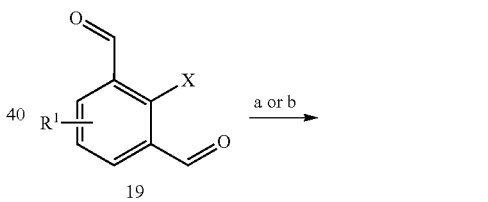

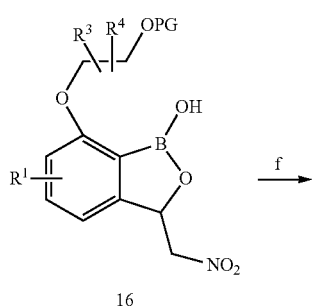

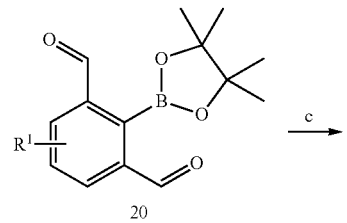

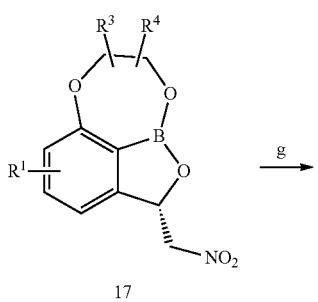

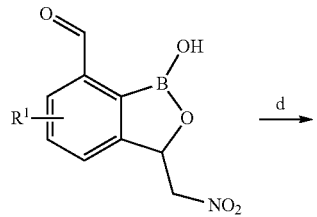

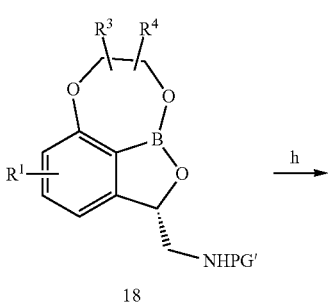

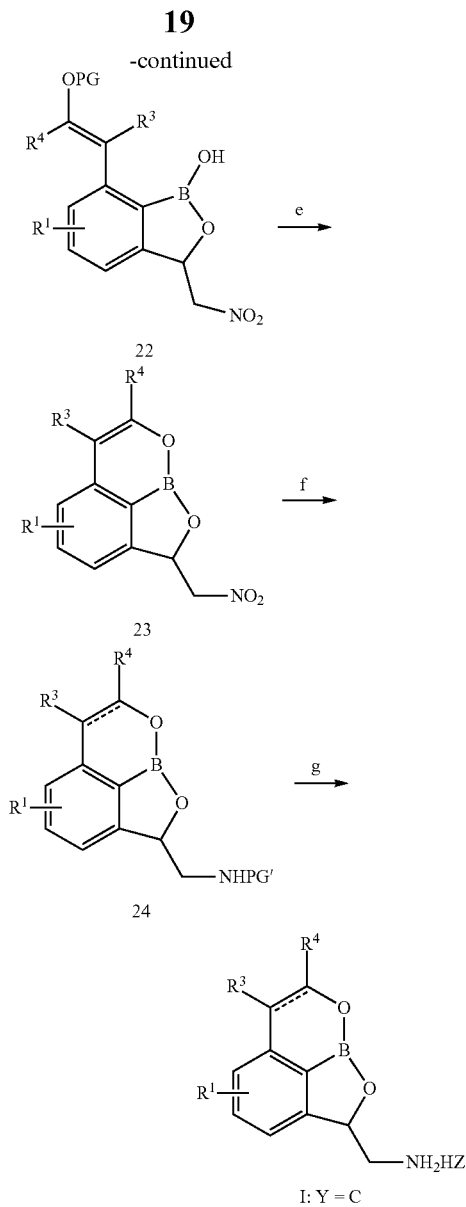

a) For X = halide (such as bromide): Pd catalyst: Pd(dppf)₂Cl₂ DCM, Pd(OAc)₂, or alike; bis(pinacolato)diboron; base: KOAc, Na₂CO₃, or alike; b) for X = H: lithiation reagent such n-BuLi, LDA, or alike; trialkyl borate; c) nitromethane or equivalent thereof; with or without base such as NaOH, K₂CO₃, and alike; d) PG-deprotection method, e.g. Pd/C/H₂ for PG = Bn; Bu₄N⁺F⁻ or LiF for PG TBS; trifluoroacetic acid (TFA) for PG = Trt, aq. LiOH for ester, and alike; e) reducing agent(s) and an amine protecting agent: H₂/Pd/C, NaBH₄, SnCl₂, or alike, then with Boc₂O, or CbzCl, or aromatic aldehyde; h) primary amine protection group PG' removal reagent(s): acid for trityl, or Boc; H₂/Pd/C for benzyl or Cbz; aqueous base for amide, sulfonamide or carbamate, then salt-forming acid, such as aq. HCl, MsOH, or alike.

If needed, the general illustrative methods of Schemes 1-5 can be combined or modified based on the known to a trained chemist art, to employ for the preparation of a specific compound provided herein.

Further, prodrug derivatives of the compounds provided herein could be produced, for example, by conventional acylation of available alcohol or amine side chains, or by phosphorylation of available alcohol groups, and utilizing routine protection/deprotection sequence as needed.

Additional detailed synthetic schemes for the syntheses of specific compounds provided herein are illustrated by methods described for Examples below.

EXAMPLES

Embodiments provided herein are described in the following examples, which are meant to illustrate and not limit the scope of any invention provided herein. Common abbreviations well known to those with ordinary skills in the synthetic art used throughout. ¹H NMR spectra (δ, ppm) are recorded on 300 MHz or 400 MHz instrument in DMSO-$d_6$ unless specified otherwise. Mass-spectroscopy data for a positive ionization method are provided. Chromatography means silica gel chromatography unless specified otherwise. TLC means thin-layer chromatography. HPLC means reverse-phase HPLC. Unless specified otherwise, all reagents were either from commercial sources, or made by conventional methods described in available literature.

Example 1

((8R)-2-(Aminomethyl)-7,8-dihydro-2H-1,6,9-trioxa-9a-borabenzo[cd]azulen-8-yl)methanol hydrochloride

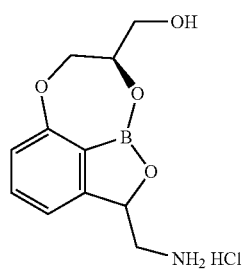

Example 1

Scheme for preparation of the compound of Example 1:

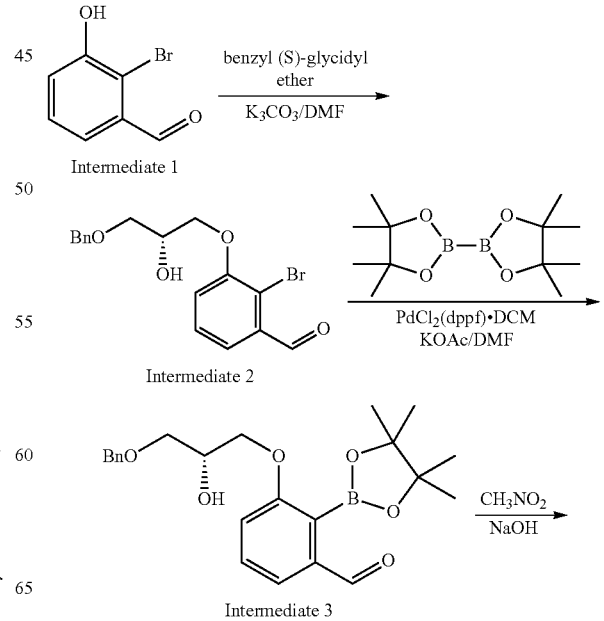

-continued

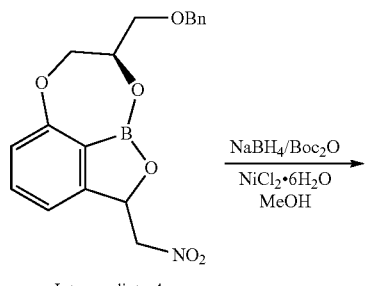

Intermediate 4

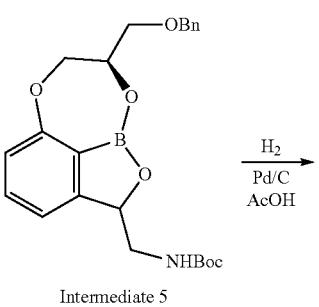

Intermediate 5

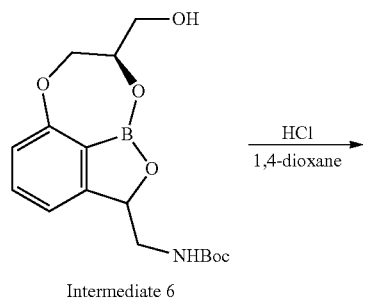

Intermediate 6

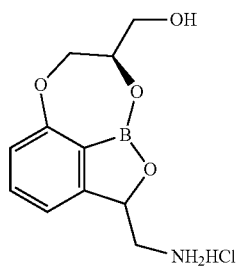

Example 1

Intermediate 2.

K$_2$CO$_3$ (1.0 g) was added to 2-bromo-3-hydroxybenzaldehyde (1.5 g) in DMF (8 mL), followed by benzyl (S)-glycidyl ether (1.2 mL). The suspension was stirred at about 120° C. for about 1.5 h. After the starting bromide was consumed, the mixture was cooled down to r.t., diluted with brine and extracted with EtOAc. EtOAc was removed under vacuum and the residue was purified by silica gel column chromatography (eluent: 20-40% EtOAc/hexane) to afford the Intermediate 2 as an off-white oil (2.36 g). MS (m/z): 364.9, 366.9 [M+H].

Intermediate 3.

Intermediate 2 (2.16 g) was mixed with bis(pinacolato)diboron (3.0 g) and dissolved in DMF (12 mL). The solution was degassed, and KOAc (1.74 g) was added, followed by PdCl$_2$(dppf)$_2$.DCM (0.24 g). The suspension was again degassed three times with nitrogen, and then heated at about 90° C. for about 14 h. The reaction was worked up with EtOAc/brine/H$_2$O, and the product was purified by silica gel column chromatography (eluent: 10-40% EtOAc/hexane). Fractions containing the product were collected and evaporated under vacuum to afford the Intermediate 3. MS (m/z): 353.0 [Boronic acid+Na].

Intermediate 4.

The total of the Intermediate 3 from preceding step was dissolved in THF (6 mL) and water (18 mL). The biphasic solution was cooled down with ice/water, and nitromethane (0.95 mL) was added, followed by a solution of 10% aq. NaOH (about 2.4 mL). The reaction was stirred at r.t. o.n. and then acidified with AcOH to pH ca. 3-5. The suspension was extracted with EtOAc. The combined organic layers were evaporated under vacuum, and the residue was purified by silica gel column chromatography (eluent: 2-6% MeOH/DCM) to afford the Intermediate 4. MS (m/z): 356.0 [M+H].

Intermediate 5.

NiCl$_2$.6H$_2$O (0.34 g) was added to Intermediate 4 (0.5 g) in MeOH (6 mL), followed by Boc$_2$O (0.62 g). The solution was cooled down with ice/water, and then NaBH$_4$ (0.65 g) was added portionwise with stirring. The mixture was stirred at r.t. o.n. and then acidified with AcOH to pH ca. 3-5. Most of volatiles were removed under vacuum, and the residue was re-dissolved in EtOAc/H$_2$O, filtered through Celite, and then extracted with EtOAc (3×). The combined organic layers were concentrated in vacuo, and the residue was purified by silica gel column chromatography (eluent: 2-6% MeOH/DCM) to afford the Intermediate 5. MS (m/z): 326.0 [M-Boc+H].

Intermediate 6.

Intermediate 5 (0.26 g) in AcOH (5 mL) was hydrogenated at r.t. with 10% Pd/C (about 100 mg) for 2 h. The mixture was filtered through Celite and the solvent was removed under vacuum. The residue was purified on a silica gel column (eluent: 0.5-2% MeOH/DCM) to afford the Intermediate 6. MS (m/z): 236.1 [M-Boc+H].

Compound of Example 1

Intermediate 6 (0.12 g, 0.36 mmol) was dissolved in 4N HCl in 1,4-dioxane (5 mL), and the solution was stirred at r.t. for about 2 h. The volatiles were removed under vacuum, and the residue was dissolved in water (about 3 mL) and filtered through 0.45 μM membrane filter. The aq. solution was lyophilized to afford the compound of Example 1. $^1$H NMR: 8.12 (br s, 3H), 7.49 (t, J=7.80 Hz, 1H), 7.13 (d, J=7.50 Hz, 1H), 6.91 (d, J=9.10 Hz, 1H), 5.48 (d, J=7.50 Hz, 1H), 5.15 (m, 1H), 4.70 (m, 1H), 4.32 (m, 1H), 4.05 (m, 1H), 3.49 (m, 3H), 2.90 (m, 1H). MS (m/z): 235.9 [M+H].

Example 2

((2R,8R)-2-(Aminomethyl)-7,8-dihydro-2H-1,6,9-trioxa-9a-borabenzo[cd]azulen-8-yl)methanol hydrochloride

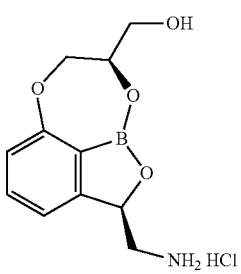

Compound of Example 2

The compound of Example 1 comprising a mixture of two diastereomers is subjected to HPLC separation (eluent: 0.1% trifluoroacetic acid in water/MeCN gradients) and the fractions containing the product are collected and lyophilized with addition of aq. HCl to afford the compound of Example 2.

Example 3

((2S,8R)-2-(Aminomethyl)-7,8-dihydro-2H-1,6,9-trioxa-9a-borabenzo[cd]azulen-8-yl)methanol hydrochloride

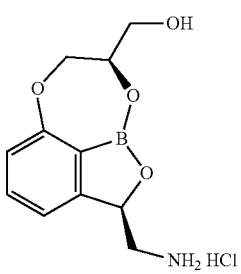

Compound of Example 3

Method A

The compound of Example 1 comprising a mixture of two diastereomers is subjected to HPLC separation (eluent: 0.1% trifluoroacetic acid (TFA) in water/MeCN gradient) and the fractions containing the product are collected and lyophilized with addition of aq. HCl to afford the compound of Example 3.

Method B

Scheme for preparation of the compound of Example 3 using Method B:

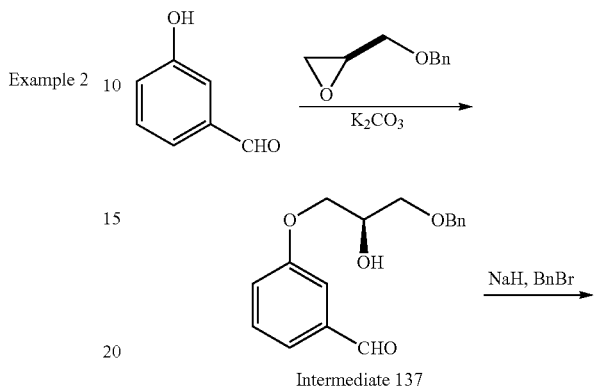

Intermediate 137

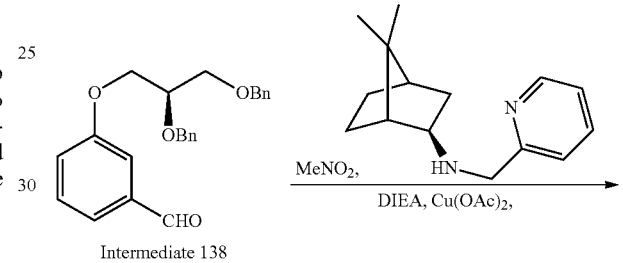

Intermediate 138

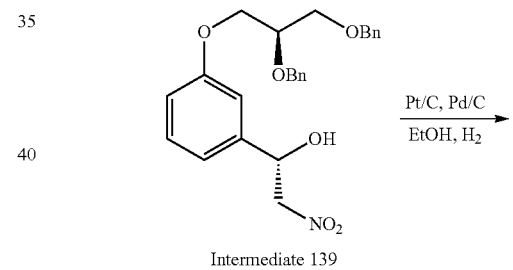

Intermediate 139

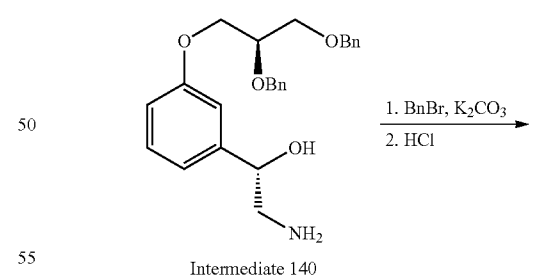

Intermediate 140

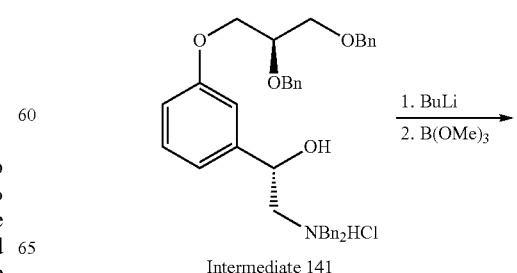

Intermediate 141

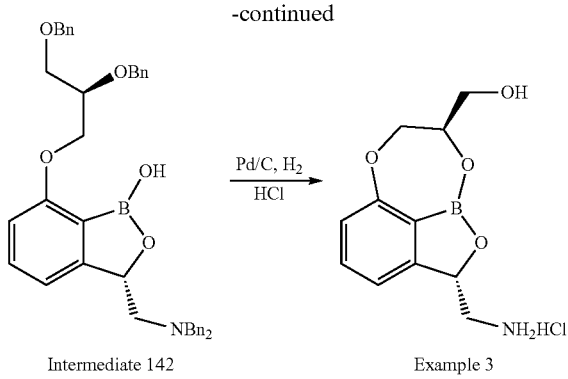

Intermediate 142

Example 3

Intermediate 137.
Method I.

K₂CO₃ (12.6 g) was added to 3-hydroxybenzaldehyde (7.43 g) and (S)-2-((benzyloxy)methyl)oxirane (10.0 g) in DMF (45 mL), and the mixture was stirred at 90° C. for 5 h. Upon cooling to r.t., EtOAc (150 mL) and water (150 mL) were added, and the aqueous layer was extracted with EtOAc (2×150 mL). The combined organic layers were washed with brine and dried (Na₂SO₄). Solvent was evaporated under vacuum to afford the crude product that was purified by column chromatography (EtOAc/PE (petroleum ether) 1:4) to afford the Intermediate 137 as yellow oil.

Method II.

Performed as described above for Method I, except with the procedure scaled-up to 100 g of starting 3-hydroxybenzaldehyde, and using the resulted reaction solution directly at the next step, without isolation of the Intermediate 137.

Intermediate 138.

60% NaH in oil (38 g) was added portionwise to the solution of the Intermediate 137 from the preceding step of Method II at 0° C. under N₂, and the resulting solution was stirred for 1 h. BnBr (114 mL) was added dropwise with stirring at 0° C., the reaction mixture was allowed to warm up to r.t. and stirred until no Intermediate 137 was left per LCMS analysis. The reaction mixture was quenched with ice-cold water, and the product was extracted with EtOAc. Resulted organic layer was dried (Na₂SO₄), and solvent was evaporated under vacuum. The crude product was purified by column chromatography (gradient EtOAc/PE from 1:12 to 1:10) to afford the Intermediate 138.

Intermediate 139.

Copper (II) acetate (0.48 g) and (1S,2S,4R)-1,7,7-trimethyl-N-(pyridin-2-ylmethyl)bicyclo[2.2.1]heptan-2-amine (0.36 g) were dissolved in EtOH (12 mL) and THF (18 mL). The solution was stirred at r.t. for 1 h, then a solution of the Intermediate 138 (30 g) in EtOH (108 mL) and THF (162 mL) was added. The mixture was cooled at ca. −30 to −40° C., and nitromethane (43 mL) was added slowly with stirring while maintaining the temperature below −30° C. DIEA (13.9 mL) was added, and the reaction mixture was stirred at −30° C. until the Intermediate 138 was consumed (ca. 24-56 h) by LCMS. TFA (1.2 g) was added, and the reaction was stirred for ca. 10 min. Volatiles were removed under vacuum, and the residue was dissolves in MTBE, washed with 1N HCl, water and then filtered through Celite pad. The filtrate was dried (Na₂SO₄), and the solvent was removed under vacuum. The crude material was purified by column chromatography (EtOAc/PE 1:5) to afford the product as yellow oil.

Intermediate 140.

Intermediate 139 (8.0 g) was dissolved in EtOH (90 mL), and then 5% Pt/C (1.45 g) and 10% Pd/C (2.62 g) were added. The reaction mixture was stirred under H₂ for ca. 1.5 h at r.t., then filtered, and the resulting solution of the Intermediate 140 was used at the next step without further purification. MS (m/z): 408.0 [M+H].

Intermediate 141.

BnBr (13.65 g, 2.1 eq.) and K₂CO₃ (13.14 g, 2.5 eq.) were added to the solution of the Intermediate 140 obtained at the preceding step. The mixture was stirred o.n. and filtered aiding with EtOH. The filtrate was concentrated under vacuum to a volume of about 100 mL. This solution was diluted with water (65 mL) and stirred at 50° C. Conc. aq. HCl (4 mL) was added, and the mixture was stirred at 50° C. for ca. 30 min, then stirred at ca. 0° C. for 30 min. The product was filtered off and washed with cold 20% aqueous ethanol (80 mL). Solvent was removed under vacuum to afford the Intermediate 141 as a white solid. MS (m/z): 570.3 [M-HCl—H₂O+H].

Intermediate 142.

2.6 M BuLi in hexanes (8.8 mL) was added dropwise with stirring over ca. 10 min to a solution of the Intermediate 141 (5 g) in toluene (32 mL) under nitrogen. The reaction mixture was stirred at r.t. for ca. 1 h, and cooled to ca. −30 to −40° C. Extra BuLi solution (3.1 mL) was added slowly, followed by extra BuLi solution (8.9 mL) at −25 to −30° C. The mixture was stirred for at this temperature for ca. 2-3 h, and then B(OMe)₃ (4.5 mL) was added, followed by dry THF (3.6 mL). The mixture was allowed to warm up to ca. 15-25° C. over ca. 30-60 min. 5% Aq. NaHCO₃ (50 mL) was added, and the mixture was stirred for about 15 min. The resulting suspension was filtered aiding with MTBE (ca. 20 mL). The filtrate was washed with water (4×20 mL) and dried (Na₂SO₄). Solvent was removed under vacuum, and the crude material purified by column chromatography to afford the Intermediate 142 as yellow oil. MS (m/z): 614.2 [M+H].

Compound of Example 3

Intermediate 142 (14 g) was dissolved in MeOH (120 mL) with 1N aq. HCl (25 mL). Pd/C (10%) was added, and the mixture was stirred under H₂ at 50° C. until the reaction was completed by LCMS. The mixture was filtered aiding with MeOH, and volatiles were removed under vacuum. The crude material was recrystallized from 2-propanol to afford the compound of Example 4 as a white solid. ¹H NMR: 8.21 (br s, 3H), 7.50 (t, J=8.00 Hz, 1H), 7.15 (d, J=7.20 Hz, 1H), 6.92 (d, J=8.00 Hz, 1H), 5.51 (m, 1H), 5.18 (m, 1H), 4.72 (m, 1H), 4.32 (m, 1H), 4.03 (m, 1H), 3.60-3.42 (m, 3H), 2.92 (m, 1H). MS (m/z): MS (m/z): 235.6.

Example 4

((8S)-2-(Aminomethyl)-7,8-dihydro-2H-1,6,9-trioxa-9a-borabenzo[cd]azulen-8-yl)methanol hydrochloride

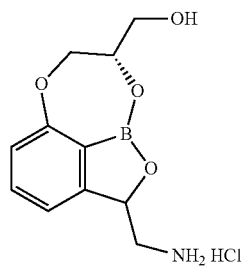

Example 4

Scheme for preparation of the compound of Example 4:

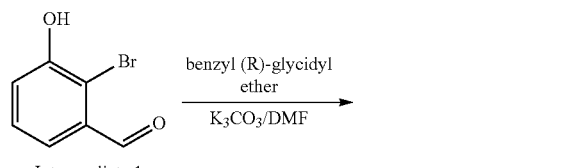

Intermediate 1

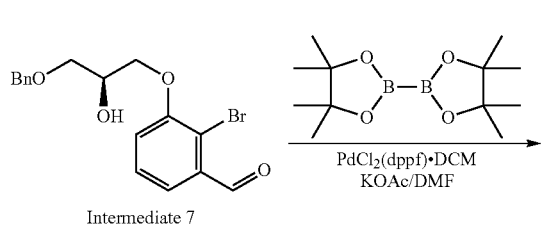

Intermediate 7

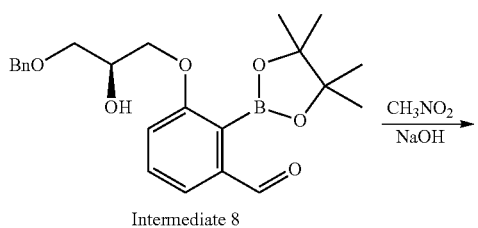

Intermediate 8

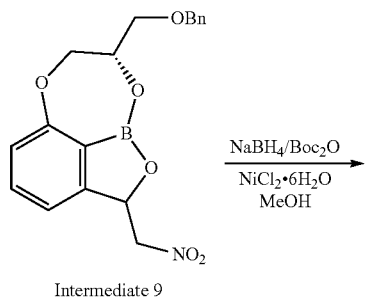

Intermediate 9

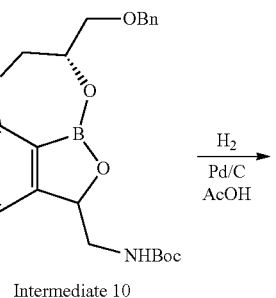

Intermediate 10

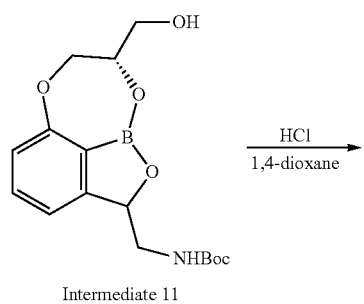

Intermediate 11

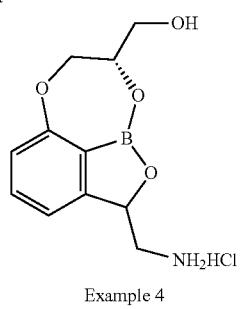

Example 4

Compound of Example 4

The compound of Example 4 was prepared analogously to the procedures for preparation of the compound of Example 1, except using benzyl (R)-glycidyl ether instead of benzyl (S)-glycidyl ether to prepare the Intermediate 7, and then employing respective Intermediates 8-11 in procedures described above for methods with analogous Intermediates 3-6 (employed above to prepare the compound of Example 1).
$^1$H NMR: 8.25 (br s, 3H), 7.48 (t, J=7.20 Hz, 1H), 7.13 (d, J=7.50 Hz, 1H), 6.90 (d, J 7.80, 1H), 5.51 (d, J=5.10 Hz, 1H), 4.70 (m, 1H), 4.60 (m, 1H), 4.20 (m, 1H), 3.50-3.20 (m, overlapped with water signal), 2.92 (m, 1H). MS (m/z): 235.9 [M+H].

Example 5

(8-(Methoxymethyl)-7,8-dihydro-2H-1,6,9-trioxa-9a-borabenzo[cd]azulen-2-yl)methanamine hydrochloride

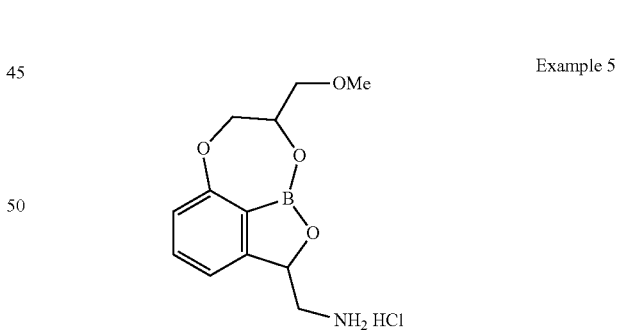

Scheme for preparation of the compound of Example 5:

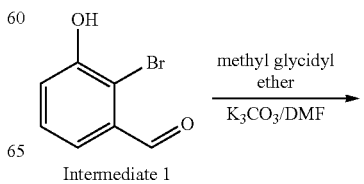

Intermediate 1

4.22 (m, 1H), 3.43 (m, overlapped with water signal), 2.90 (m, 1H). MS (m/z): 250.1 [M+H].

Example 6

(8-(Butoxymethyl)-7,8-dihydro-2H-1,6,9-trioxa-9a-borabenzo[cd]azulen-2-yl)methanamine hydrochloride

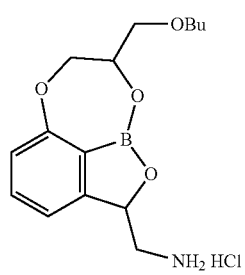

Example 6

Scheme for preparation of the compound of Example 6:

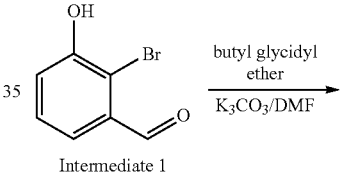

Intermediate 1

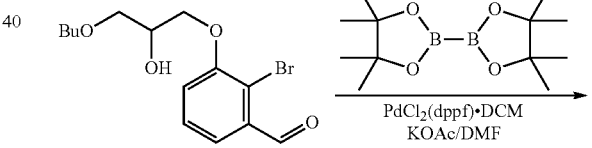

Intermediate 16

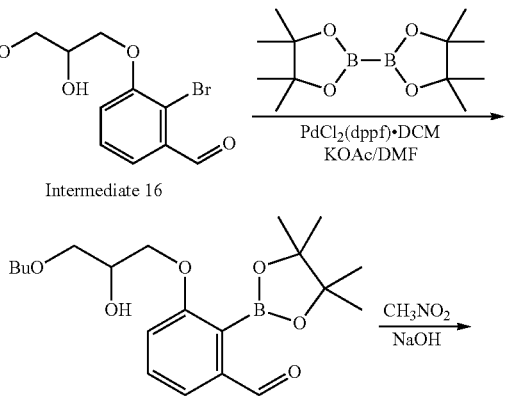

Intermediate 17

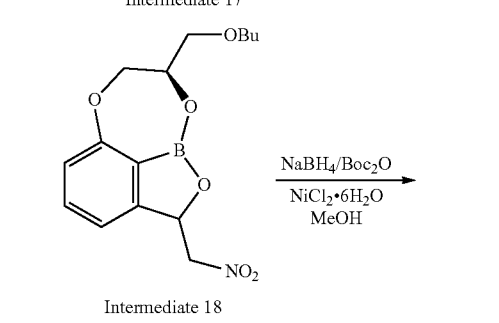

Intermediate 18

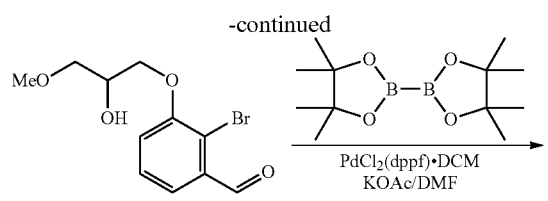

Intermediate 12

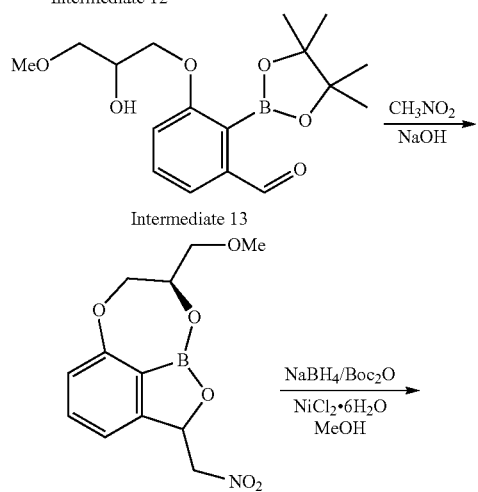

Intermediate 13

Intermediate 14

Intermediate 15

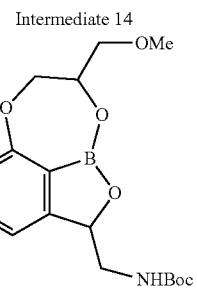

Example 5

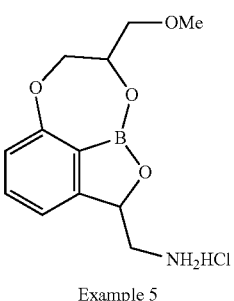

Compound of Example 5

The compound of Example 5 was prepared analogously to the procedures for preparation of the compound of Example 1, except using methyl-glycidyl ether instead of benzyl (S)-glycidyl ether to prepare the Intermediate 12, and then employing respective Intermediates 13-15 in procedures described above for methods with analogous Intermediates 3-5 (employed above to prepare the compound of Example 1).
$^1$H NMR: 8.19 (br s, 3H), 7.48 (t, J=7.20 Hz, 1H), 7.15 (d, J=7.45 Hz, 1H), 6.90 (m, 1H), 5.50 (m, 1H), 4.60 (m, 2H),

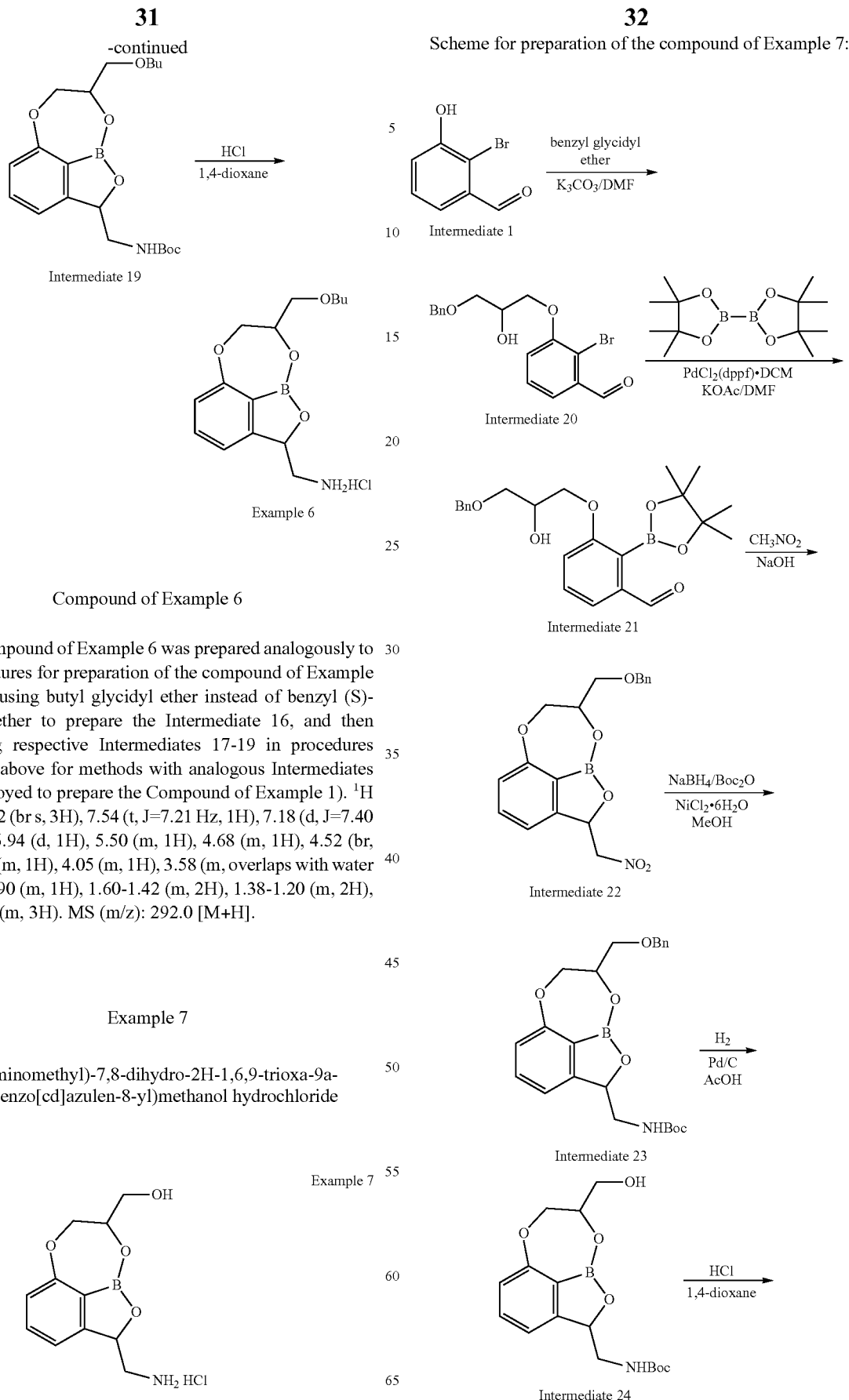

Compound of Example 6

The compound of Example 6 was prepared analogously to the procedures for preparation of the compound of Example 1, except using butyl glycidyl ether instead of benzyl (S)-glycidyl ether to prepare the Intermediate 16, and then employing respective Intermediates 17-19 in procedures described above for methods with analogous Intermediates 3-5 (employed to prepare the Compound of Example 1). $^1$H NMR: 8.22 (br s, 3H), 7.54 (t, J=7.21 Hz, 1H), 7.18 (d, J=7.40 Hz, 1H), 6.94 (d, 1H), 5.50 (m, 1H), 4.68 (m, 1H), 4.52 (br, 1H), 4.21 (m, 1H), 4.05 (m, 1H), 3.58 (m, overlaps with water signal), 2.90 (m, 1H), 1.60-1.42 (m, 2H), 1.38-1.20 (m, 2H), 0.96-0.80 (m, 3H). MS (m/z): 292.0 [M+H].

Example 7

2-(Aminomethyl)-7,8-dihydro-2H-1,6,9-trioxa-9a-borabenzo[cd]azulen-8-yl)methanol hydrochloride

33

-continued

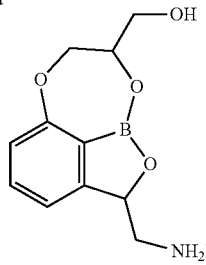

Example 7

Compound of Example 7

The compound of Example 4 was prepared analogously to the procedures for preparation of the compound of Example 1, except using benzyl glycidyl ether instead of benzyl (S)-glycidyl ether to prepare the Intermediate 20, and then employing respective Intermediates 21-24 in procedures described above for methods with analogous Intermediates 3-6 (employed to prepare the Compound of Example 1). $^1$H NMR (CD$_3$OD): 7.49 (t, J=7.20 Hz, 1H), 7.08 (d, J=7.20 Hz, 1H), 6.93 (d, J=7.80 Hz, 1H), 5.54 (m, 1H), 4.40 (m, 1H), 4.21 (m, 1H), 4.05 (m, 1H), 3.80-3.52 (m, 4H), 3.01 (m, 1H). MS (m/z): 235.9 [M+H].

Example 8

(8-((Benzyloxy)methyl)-7,8-dihydro-2H-1,6,9-trioxa-9a-borabenzo[cd]azulen-2-yl)methanamine hydrochloride

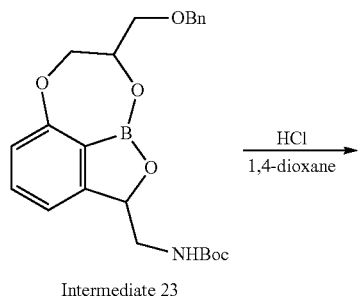

Example 8

Scheme for preparation of the compound of Example 8:

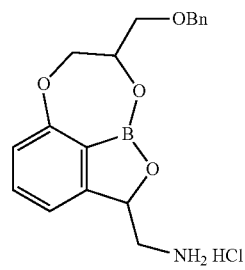

Intermediate 23

34

-continued

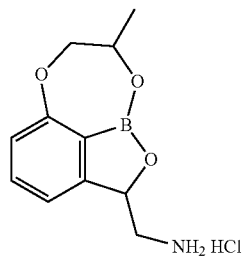

Example 8

Compound of Example 8

Intermediate 23 (20 mg) was dissolved in 4N HCl in 1,4-dioxane (0.5 mL), and the solution was stirred at r.t. for 1 h. The volatiles were removed under vacuum, and the residue was dissolved in water (about 2 mL) and filtered. The aqueous solution lyophilized to afford the compound of Example 8. $^1$H NMR (CD$_3$OD): 7.49 (t, J=7.80 Hz, 1H), 7.38-7.20 (m, 5H), 7.07 (d, J=6.90 Hz, 1H), 6.92 (dd, J 7.80 and 1.20 Hz, 1H), 5.48 (m, 1H), 4.57 (m, 2H), 4.40-4.02 (m, 2H), 3.80-3.50 (m, 4H), 3.00 (m, 1H). MS (m/z): 326.1.0 [M+1].

Example 9

(8-Methyl-7,8-dihydro-2H-1,6,9-trioxa-9a-borabenzo[cd]azulen-2-yl)methanamine hydrochloride Example 9

Scheme for preparation of the compound of Example 9:

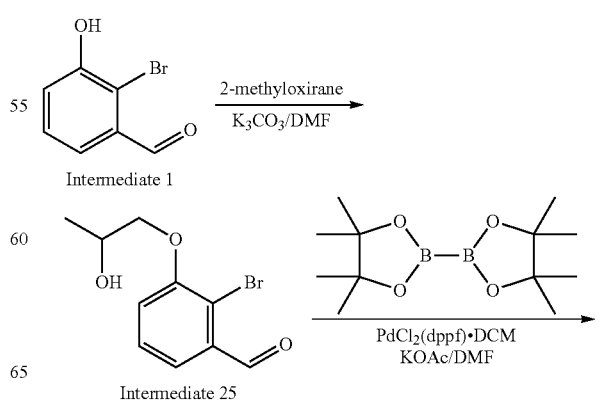

Intermediate 1

Intermediate 25

-continued

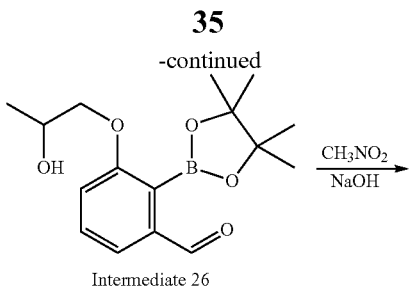
Intermediate 26

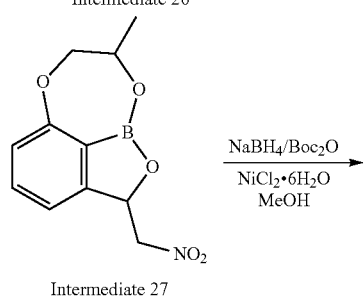
Intermediate 27

Intermediate 28

Intermediate 29

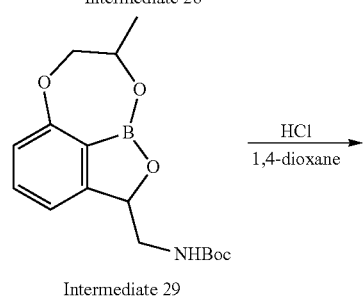
Example 9

Compound of Example 9

The compound of Example 9 was prepared analogously to the procedures for preparation of the compound of Example 1, except using methyl oxirane instead of benzyl (S)-glycidyl ether to prepare the Intermediate 25, and then employing respective Intermediates 26-29 in procedures described above for methods with analogous Intermediates 3-6 (employed to prepare the compound of Example 1). ¹H NMR: 8.19 (br. s, 3H), 7.48 (t, J=7.50 Hz, 1H), 7.13 (d, J=7.20 Hz, 1H), 6.91 (m, 1H), 5.50 (m, 1H), 4.58-4.50 (m, 2H), 4.22-4.15 (m, 1H), 3.70-3.60 (m, 1H), 2.89 (m, 1H), 1.39-1.21 (m, 3H). MS (m/z): 220.1 [M+1].

Reference Example 10

3-(Aminomethyl)-7-(3-hydroxypropoxy)benzo[c][1,2]oxaborol-1(3H)-ol hydrochloride

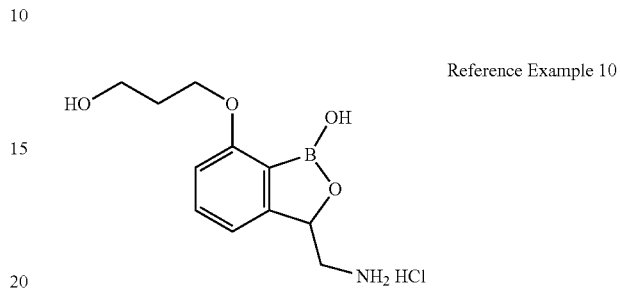
Reference Example 10

Reference Compound of Example 10

The reference Compound of Example 10 was prepared analogously to the procedures described in a publication US 2009/0227541. MS (m/z): 238.0 [M+H].

Example 11

(2-(Aminomethyl)-7,8-dihydro-2H-1,6,9-trioxa-9a-borabenzo[cd]azulen-7-yl)methanol hydrochloride

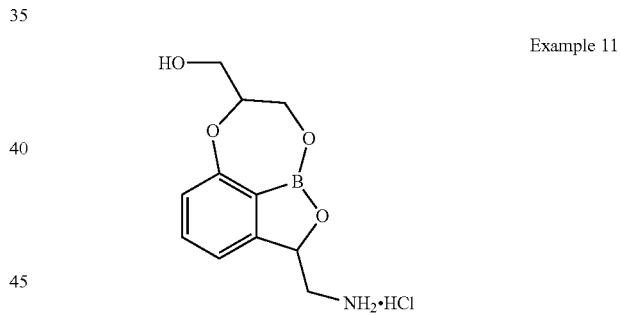
Example 11

Scheme for preparation of the compound of Example 11:

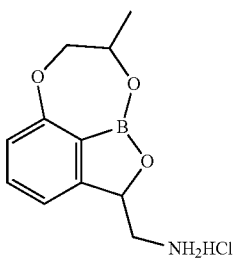
Intermediate 30

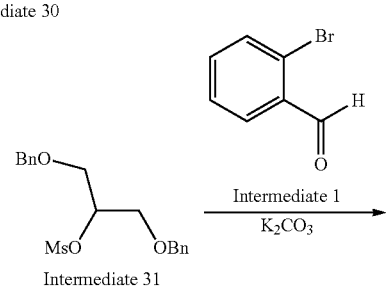
Intermediate 31

-continued

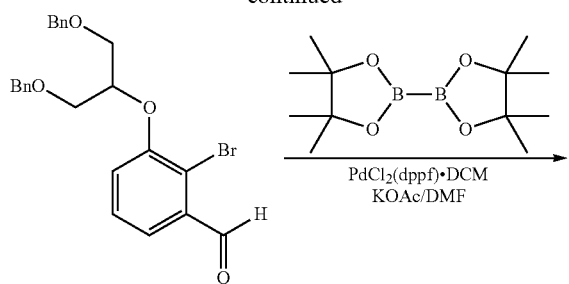

Intermediate 32

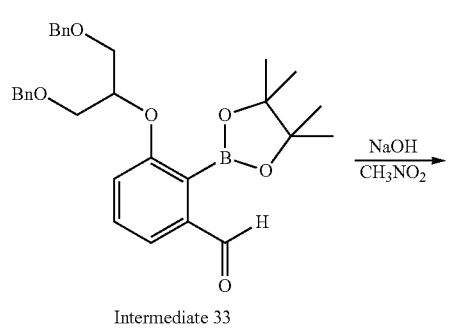

Intermediate 33

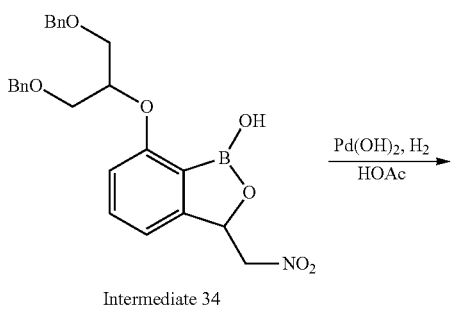

Intermediate 34

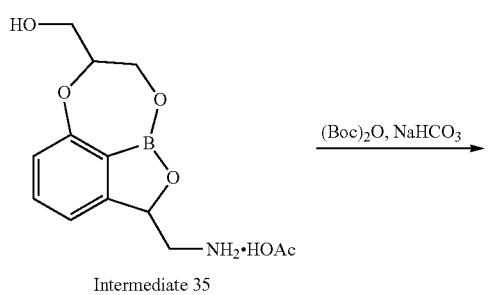

Intermediate 35

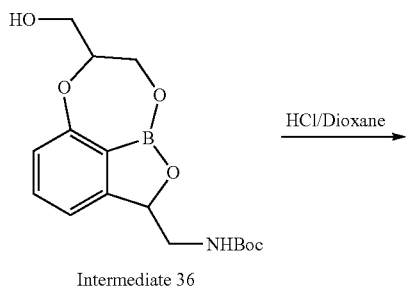

Intermediate 36

-continued

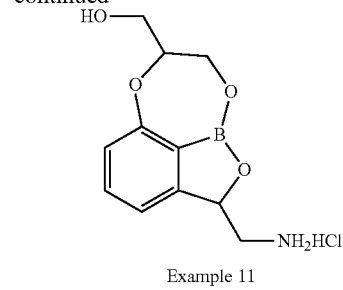

Example 11

Intermediate 31.

MsCl (2.35 ml, 30.40 mmol) was added to a solution of Intermediate 30 (6.9 g, 25.33 mmol), TEA (7.06 ml, 50.66 mmol) in DCM (30 ml) at 0° C. and stirred for 30 min. The mixture was washed with water, and the organic layers were evaporated under vacuum. The crude was taken directly into next step.

Intermediate 32.

$K_2CO_3$ (7 g, 50.66 mmol) was added to a solution Intermediate 31 (9.52 g, 25.33 mmol) and Intermediate 1 (7.64 g, 38 mmol) in DMF (50 ml). The suspension was stirred at 90° C. for 24 h. After the starting bromide was consumed, the mixture was cooled down to r.t., diluted with brine and extracted with EtOAc. EtOAc was removed under vacuum and the residue was purified by silica gel column chromatography (eluent: EtOAc/PE (petroleum ether) 1:20 to 1:15) to afford the Intermediate 32 as a colorless oil.

Intermediate 33.

Intermediate 32 (7.46 g, 16.38 mmol) was mixed with bis(pinacolato)diboron (8.32 g, 32.77 mmol), KOAc (1.74 g, 17.72 mmol), (4.85 g, 49.15 mmol), $PdCl_2$(dppf)DCM (0.365 g, 0.5 mmol), and dissolved in DMF (50 ml). The solution was degassed three times with nitrogen, and then heated at about 90° C. for about 14 h. The reaction was worked up with EtOAc/brine/$H_2O$, and the product was purified by silica gel column chromatography (eluent: EtOAc/PE 1:20 to 1:10) to afford the Intermediate 33 as a brown oil.

Intermediate 34.

To an ice-cold solution of NaOH (0.333 g, 8.32 mmol) in water (10 ml) was added Intermediate 33 (4.18 g, 8.32 mmol) in THF (10 ml). After stirring for 15 min, nitromethane (0.537 ml, 9.98 mmol) was added dropwise, and the mixture was stirred at r.t. for 15 h. The mixture was acidified with AcOH to pH ca. 3-5. The suspension was extracted with EtOAc (3×). The combined organic layer were evaporated under vacuum, and the residue was purified by silica gel column chromatography (eluent: EtOAc/PE 1:4 to 1:1) to afford the Intermediate 34 as a brown oil.

Intermediate 35.

20% Pd(OH)$_2$/C (50% water, 1 g) was added to a solution of Intermediate 34 (1.10 g, 2.37 mmol) in HOAc (8.5 ml). The solution was degassed three times with $H_2$, and stirred at r.t. for overnight. After filterating through celite pad, the filtrate was concentrated under vacuum with toluene to afford the Intermediate 35 as yellow solid. MS (m/z): 236.0 [M+H].

Intermediate 36.

NaHCO$_3$ (298.6 mg, 3.56 mmol) was added to a solution of Intermediate 35 (1.01 g, 2.37 mmol) t-BuOH (3 mL) and H$_2$O (3 mL) at r.t. After stirring at r.t. for 15 min. (Boc)$_2$O (516.7 mg, 2.37 mmol) was added and stirred at r.t. for 1.5 h. The mixture was acidified with AcOH to pH ca. 6-7 and extracted with DCM. Combined organic layers were evaporated under vacuum, and the residue purified by silica gel column chromatography (eluant: DCM/MeOH 20:1) to afford the Intermediate 36 as yellow oil. MS (m/z): 336.0 [M+H].

Compound of Example 11

Intermediate 36 (90.5 mg, 0.27 mmol) was dissolved in 4N HCl in 1,4-dioxane (2 mL), and the solution was stirred at r.t. for about 2 h. The volatiles were removed under vacuum, and the residue was dissolved in water ca. 3 mL) and filtered through 0.45 μM membrane filter. The aq. solution was lyophilized to afford the compound of Example 11. $^1$H NMR: 8.16 (d, J=16.8 Hz, 2H), 7.51 (t, J=7.6 Hz, 1H), 7.15 (dd, J 7.6, 3.6 Hz, 1H), 6.92 (dd, J 8.0, 1.6 Hz, 1H), 5.50 (t, J=9.2 Hz, 1H), 4.46 (d, J=12.4 Hz, 1H), 4.24-4.18 (m, 2H), 3.76 (dd, J 11.6, 4.4 Hz, 1H), 3.62 (dd, J 10.0, 4.8 Hz, 1H), 3.50 (d, J=12.4 Hz, 1H), 3.00-2.88 (m, 1H). MS (m/z): 236.0 [M+H].

Example 12

2-(2-(Aminomethyl)-7,8-dihydro-2H-1,6,9-trioxa-9a-borabenzo[cd]azulen-8-yl)ethanol hydrochloride

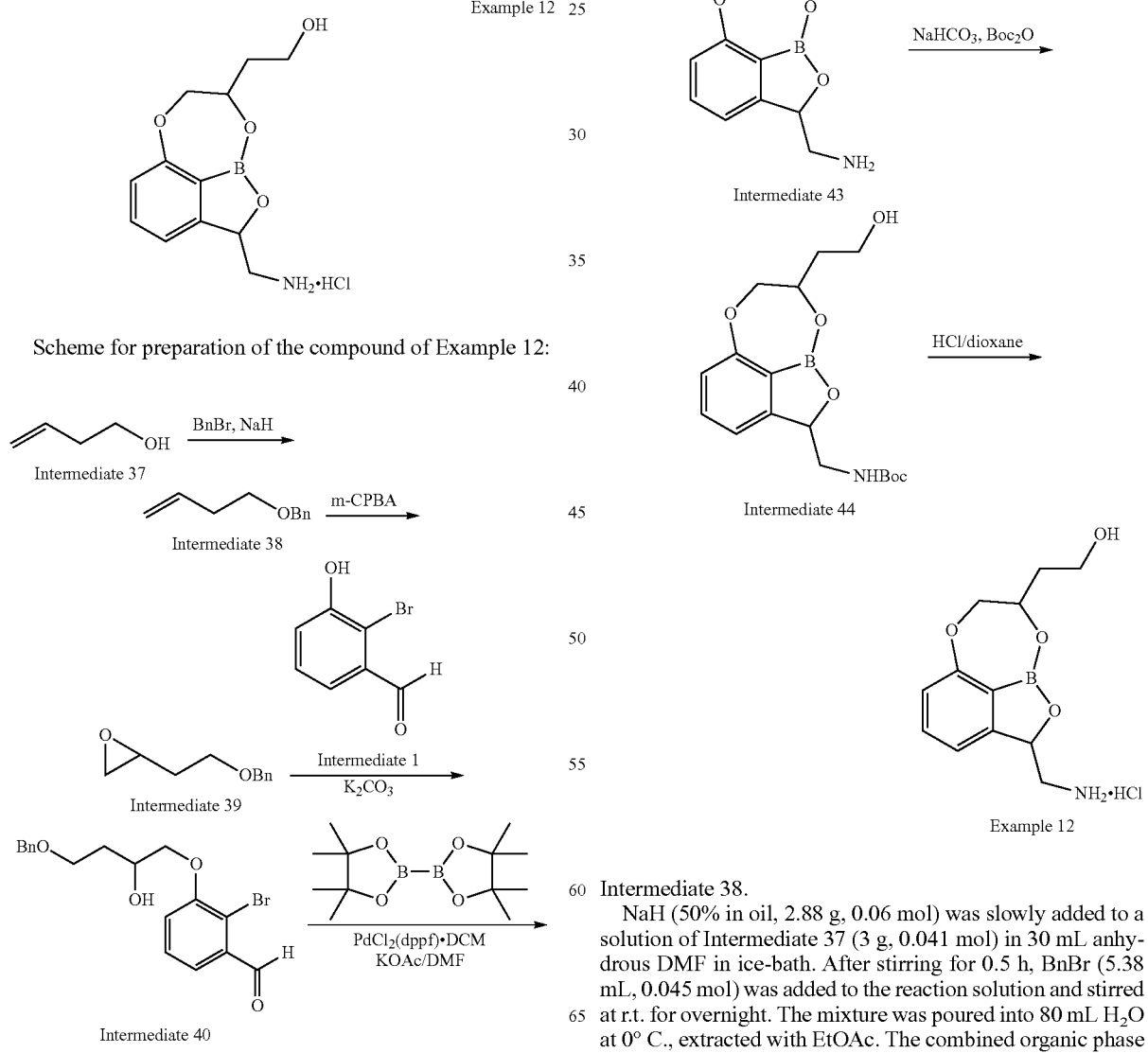

Intermediate 38.

NaH (50% in oil, 2.88 g, 0.06 mol) was slowly added to a solution of Intermediate 37 (3 g, 0.041 mol) in 30 mL anhydrous DMF in ice-bath. After stirring for 0.5 h, BnBr (5.38 mL, 0.045 mol) was added to the reaction solution and stirred at r.t. for overnight. The mixture was poured into 80 mL H$_2$O at 0° C., extracted with EtOAc. The combined organic phase was washed with aq. NH$_4$Cl, brine and dried over Na$_2$SO$_4$.

After concentration, the residue was dissolved in PE (petroleum ether), and filtered through a pad of silica gel. The filtrate was concentrated to afford the Intermediate 38 as colorless oil.

Intermediate 39.

m-Chloroperoxybenzoic acid (m-CPBA, 6.4 g, 0.037 mol) was added to a DCM solution (50 mL) of Intermediate 38 (4 g, 0.025 mol) in portions. The mixture was stirred at r.t. for overnight. The white precipitate was filtered off, and the filtrate was washed with aq $Na_2CO_3$, $H_2O$, brine and dried ($Na_2SO_4$). After concentration, the residue was purified by silica gel column chromatography (eluent: PE/EtOAc 75:1) to afford the Intermediate 39 as yellow oil.

Compound of Example 12

The compound of Example 12 was prepared analogously to the procedures for preparation of the compound of Example 11, except using Intermediate 39 instead of the Intermediate 31 to prepare the Intermediate 40, and then employing respective Intermediates 41-44 in procedures described above for methods with analogous Intermediates 33-36 (employed to prepare the compound of Example 11).
$^1$H NMR ($D_2O$): 7.46 (t, J=7.6 Hz, 1H), 6.98 (d, J=7.2 Hz, 1H), 6.89 (d, J 8.0, 1H), 5.42-5.39 (m, 1H), 4.31-3.81 (m, 3H), 3.53 (m, 2H), 3.55-3.52 (m, 1H), 3.08-3.03 (m, 1H), 1.80-1.70 (m, 2H). MS (m/z): 250.1 [M+H].

Example 13

(2-(Aminomethyl)-8-methyl-7,8-dihydro-2H-1,6,9-trioxa-9a-borabenzo[cd]azulen-8-yl)methanol hydrochloride Example 13

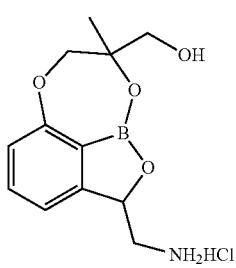

Scheme for preparation of the compound of Example 13:

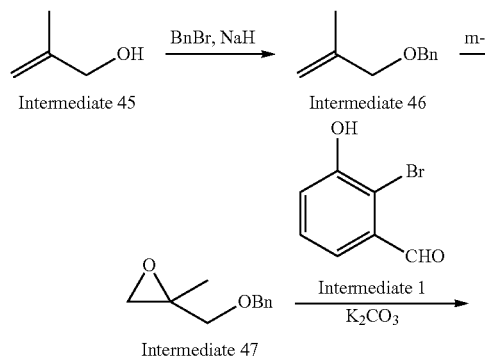

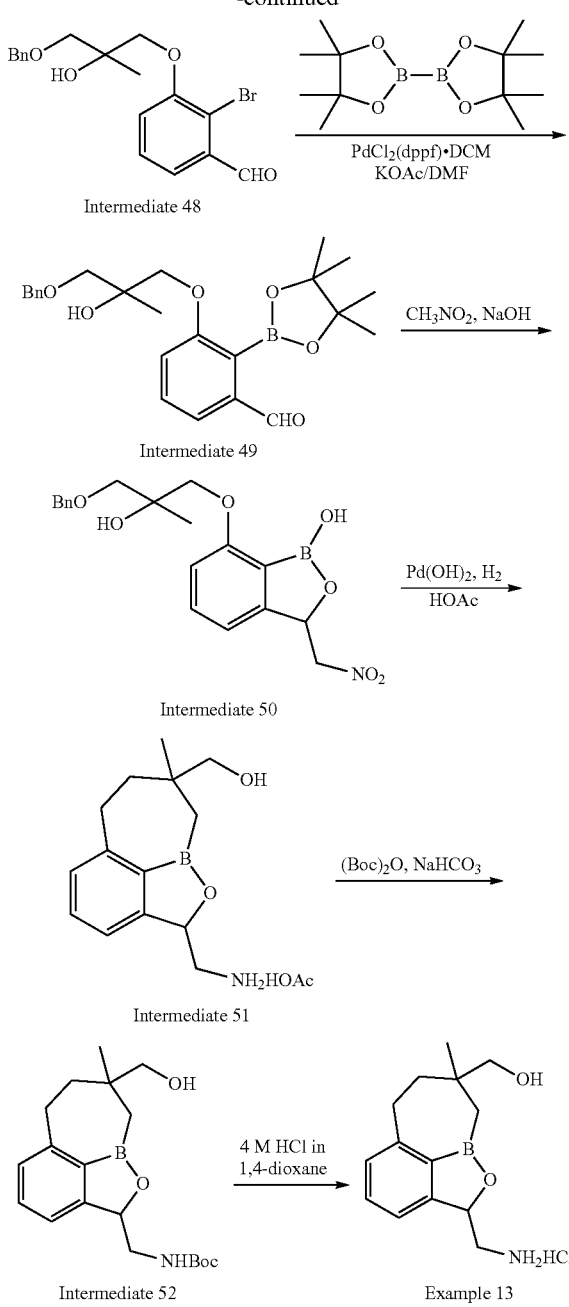

Compound of Example 13

The compound of Example 13 was prepared analogously to the procedures for preparation of the compound of Example 12, except using Intermediate 45 instead of the Intermediate 37 to prepare the Intermediate 46, and then employing respective Intermediates 47-52 in procedures described above for methods with analogous Intermediates 39-44 (employed to prepare the compound of Example 12).
$^1$H NMR ($D_2O$): 7.48 (t, J=8.0 Hz, 1H), 7.01 (d, J=7.6 Hz, 1H), 6.91 (d, J=8.0 Hz, 1H), 5.41 (s, 1H), 3.65 (s, 2H), 3.60-3.54 (m, 3H), 3.06 (dd, J 13.6, 6.8 Hz, 1H), 1.20 (s, 3H). MS (m/z): 250.0 [M+H].

Example 14

1-(2-(Aminomethyl)-7,8-dihydro-2H-1,6,9-trioxa-9a-borabenzo[cd]azulen-8-yl)ethanol hydrochloride

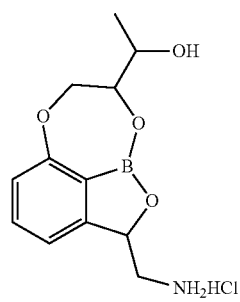

Example 14

Scheme for preparation of the compound of Example 14:

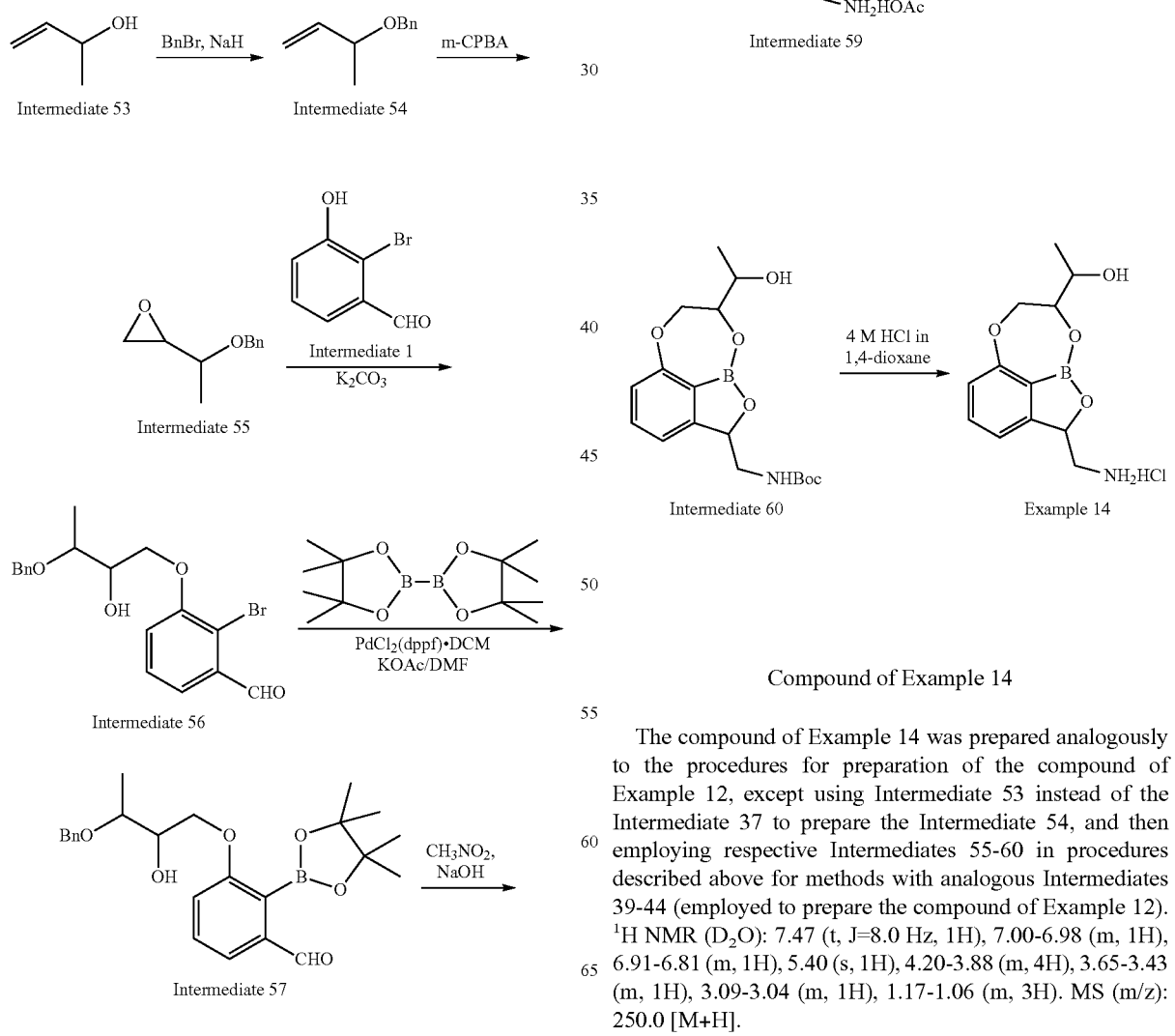

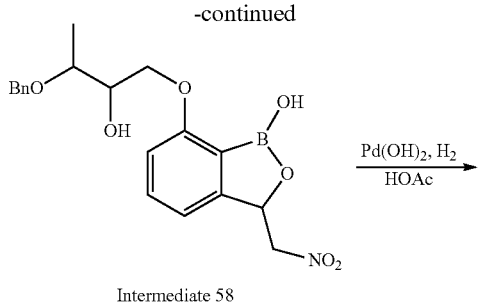

Compound of Example 14

The compound of Example 14 was prepared analogously to the procedures for preparation of the compound of Example 12, except using Intermediate 53 instead of the Intermediate 37 to prepare the Intermediate 54, and then employing respective Intermediates 55-60 in procedures described above for methods with analogous Intermediates 39-44 (employed to prepare the compound of Example 12).
$^1$H NMR (D$_2$O): 7.47 (t, J=8.0 Hz, 1H), 7.00-6.98 (m, 1H), 6.91-6.81 (m, 1H), 5.40 (s, 1H), 4.20-3.88 (m, 4H), 3.65-3.43 (m, 1H), 3.09-3.04 (m, 1H), 1.17-1.06 (m, 3H). MS (m/z): 250.0 [M+H].

Example 15

(2-(Aminomethyl)-7,8-dihydro-2H-1,6,9-trioxa-9a-borabenzo[cd]azulene-8,8-diyl)dimethanol hydrochloride

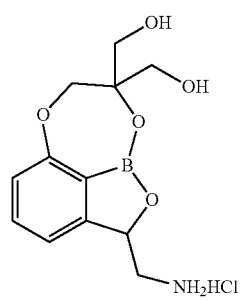

Scheme for preparation of the compound of Example 15:

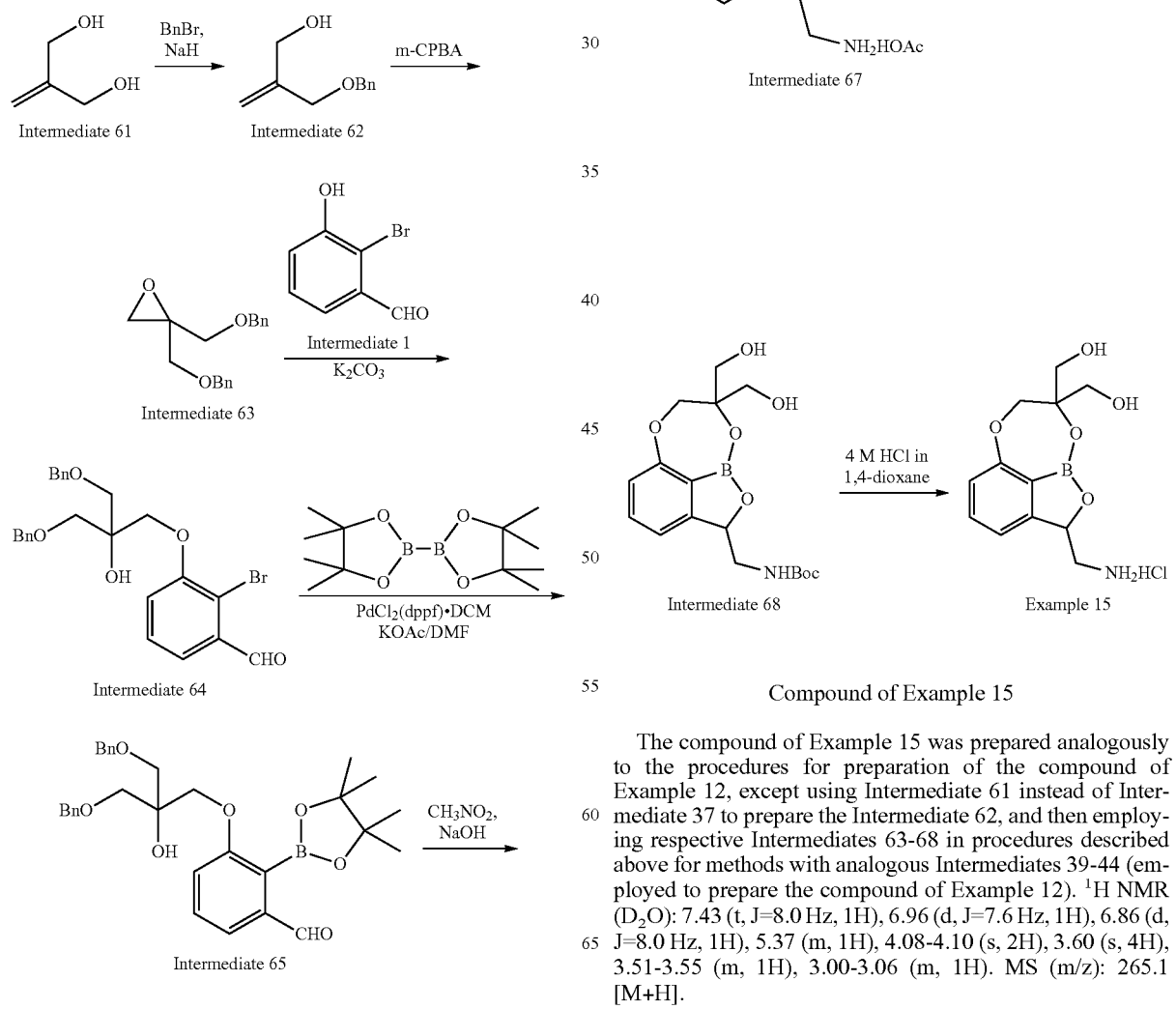

The compound of Example 15 was prepared analogously to the procedures for preparation of the compound of Example 12, except using Intermediate 61 instead of Intermediate 37 to prepare the Intermediate 62, and then employing respective Intermediates 63-68 in procedures described above for methods with analogous Intermediates 39-44 (employed to prepare the compound of Example 12). $^1$H NMR (D$_2$O): 7.43 (t, J=8.0 Hz, 1H), 6.96 (d, J=7.6 Hz, 1H), 6.86 (d, J=8.0 Hz, 1H), 5.37 (m, 1H), 4.08-4.10 (s, 2H), 3.60 (s, 4H), 3.51-3.55 (m, 1H), 3.00-3.06 (m, 1H). MS (m/z): 265.1 [M+H].

Example 16
N-(((8R)-2-(aminomethyl)-7,8-dihydro-2H-1,6,9-trioxa-9a-borabenzo[cd]azulen-8-yl)methyl)formamide hydrochloride
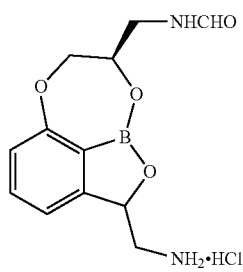
Example 16
Scheme for preparation of the compound of Example 16:
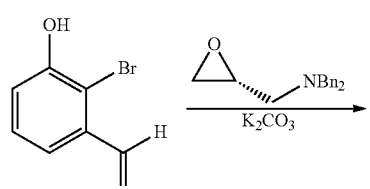
Intermediate 69
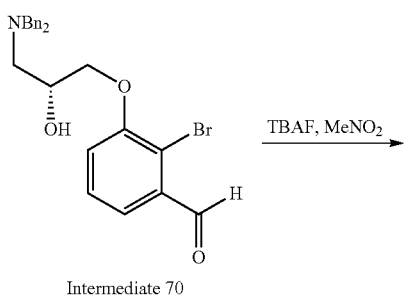
Intermediate 70
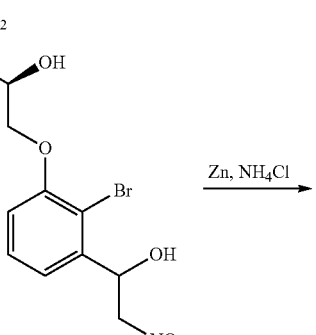
Intermediate 71
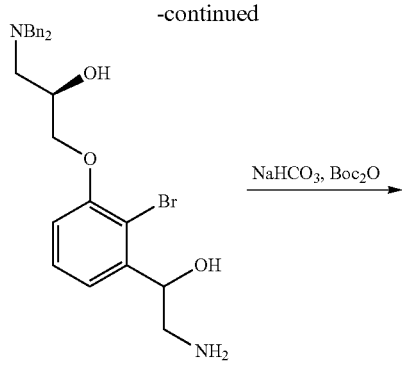
Intermediate 72
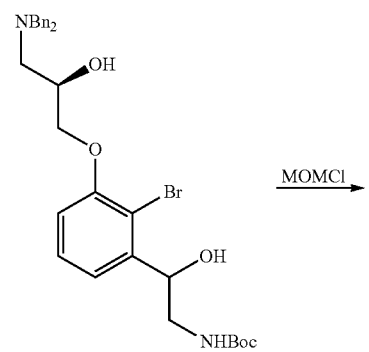
Intermediate 73
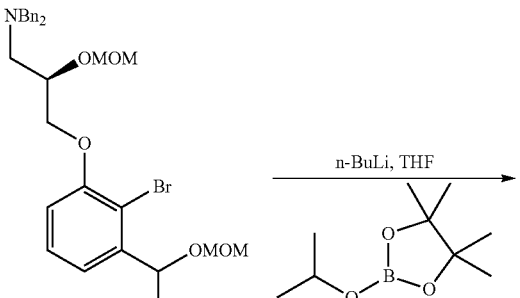
Intermediate 74
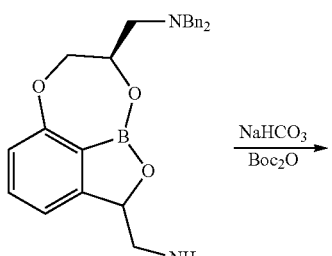
Intermediate 75

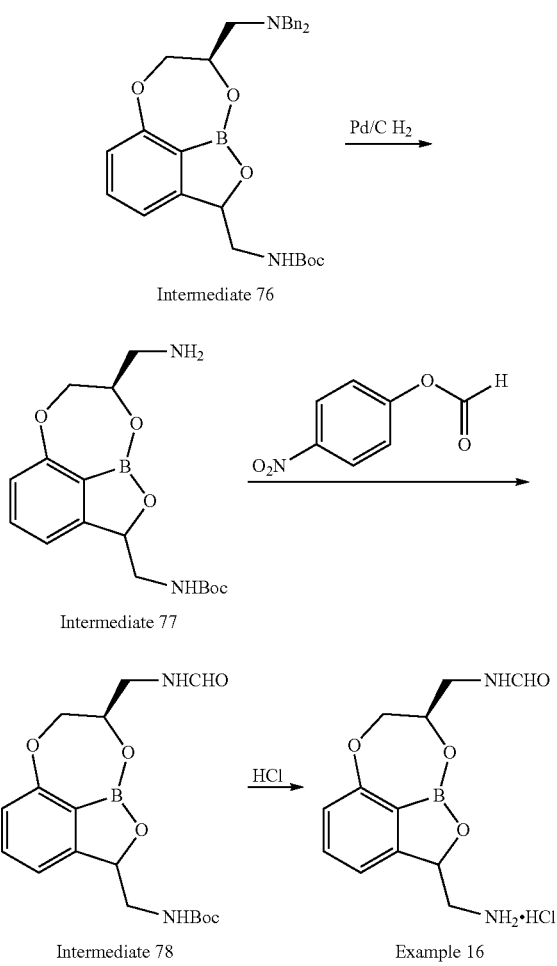

Intermediate 70.

K$_2$CO$_3$ (4.1 g) was added to a solution of Intermediate 69 (4.0 g) and (R)—N,N-dibenzyl-1-(oxiran-2-yl)methanamine (5.0 g; prepared as detailed in the ref. *J. Chem. Soc., Perkin Trans.* 1, 2001, 1086-1090) in DMF (20 mL). The suspension was stirred at 120° C. for 36 h. The mixture was cooled down to r.t., diluted with brine and extracted with EtOAc. EtOAc was removed under vacuum and the residue was taken directly into the next step. MS (m/z): 455.4 [M+H].

Intermediate 71.

1M TBAF in THF (20 mL) was added dropwise to a solution of Intermediate 70 (9.5 g) and MeNO$_2$ (5.6 mL) in THF (100 mL) at 0° C. The mixture was stirred at same temperature for 3 h. The mixture was poured into ice-water (80 mL), extracted with EtOAc. The combined organic phase was washed with brine and concentrated under vacuum. The residue was purified by silica gel column chromatography to afford the Intermediate 71. MS (m/z): 516.4 [M+H].

Intermediate 72.

Zn (6.3 g) was added to a solution of Intermediate 71 (5.0 g) and NH$_4$Cl (5.2 g) in MeOH (80 mL). The suspension was stirred at r.t. for 2 h. After filtration, the filtrate was evaporated under vacuum to afford the Intermediate 72 used at next step without purification. MS (m/z): 486.5 [M+H].

Intermediate 73.

The total amount of Intermediate 72 was dissolved in MeOH (60 mL) and water (20 mL). NaHCO$_3$ (1.3 g) was added, followed by Boc$_2$O (3.3 g). The mixture was stirred at r.t. o.n. The solvent was removed under vacuum, the residue was re-dissolved in water and EtOAc. The organic layer was washed with brine, concentrated under vacuum to afford the Intermediate 73. MS (m/z): 586.5 [M+H].

Intermediate 74.

Methoxymethyl chloride (MOMCl, 5.5 mL) was added dropwise to a solution of Intermediate 73 (5.3 g) and DIEA (11.9 mL) in DCM (50 mL) at 0° C. The mixture was stirred at r.t. o.n. The mixture was washed with H$_2$O and extracted with DCM. The combined organic layer dried and concentrated. The residue was purified by silica gel column chromatography to afford the Intermediate 74. MS (m/z): 674.6 [M+H].

Intermediate 75.

2.5M BuLi in hexanes (0.6 mL) was added dropwise to a solution of Intermediate 74 (202 mg) in THF (1 mL) under Ar at −78° C. After stirring at same temperature for 3 h, 1-isopropoxy-3,3,4,4-tetramethylborolane (468 mg) was added. The mixture was slowly warmed to r.t. and stirred for another 1 h. 8M HCl (1 mL) was added, and the mixture was stirred at r.t. o.n. Volatiles were removed by lyophilization to afford the Intermediate 75. MS (m/z): 415.3 [M+H].

Intermediate 76.

The total amount of the Intermediate 75 from preceding step was dissolved in MeOH (3 mL) and water (2 mL). NaHCO$_3$ (84 mg) was added, followed by Boc$_2$O (131 mg). The mixture was stirred at r.t. o.n. The solvent was removed under vacuum, the residue was re-dissolved in water and EtOAc. The organic larger was washed with brine, concentrated under vacuum. The residue was purified by HPLC to afford the Intermediate 76. MS (m/z): 515.3 [M+H].

Intermediate 77.

A suspension of Intermediate 76 (20 mg) and Pd/C (2 mg) in MeOH (1 mL) was degassed with H$_2$ for three times. The mixture was stirred under H$_2$ at r.t. for 3 h. After filtration, the filtrate was concentrated under vacuum to afford the Intermediate 77. MS (m/z): 334.2 [M+H].

Intermediate 78.

The total of the Intermediate 77 was dissolved in MeOH (1 mL). 4-Nitrophenyl formate (8 mg) was added, and the mixture was stirred r.t. for 6 h. The solvent was removed under vacuum to afford the Intermediate 78. MS (m/z): 362.2 [M+H].

Compound of Example 16

The total amount of Intermediate 78 from preceding step was added to 4M HCl in dioxane (1 mL). The mixture was stirred at r.t. for 2 h. Volatiles were removed under vacuum. The residue was dissolved in water (5 mL) and washed with EtOAc and Et$_2$O. The aqueous phase was lyophilized to afford the compound of Example 16. $^1$H NMR (D$_2$O): 7.99 (s, 1H), 7.47 (dd, J 10.0, 6.0 Hz, 1H), 6.99 (d, J=7.2 Hz, 1H), 6.87 (d, J=8.4 Hz, 1H), 5.39 (s, 1H), 4.12-4.19 (m, 2H), 4.35 (d, J=17.2 Hz, 1H), 3.33-4.48 (m, 2H), 3.20-3.25 (m, 1H), 3.04-3.13 (m, 1H). MS (m/z): 262.2 [M+H].

Example 17
((2S,8S)-8-(Fluoromethyl)-7,8-dihydro-2H-1,6,9-trioxa-9a-borabenzo[cd]azulen-2-yl)methanamine hydrochloride
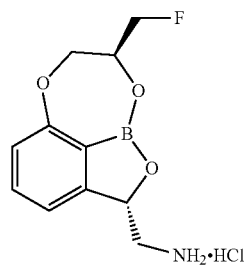
Scheme for preparation of the compound of Example 17:
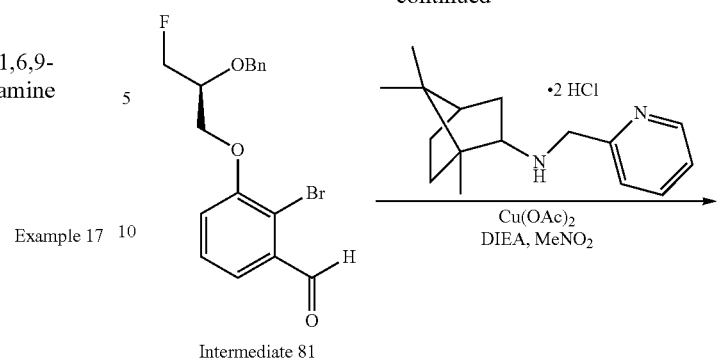
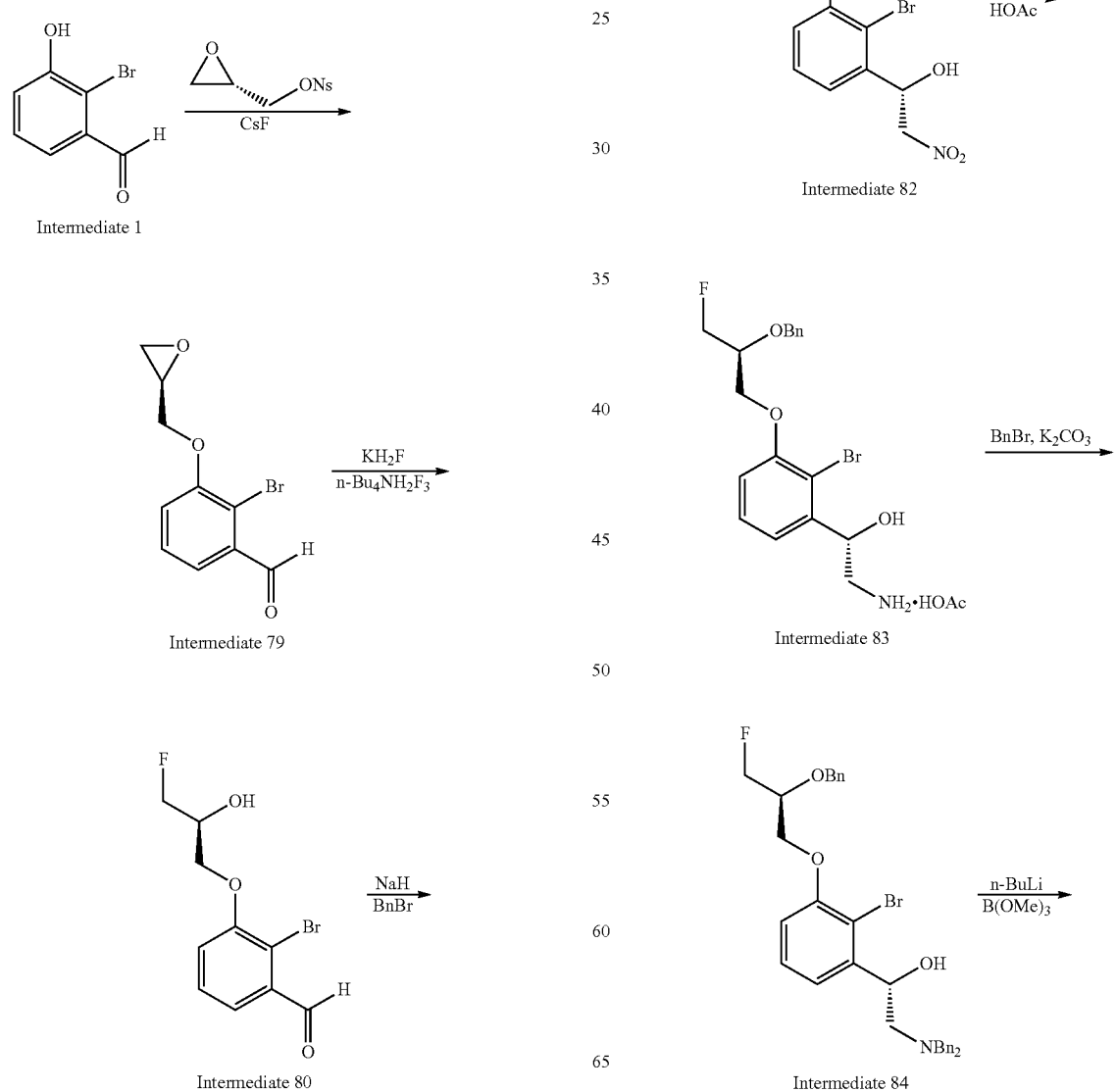

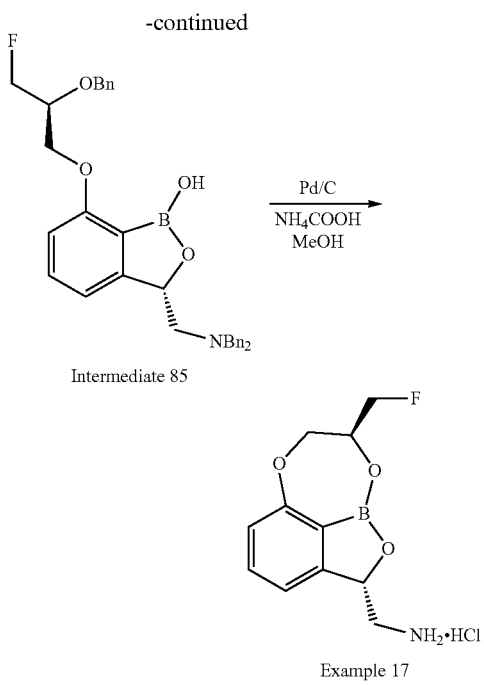

Intermediate 85

Example 17

Intermediate 79.

CsF (27 g) was added to a solution of Intermediate 1 (9.0 g) and (S)-oxiran-2-ylmethyl 3-nitrobenzenesulfonate (23 g) in DMF (150 mL). The mixture was stirred at 80° C. for 40 h. The mixture was poured into ice-$H_2O$ and extracted with EtOAc. The combined organic layers were washed with brine, dried and concentrated under vacuum. The residue was purified by silica gel column chromatography (eluent: PE/EtOAc 6:1) to afford the Intermediate 79.

Intermediate 80.

n-$Bu_4NH_2F_3$ (1.1 g) was added to a solution of Intermediate 79 (3.0 g) in chlorobenzene (6 mL), followed by $KHF_2$ (2.7 g). The mixture was stirred at 135° C. o.n. After cooling to r.t., the mixture was poured into ice-water and extracted with EtOAc. The combined organic layer was dried and concentrated under vacuum. The residue was purified by silica gel column chromatography (eluent: PE/EtOAc 5:2) to afford the Intermediate 80.

Intermediate 81.

NaH (0.38 g) was added to a solution of Intermediate 80 in DMF (20 mL) at 0° C. After stirring for 0.5 h, BnBr (1.03 mL) was added, and the mixture was stirred at r.t. o.n. The mixture was poured into ice-water, extracted with EtOAc. The organic layer was dried and evaporated under vacuum. The residue was purified by silica gel column chromatography (eluent: PE/EtOAc 10:1) to afford the Intermediate 81.

Intermediate 82.

A mixture of $Cu(OAc)_2$ (17.3 mg) and N-((1S,2S,4R)-1,7,7-trimethylbicyclo[2.2.1]heptan-2-yl)pyridin-2-amine dihydrochloride (36.3 mg) in EtOH (6 mL) was stirred at r.t. for 1 h, at which time Intermediate 81 (1.5 g) was added. The reaction mixture was cooled to −40° C. and nitromethane (2.2 mL) was added while maintaining the temperature below −30° C., followed by DIEA (0.7 mL). The mixture was stirred at −30° C. for 48 h. TFA (0.05 mL) was added, followed by water $H_2O$ (50 mL), and EtOAc (50 mL). The aqueous layer was extracted with EtOAc. The organic layer was dried and concentrated under vacuum. The residue was purified by silica gel column chromatography (eluent: PE/EtOAc 8:1) to afford the Intermediate 82.

Intermediate 83.

Zn (1.44 g) was added to a solution of Intermediate 82 (630 mg) in HOAc (7 mL). The suspension was stirred at r.t. for 3 h. After filtration, the filtrate was evaporated to afford the Intermediate 83. MS (m/z): 399.3 [M+H].

Intermediate 84.

The total amount of Intermediate 83 was dissolved in EtOH (10 mL). $K_2CO_3$ (455 mg) was added, followed by BnBr (0.590 mL). The mixture was stirred at r.t. for 24 h. The mixture was diluted with water, extracted with EtOAc. The combined organic layer was dried and concentrated under vacuum. The residue was purified by silica gel column chromatography (eluent: PE/EtOAc 10:1) to afford the Intermediate 84. MS (m/z): 579.5 [M+H].

Intermediate 85.

2.5M BuLi in hexanes (2.6 mL) was added dropwise to a solution of Intermediate 84 (762 mg) in THF (8 mL) under Ar at −78° C. After stirring at same temperature for 3 h, $B(OMe)_3$ (2.1 g) was added. The mixture was allowed to warm up to r.t. and stirred for another 1 h. The mixture was poured into ice-water, extracted with EtOAc. The combined organic layer was dried and concentrated under vacuum to afford the Intermediate 85. MS (m/z): 526.4 [M+H].

Compound of Example 17

To a suspension of Intermediate 85 (1.0 g) and Pd/C (250 mg) in MeOH (15 mL) stirred at 50° C. was added $NH_4COOH$ (2.5 g). The mixture was stirred for 2 h. After filtration, the solvent was removed under vacuum. The residue was purified by HPLC to afford the compound of Example 17. $^1H$ NMR ($D_2O$): 7.49 (t, J=8.0 Hz, 1H), 7.00 (d, J=8.0 Hz, 1H), 6.91 (d, J=8.0 Hz, 1H), 5.39-5.40 (m, 1H), 4.58-4.70 (m, 1H), 4.47-4.54 (m, 1H), 4.11-4.33 (m, 3H), 3.54 (dd, J 13.2, 2.8 Hz, 1H), 3.07 (dd, J 13.2, 2.8 Hz, 1H). MS (m/z): 237.0 [M+H].

Example 18

((2S,8R)-2-(Aminomethyl)-5-fluoro-7,8-dihydro-2H-1,6,9-trioxa-9a-borabenzo[cd]azulen-8-yl)methanol hydrochloride

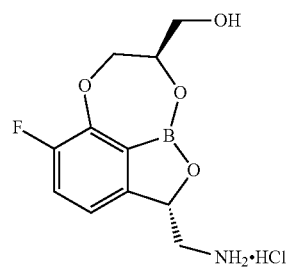

Example 18

Scheme for preparation of the Compound of Example 18:

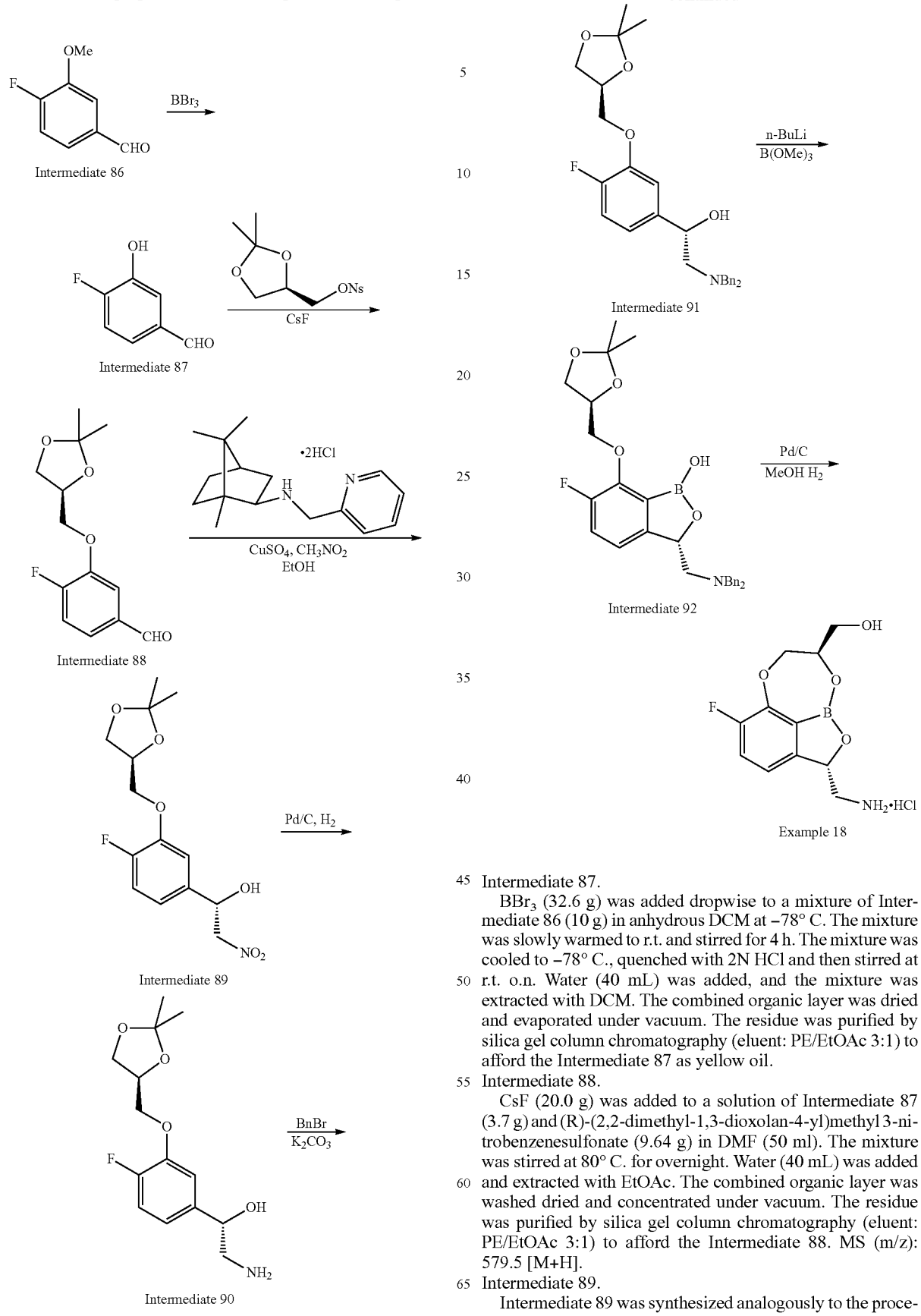

Intermediate 87.

BBr$_3$ (32.6 g) was added dropwise to a mixture of Intermediate 86 (10 g) in anhydrous DCM at −78° C. The mixture was slowly warmed to r.t. and stirred for 4 h. The mixture was cooled to −78° C., quenched with 2N HCl and then stirred at r.t. o.n. Water (40 mL) was added, and the mixture was extracted with DCM. The combined organic layer was dried and evaporated under vacuum. The residue was purified by silica gel column chromatography (eluent: PE/EtOAc 3:1) to afford the Intermediate 87 as yellow oil.

Intermediate 88.

CsF (20.0 g) was added to a solution of Intermediate 87 (3.7 g) and (R)-(2,2-dimethyl-1,3-dioxolan-4-yl)methyl 3-nitrobenzenesulfonate (9.64 g) in DMF (50 ml). The mixture was stirred at 80° C. for overnight. Water (40 mL) was added and extracted with EtOAc. The combined organic layer was washed dried and concentrated under vacuum. The residue was purified by silica gel column chromatography (eluent: PE/EtOAc 3:1) to afford the Intermediate 88. MS (m/z): 579.5 [M+H].

Intermediate 89.

Intermediate 89 was synthesized analogously to the procedure for preparation of the Intermediate 82, except starting from Intermediate 88 instead of Intermediate 81. The residue was purified by silica gel column chromatography (eluent: PE/EtOAc 5:1) to afford the Intermediate 89 as yellow oil.

Intermediate 90.

A suspension of Intermediate 89 (1.0 g) and Pd/C in MeOH (2 ml) was stirred under H$_2$ atmosphere overnight. After filtration, the filtrate was concentrated under vacuum to afford the Intermediate 90. MS (m/z): 286.3 [M+H].

Intermediate 91.

K$_2$CO$_3$ (242 mg) was added to a solution of Intermediate 90 (250 mg) in EtOH, followed by BnBr (450 mg). The mixture was stirred at r.t. o.n. Water (40 mL) was added and the mixture was extracted with EtOAc. The combined organic layer was dried and concentrated under vacuum. The residue was purified by silica gel column chromatography (eluent: PE/EtOAc 1:1) to afford the Intermediate 91 as yellow oil. MS (m/z): 466.6 [M+H].

Intermediate 92.

2.5M BuLi (0.36) was added dropwise to a solution of Intermediate 91 (52 mg) in anhydrous toluene at −70° C. The mixture was slowly warmed up to 0° C. and stirred for 2 h. The mixture was cooled to −70° C., then B(OMe)$_3$ (58.1 mg, 0.56 mmol) was added, and the mixture was stirred at 0° C. for 1 h. Water (10 mL) was added and the mixture was extracted with EtOAc. The combined organic layer was dried and concentrated under vacuum. The residue was purified by HPLC to afford the Intermediate 92 as yellow oil. MS (m/z): 492.4 [M+H].

Compound of Example 18

Concentrated HCl (1 mL) was added to a suspension of Intermediate 92 (35 mg) and Pd/C in MeOH. The mixture was stirred under H$_2$ for 2 h. The mixture was filtered and the solvent removed under vacuum. The residue was dissolved in MeOH and was purified by HPLC to afford the compound of Example 18 as a white solid. $^1$H NMR (D$_2$O): 7.30-7.25 (m, 1H), 7.02-6.99 (m, 1H), 5.47-5.46 (m, 1H), 4.44-4.33 (m, 3H), 3.74-3.53 (m, 3H), 3.13-3.08 (m, 1H). MS (m/z): 254.0 [M+H].

Example 19

((2S,8R)-2-(Aminomethyl)-3-fluoro-7,8-dihydro-2H-1,6,9-trioxa-9a-borabenzo[cd]azulen-8-yl)methanol hydrochloride

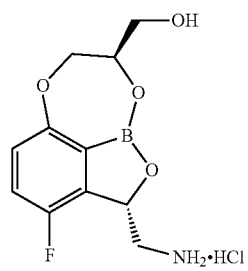

Example 19

Scheme for preparation of the compound of Example 19:

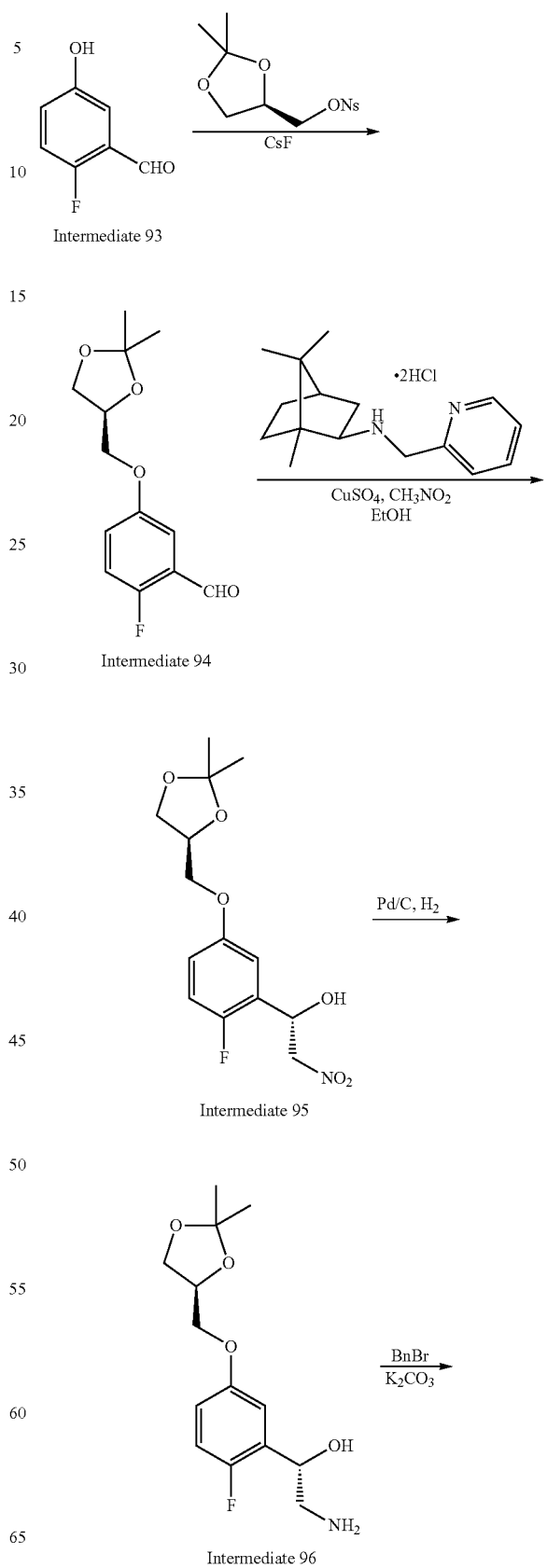

59
-continued

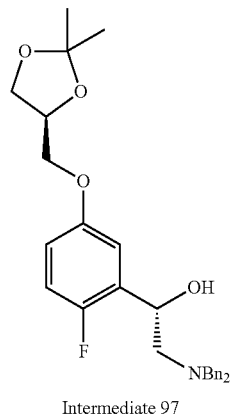
Intermediate 97

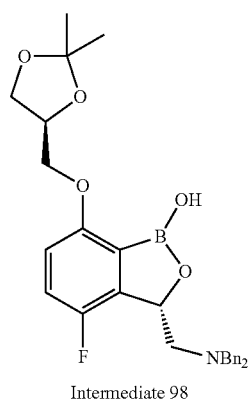
Intermediate 98

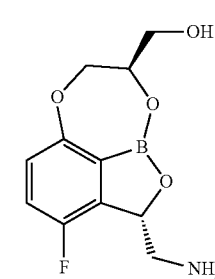
Example 19

Compound of Example 19

The compound of Example 19 was prepared analogously to the procedures for preparation of the compound of Example 18, except using Intermediate 93 instead of the Intermediate 87 to prepare the Intermediate 94, and then employing respective Intermediates 95-98 in procedures described above for methods with analogous Intermediates 89-92 (employed to prepare the compound of Example 18). ¹H NMR (D₂O): 7.10-7.08 (m, 1H), 6.87-6.86 (m, 1H), 5.48-5.47 (m, 1H), 5.15-5.06 (m, 3H), 3.67-3.53 (m, 3H), 3.17-3.12 (m, 1H). MS (m/z): 254.1 [M+H].

60

Example 20

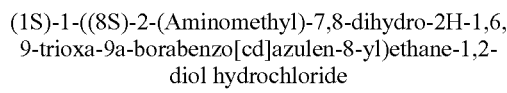

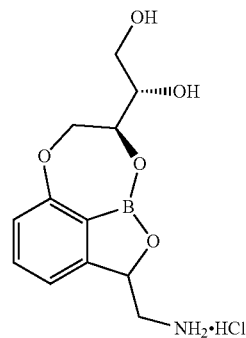

Example 20

Scheme for preparation of the compound of Example 20:

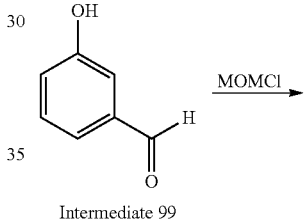
Intermediate 99

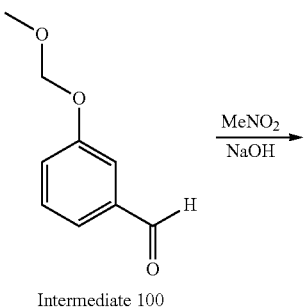
Intermediate 100

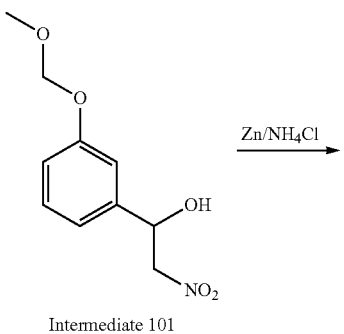
Intermediate 101

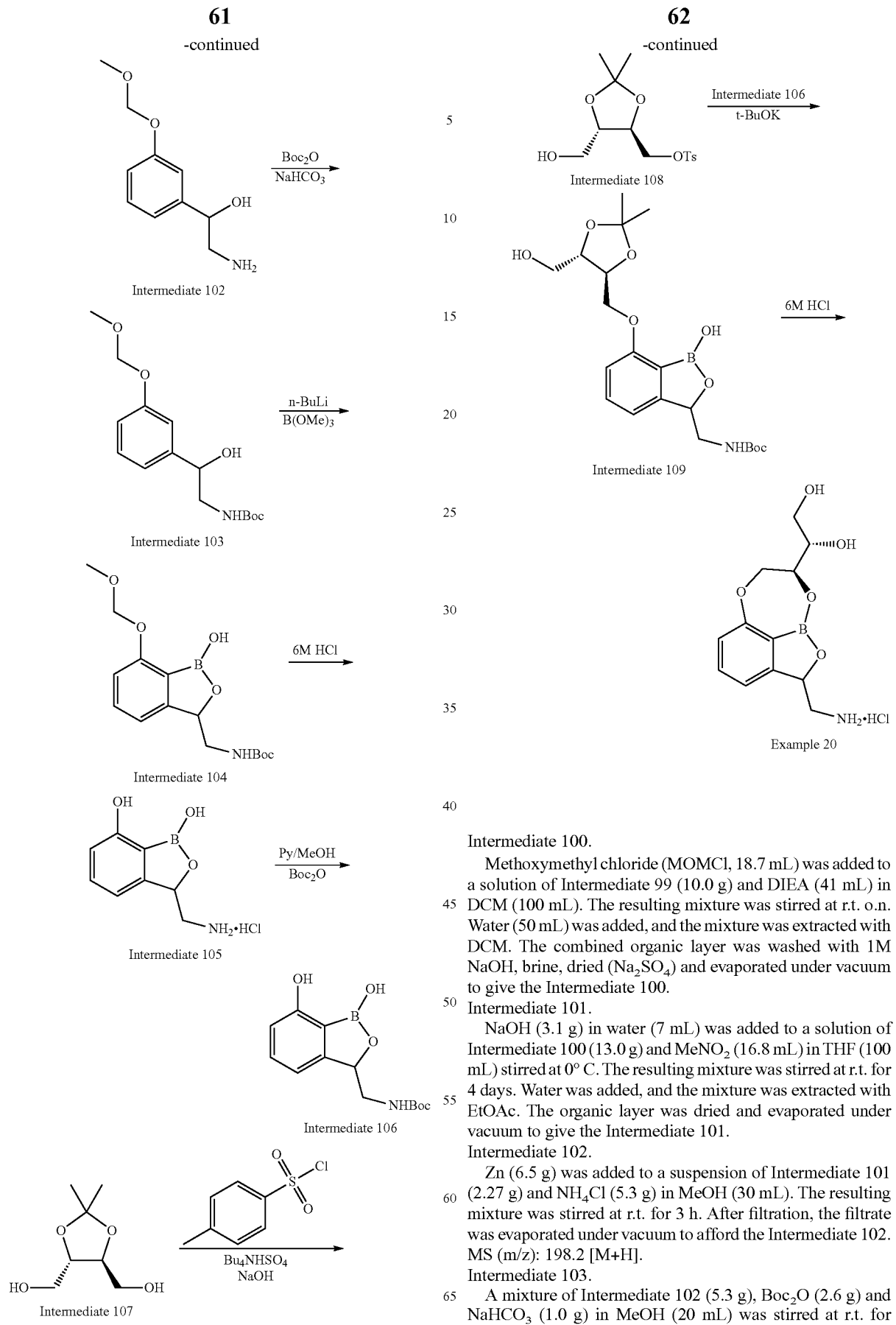

Intermediate 100.

Methoxymethyl chloride (MOMCl, 18.7 mL) was added to a solution of Intermediate 99 (10.0 g) and DIEA (41 mL) in DCM (100 mL). The resulting mixture was stirred at r.t. o.n. Water (50 mL) was added, and the mixture was extracted with DCM. The combined organic layer was washed with 1M NaOH, brine, dried ($Na_2SO_4$) and evaporated under vacuum to give the Intermediate 100.

Intermediate 101.

NaOH (3.1 g) in water (7 mL) was added to a solution of Intermediate 100 (13.0 g) and $MeNO_2$ (16.8 mL) in THF (100 mL) stirred at 0° C. The resulting mixture was stirred at r.t. for 4 days. Water was added, and the mixture was extracted with EtOAc. The organic layer was dried and evaporated under vacuum to give the Intermediate 101.

Intermediate 102.

Zn (6.5 g) was added to a suspension of Intermediate 101 (2.27 g) and $NH_4Cl$ (5.3 g) in MeOH (30 mL). The resulting mixture was stirred at r.t. for 3 h. After filtration, the filtrate was evaporated under vacuum to afford the Intermediate 102. MS (m/z): 198.2 [M+H].

Intermediate 103.

A mixture of Intermediate 102 (5.3 g), $Boc_2O$ (2.6 g) and $NaHCO_3$ (1.0 g) in MeOH (20 mL) was stirred at r.t. for overnight. Water was added, and the mixture was acted with EtOAc. The organic layer was dried (Na sulfate) and evaporated under vacuum. The residue was purified by silica gel column chromatography (eluent: PE/EtOAc) to afford the Intermediate 103. MS (m/z): 298.3 [M+H].

Intermediate 104.

2.5M BuLi in hexanes (11.3 mL) was added dropwise to a solution of Intermediate 103 (2.1 g) in anhydrous toluene (30 mL) at −70° C. The mixture was slowly warmed to 0° C. and stirred for 2 h. The mixture was cooled to −70° C., and then B(OMe)$_3$ (4.4 g) was added, and the mixture was stirred at 0° C. for 2 h. Water was added, and the mixture was extracted with EtOAc. The organic layer was dried (Na sulfate) and evaporated under vacuum. The residue was purified by silica gel column chromatography to afford the Intermediate 104 as yellow oil. MS (m/z): 324.1 [M+H].

Intermediate 105.

6M HCl (1 mL) was added was added to a solution of Intermediate 104 (38 mg) in MeOH (1 mL). The resulting mixture was stirred at r.t. for 2 h. Volatiles were removed under vacuum to afford the Intermediate 105. MS (m/z): 180.0 [M+H].

Intermediate 106.

A mixture of Intermediate 105 (40 mg), Boc$_2$O (44 mg) and pyridine (0.3 mL) in MeOH (2 mL) was stirred at r.t. for overnight. The solvent was removed under vacuum. The residue was treated with water and EtOAc. The organic layer was dried (Na sulfate) and evaporated under vacuum. The residue was purified by preparative TLC to afford the Intermediate 106. MS (m/z): 280.1 [M+H].

Intermediate 108.

Tosyl chloride (259 mg) was added to a solution of Intermediate 107 (200 mg), Bu$_4$NHSO$_4$ (42 mg, 0.123 mmol) and 15% aqueous NaOH (1.35 mmol). The resulting solution was stirred at r.t. for 2 h. Water was added and the mixture was extracted with DCM. The combined organic layers was dried and concentrated. The residue was purified by silica gel column chromatography (eluent: PE/EtOAc 2:1) to afford the Intermediate 109 as yellow oil.

Intermediate 109.

t-BuOK (45 mg) was added to a solution of Intermediate 106 (100 mg) in DMSO (1 mL) at 0° C., followed by addition of the Intermediate 108 (125 mg). The resulting mixture was stirred for 3 h, then filtered and evaporated under vacuum. Resulted crude product was purified by HPLC to afford the Intermediate 109 as a white solid. MS (m/z): 424.3 [M+H].

Compound of Example 20

A solution of Intermediate 109 (13 mg) in 4M HCl in dioxane (1 mL) was stirred for 2 h. Volatiles were removed by lyophilization to afford the compound of Example 20 as a white solid. $^1$H NMR (D$_2$O): 7.41 (s, 1H), 6.95-6.85 (m, 2H), 5.36-5.35 (m, 1H), 4.17-4.05 (m, 3H), 3.58-3.44 (m, 4H), 3.04-3.03 (m, 1H). MS (m/z): 266.1 [M+H].

Example 21

((8S)-2-(Aminomethyl)-7,8-dihydro-2H-1,6,9-trioxa-9a-borabenzo[cd]azulen-8-yl)methyl acetate hydrochloride

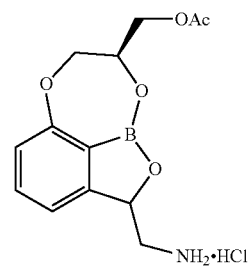

Example 21

Scheme for preparation of the compound of Example 21:

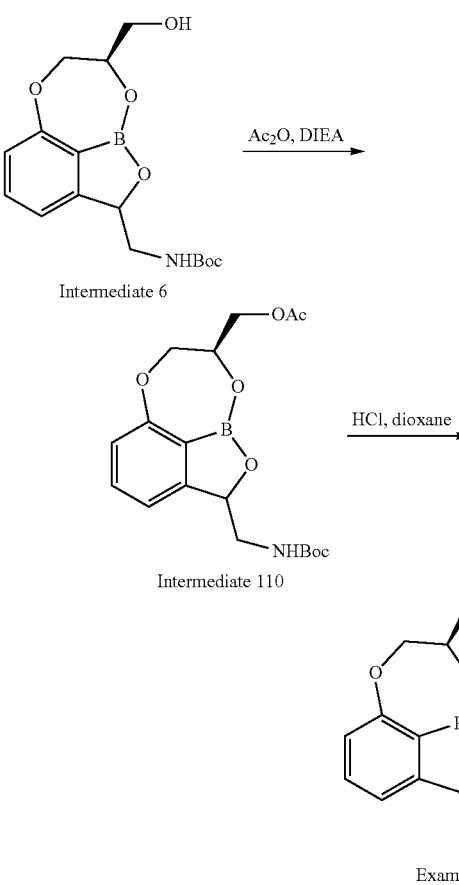

Intermediate 110.

Acetic anhydride (32 µL) was added to a solution of the Intermediate 6 (60 mg) and pyridine (31 µL) in DCM (2 mL) at 0° C. The resulting mixture was stirred at r.t. for 2 h. The solvent was removed under vacuum and the residue purified by HPLC to afford the Intermediate 10. MS (m/z): 378.2 [M+H].

Compound of Example 21

The total amount of Intermediate 110 from preceding step was dissolved in 4M HCl in dioxane (1 mL). The mixture was stirred at r.t. for 1 h. Volatiles were removed by lyophilization to afford the compound of Example 21 as a light-yellow solid. $^1$H NMR (D$_2$O): 7.48 (t, J=8.0 Hz, 1H), 7.00 (d, J=7.6 Hz, 1H), 6.90 (d, J=8.4 Hz, 1H), 5.40 (s, 1H), 4.30-4.12 (m, 5H), 3.73-3.53 (m, 3H), 3.09-3.04 (m, 1H), 1.99 (s, 3H). MS (m/z): 278.1 [M+H].

Example 22

(2S)-4-((3-(Aminomethyl)-1-hydroxy-1,3-dihydrobenzo[c][1,2]oxaborol-7-yl)oxy)butane-1,2-diol hydrochloride

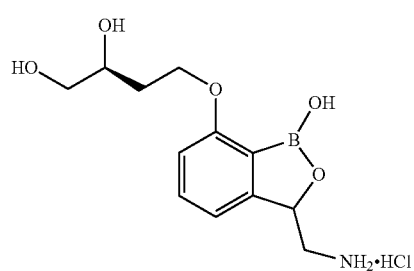

Example 22

Scheme for preparation of the reference compound of Example 22:

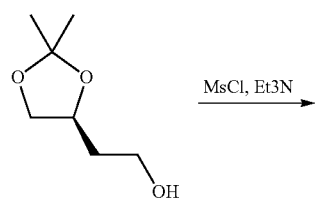

Intermediate 111

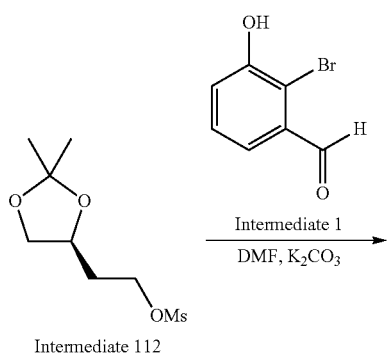

Intermediate 112

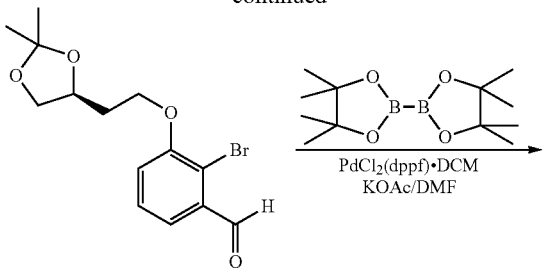

Intermediate 113

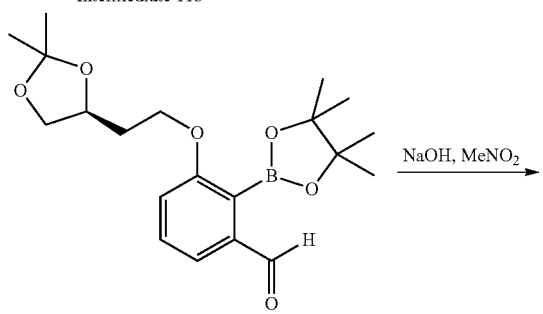

Intermediate 114

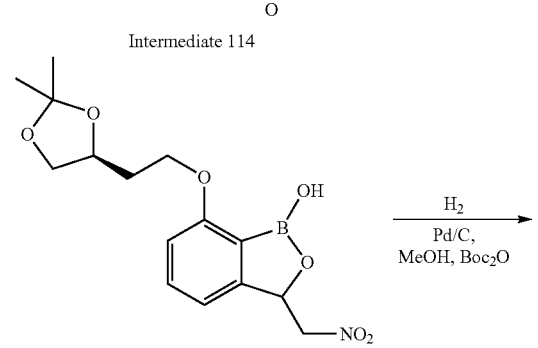

Intermediate 115

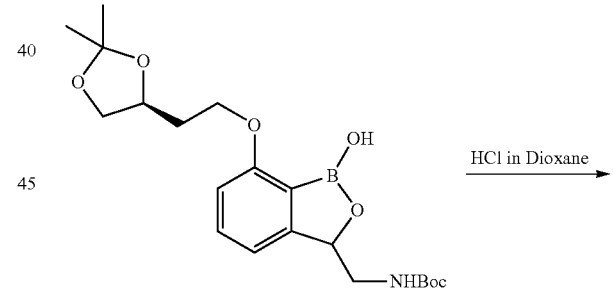

Intermediate 116

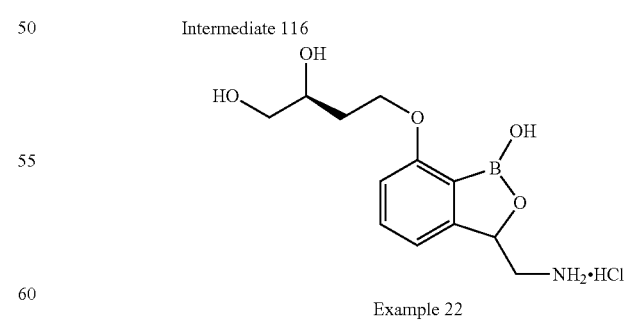

Example 22

Intermediate 115.

The Intermediate 115 was prepared analogously to the procedures for preparation of the compound of Example 11, except using Intermediate 111 instead of Intermediate 30 to prepare the Intermediate 112, and then employing respective Intermediates 113-115 in procedures described above for methods with analogous Intermediates 32-34 (employed to prepare the compound of Example 11).

Intermediate 116.

A mixture of Intermediate 115 (1.4 g), Boc$_2$O (0.5 g) and Pd/C (0.2 g) in MeOH (15 mL) was stirred under H$_2$ at r.t. o.n. After filtration, the solvent was removed under vacuum. The residue was purified by HPLC to afford the Intermediate 116. MS (m/z): 408.3 [M+H].

Compound of Example 22

Intermediate 116 (100 mg) was dissolved in 4M HCl in dioxane (1 mL). The mixture was stirred at r.t. for 1 h. Volatiles were removed by lyophilization to afford the reference compound of Example 22 as light-yellow solid. $^1$H NMR (D$_2$O): 7.39 (t, J=8.0 Hz, 1H); 6.88 (d, J=7.6 Hz, 1H); 6.82 (d, J=8.4 Hz, 1H); 5.37 (d, J=9.2 Hz, 1H); 4.08 (s, 2H); 3.7-3.82 (m, 2H); 3.38-3.59 (m, 2H), 3.38-3.59 (m, 1H), 1.17-1.91 (m, 2H). MS (m/z): 268.1 [M+H].

Example 23

2-(((3-(Aminomethyl)-1-hydroxy-1,3-dihydrobenzo[c][1,2]oxaborol-7-yl)oxy)methyl)propane-1,3-diol hydrochloride

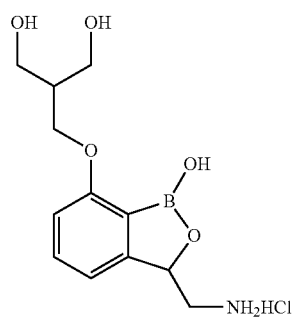

Example 23

Scheme for preparation of the reference compound of Example 23:

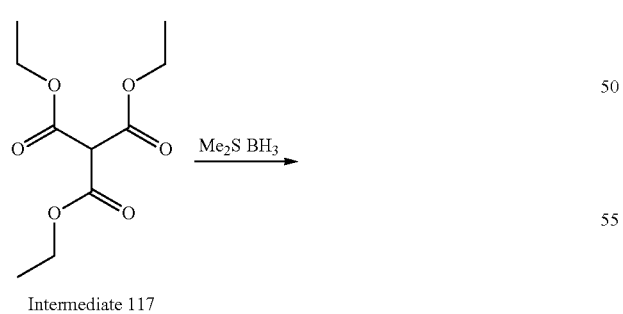

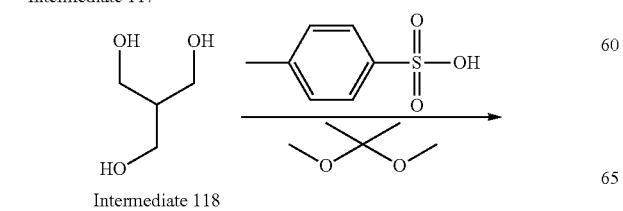

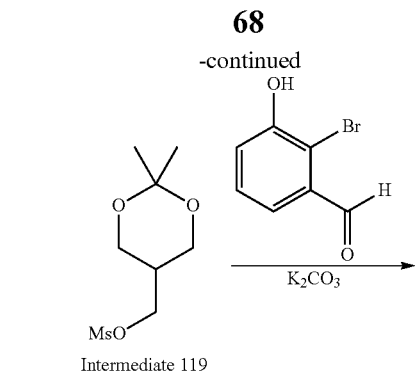

Intermediate 119

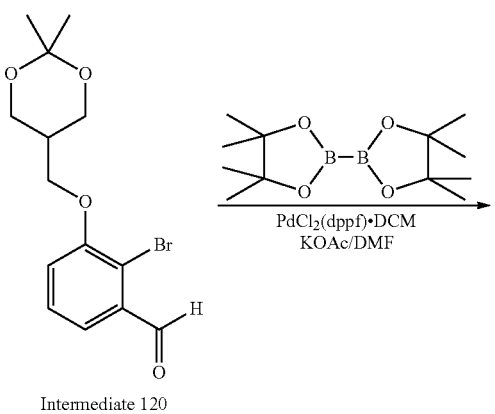

Intermediate 120

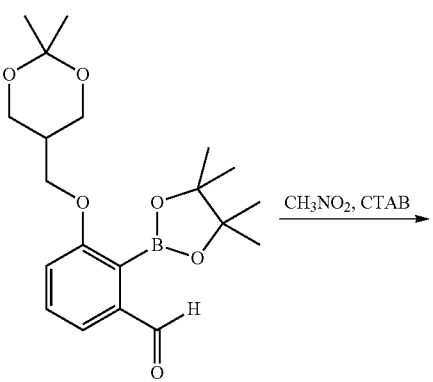

Intermediate 121

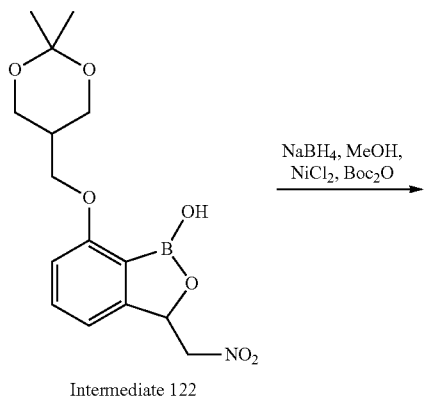

Intermediate 122

-continued

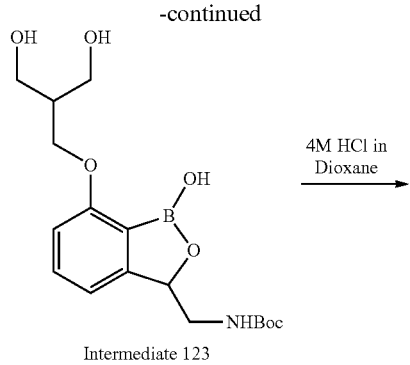
Intermediate 123

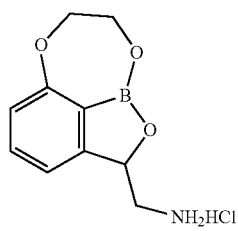
Example 23

Compound of Example 23

The reference compound of Example 23 was prepared analogously to the procedures described in the PCT WO2008/157726. $^1$H NMR (D$_2$O): 8.33 (m, 1H), 7.39 (t, J=7.2 Hz, 1H), 6.90 (dd, J 13.6, 7.6 Hz, 2H), 5.26 (s, 1H), 4.11 (d, J=6.0 Hz, 2H), 3.65 (dd, J 5.6, 2.8 Hz, 4H), 3.45 (d, J=13.6 Hz, 1H), 3.23 (s, 1H), 3.05 (dd, J 13.2, 6.4 Hz, 1H), 2.13-2.17 (m, 1H). MS (m/z): 268.1 [M+H].

Example 24

(7,8-Dihydro-2H-1,6,9-trioxa-9a-borabenzo[cd]azulen-2-yl)methanamine hydrochloride Example 24

Scheme for preparation of the reference compound of Example 24:

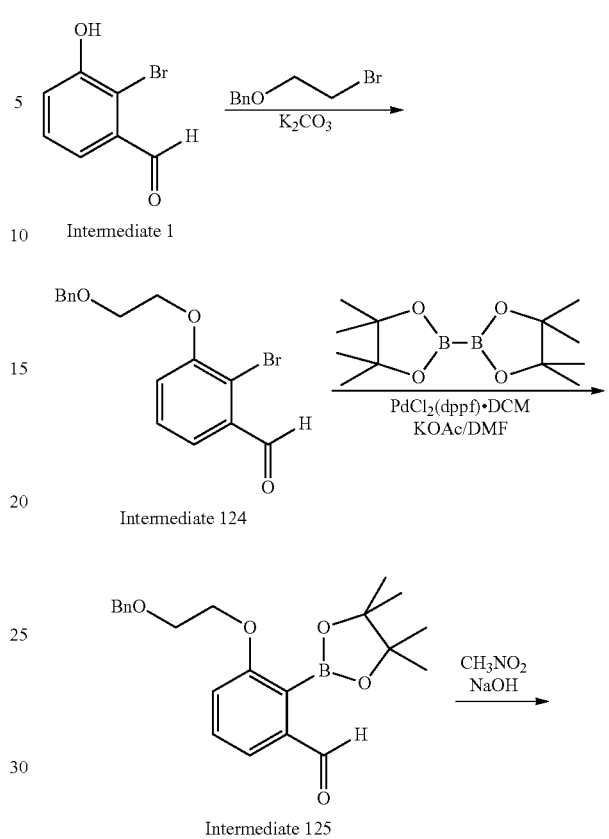
Intermediate 1

Intermediate 124

Intermediate 125

Intermediate 126

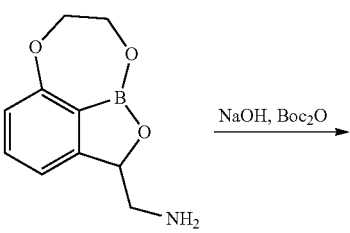
Intermediate 127

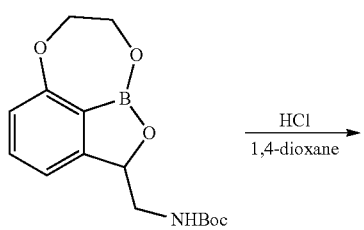
Intermediate 128

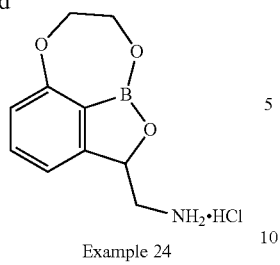

Example 24

Compound of Example 24

The reference compound of Example 24 was prepared analogously to the procedures described in the PCT WO 2008/157726. $^1$H NMR: 8.39 (s, 3H), 7.50 (t, J=7.8 Hz, 1H), 7.15 (d, J=7.2 Hz, 1H), 6.91 (d, J=8.4 Hz, 1H), 5.55-5.48 (m, 1H), 4.73-4.68 (m, 1H), 4.50-4.18 (m, 3H), 3.57-3.51 (m, 1H), 2.94-2.84 (m, 1H). MS (m/z): 206.0 [M+H].

Example 25

(S)-3-(Aminomethyl)-7-(3-hydroxypropoxy)benzo[c][1,2]oxaborol-1(3H)-ol hydrochloride

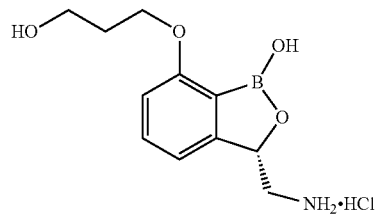

Example 25

Scheme for preparation of the compound of Example 25:

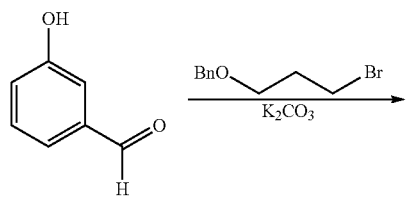

Intermediate 129

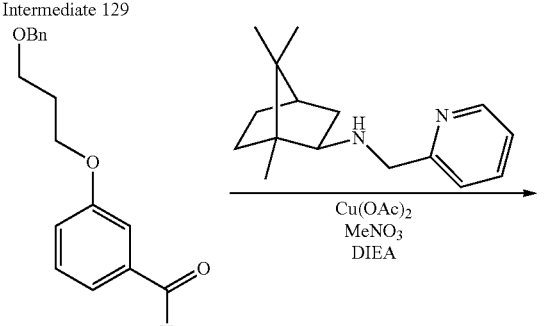

Intermediate 130

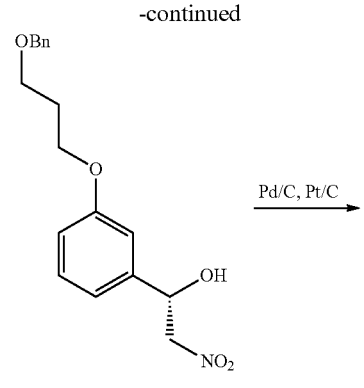

Intermediate 131

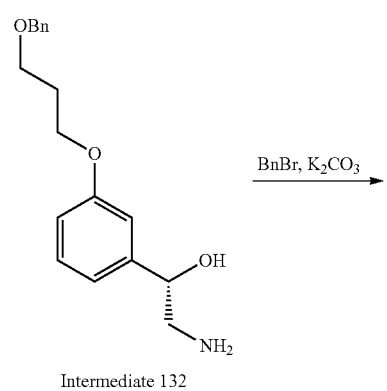

Intermediate 132

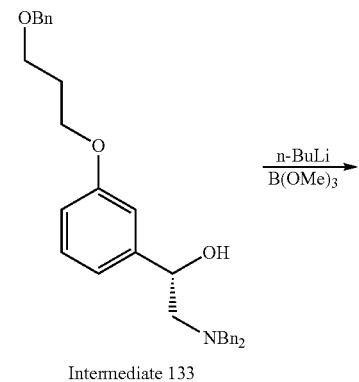

Intermediate 133

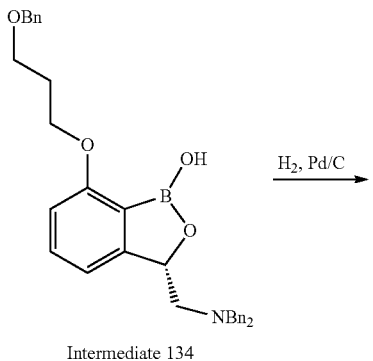

Intermediate 134

-continued

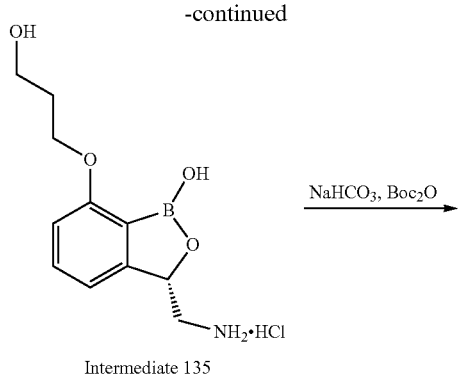

Intermediate 135

↓ NaHCO₃, Boc₂O

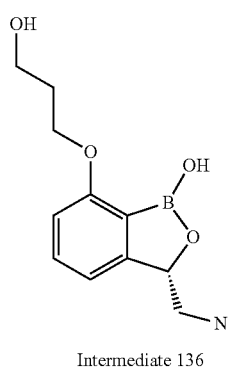

Intermediate 136

↓ HCl/dioxane

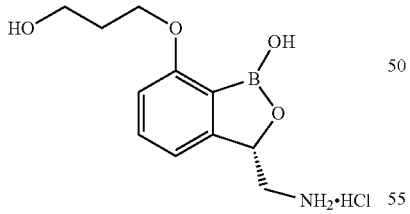

Example 25

Compound of Example 25

The reference compound of Example 25 was prepared analogously to the procedures described in the PCT WO 2011/127143. ¹H NMR (D₂O): 7.53 (t, J=8.0 Hz, 1H), 7.01 (d, J=8.0 Hz, 2H), 5.39 (d, J=6.8 Hz, 1H), 4.18-4.21 (m, 2H), 3.74 (t, J=6.0 Hz, 2H), 3.57 (dd, J 13.2, 2.8 Hz, 1H), 3.08-3.12 (m, 1H), 1.97-2.03 (m, 2H). MS (m/z): 238.1 [M+H].

Example 26

((8S)-2-(Aminomethyl)-7,8-dihydro-2H-1,6,9-tri-oxa-9a-borabenzo[cd]azulen-8-yl)methyl propionate hydrochloride

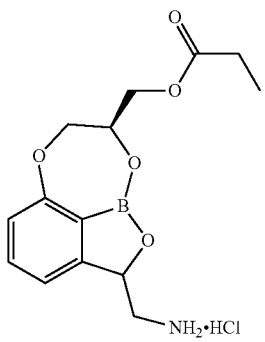

Example 26

Scheme for preparation of the Compound of Example 26:

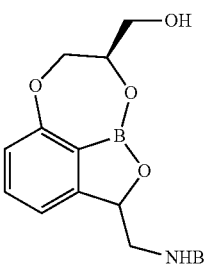

Intermediate 6

↓ Ac₂O, DIEA

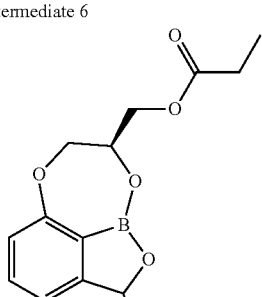

Intermediate 137

↓ HCl, dioxane

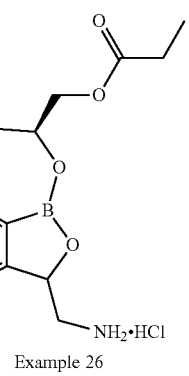

Example 26

Compound of Example 26

The compound of Example 26 was prepared analogously to the procedures described for preparation of the compound of Example 21, except using propionic anhydride instead of acetic anhydride to prepare respective Intermediate 137. Light-yellow solid. $^1$H NMR (D$_2$O): 7.41 (d, J=8.0 Hz, 1H); 6.96-6.84 (m, 2H); 5.32 (s, 1H); 4.27-4.09 (m, 5H); 3.51-3.48 (m, 1H); 3.09-3.04 (m, 1H); 2.30-2.29 (m, 2H); 0.98-0.95 (m, 3H). MS (m/z): 292 [M+H].

Example 27

((2S)-2-(Aminomethyl)-7,8-dihydro-2H-1,6,9-trioxa-9a-borabenzo[cd]azulen-8-yl)methanol hydrochloride

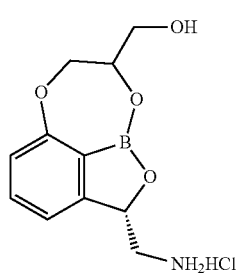

Example 27

Compound of Example 27

The compound of Example 24 is made using procedures described above for the preparation of the compound of Example 3 except using benzyl glycidyl ether instead of benzyl (R)-glycidyl ether.

Utility and Testing

The compounds provided herein exhibit potent activities against a variety of microorganisms, including Gram-positive and Gram-negative microorganisms. Accordingly, the compounds provided herein have broad antibacterial activity. Thus, the compounds provided herein are useful antimicrobial agents and may be effective against a number of human and veterinary pathogens, including Gram-positive aerobic bacteria such as multiply-resistant staphylococci and streptococci, select Gram-negative microorganisms such as *Pseudomonas aureginosa, Acinetobacter baumannii, E. coli, Klebsiela pneumoniae, H. influenzae* and *M. catarrahlis*, as well as anaerobic microorganisms such as *bacteroides* and clostridia species, and acid-fast microorganisms such as *Mycobacterium tuberculosis* and *Mycobacterium avium*.

The in vitro activity of compounds provided herein may be assessed by standard testing procedures such as the determination of minimum inhibitory concentration (MIC) as described in *Approved Standard. Methods for Dilution Antimicrobial Susceptibility Tests for Bacteria that Grow Aerobically*, 3$^{rd}$ ed., 1993, published by the National Committee for Clinical Laboratory standards, Villanova, Pa., USA. Low MIC values indicate high antibacterial activity, while high MIC values reveal a reduced antibacterial activity (with higher drug concentration required for pathogen eradication in the latter instance). Generally, MIC values of about ≦4-8 µg/mL against a particular pathogen indicate a therapeutic (i.e. suitable for therapy) potency for antibacterial drugs, while MIC values of ≧16 µg/mL would reveal a lack of therapeutically useful activity for a test compound against this pathogen.

The useful in vitro activity (potency) of representative compounds provided herein against Gram-negative pathogens *Pseudomonas aeruginosa, Acinetobacter baumannii, Escherichia coli*, or *Klebsiela pneumoniae* is illustrated by the MIC data of Table 1 below.

As evident from the data of Table 1, representative compounds provided herein are highly active against Gram-negative pathogens. In particular, tricyclic compounds of Examples 1, 3, 4, and 7 possess a remarkably enhanced potency against *P. aeruginosa* (MICs of 2-4 µg/mL), with about 2-4-fold higher improvement in the activity against this pathogen over the bicyclic reference compound of Example 10 (MIC of 8 µg/mL). The tricyclic compounds provided herein display potency similar to that for the bicyclic reference compound of Example 25 of a generally related oxaborole class from the PCT WO 2008/157726. This reference compound is the first antibacterial investigational drug of the new class, as reported, for example, by Zane et al. in a poster *Safety, tolerability, and pharmacokinetics of a novel Gram-negative antimicrobial, GSK2251052, in healthy subjects*, 21st European Congress of Clinical Microbiology and Infectious Diseases, 2011, Milan, Italy.

TABLE 1

Antibacterial activity against Gram-negative pathogens in vitro.

| EXAMPLES | P. aeruginosa PAE 1001 mg/mL | E. coli ECO 1003 mg/mL | A. baumannii ABA 4001 mg/mL | K. pneumoniae KPN 4027 mg/mL |
|---|---|---|---|---|
| Reference Example 24[a] | 4 | 2 | 4 | 4 |
| Reference Example 23[a] | 32 | 64 | 64 | 64 |
| Reference Example 25[a] | 4 | 2 | 4 | 1 |
| Reference Example 10[a] | 8 | 4 | 8 | 4 |
| Example 1 | 4 | 4 | 4 | 4 |
| Example 3 | 2 | 2 | 4 | 2 |
| Example 4 | 4 | 4 | 4[b] | 2[c] |
| Example 7 | 4 | 8 | 4[b] | 4[c] |
| Example 11 | 16 | 16 | 16 | 8 |
| Example 12 | 16 | 8 | >32 | 8 |
| Example 13 | 8 | 8 | 16 | 8 |
| Example 14 | 8 | 4 | 16 | 4 |
| Example 15 | 64 | >64 | >64 | >64 |
| Example 16 | 32 | >32 | >32 | >32 |
| Example 17 | 8 | 2 | >32 | 2 |
| Example 18 | 32 | >32 | >32 | 32 |
| Example 19 | >32 | >32 | >32 | >32 |
| Example 20 | >32 | >32 | >32 | >32 |
| Reference Example 22[d] | >64 | 32 | 32 | 32 |

Notes:
[a]Reference compounds from the publication WO 2008/157726.
[b]Strain *A. baumannii* MABA0001.
[c]Strain *K. pneumoniae* KPN1004.
[d]Reference compound from the genus of the publication WO 2008/157726.

It is also remarkable that these tricyclic compounds generally related to the tricyclic compound of the reference compound of Example 24 possess similar or even improved antibacterial potency (MIC) vs. said compound, the sole prior tricyclic boron compound described in the PCT publication WO 2008/157726. For example, the compound of Example 3 exhibits 2-fold improved activity against representative strains of *P. aeruginosa, E. coli*, and *K. pneumoniae* as compared to the reference compound of Example 24 compound.

This is quite striking in face of the highly restrictive structure-activity relationships (SAR) within this class of tricyclic boron compounds.

The severe SAR limitation is illustrated by a dramatic drop in the antibacterial activity resulted from simple isosteric substitutions or minimal structural variations. While being generally acceptable for many classes of bioactive compounds (as reviewed, e.g., by Meanwell in *J. Med. Chem.*, 2011, vol. 54, pp. 2529-2591), these are generally disfavored within the class of compounds provided herein. For example, a minor one-carbon shift of the hydroxymethyl side chain in the compound of Example 7 to result in its isomeric compound of Example 11 leads to 4-fold reduced potency vs. *P. aeruginosa* and *A. baumannii* for the latter analog. Likewise, a minimal extension (homologation) of the hydroxymethyl side chain of compound of Example 7 to produce respective 2-hydroxyethyl compound of Example 12 leads to a 4-fold loss of activity vs. *P. aeruginosa*, and total loss of activity vs. *A. baumannii* for the latter compound (see Table 1). An introduction of a sole methyl group either into the hydroxymethyl side chain of the compound of Example 7 (to produce 1-hydroxyethyl compound of Example 14), or into the endocyclic CH group attached to same hydroxymethyl group (to produce the compound of Example 13) leads to about 4-fold loss of activity vs. *A. baumannii* for both compounds of Example 13 and Example 14, as compared to the compound of Example 7. Likewise, introduction of an extra hydroxymethyl group at same endocyclic CH of the Example 7 to produce bis-hydroxymethyl compound of Example 15 leads to nearly complete loss of antibacterial potency (see Table 1). In a striking contrast with established principles of bioisosterism, even simple replacement of a hydrogen atom in benzene ring of the structure of compound of Example 3 for fluorine leads to reduced activity in compounds of Example 17 and 18. This highly prohibitive SAR for tricyclic boron compounds may account for the fact that only the mono-substituted tricyclic compound (the reference compound of Example 24 herein) of this class was described in the PCT publication WO 2008/157726.

The restrictive SAR for the class of compounds provided herein is further summarized in the FIG. 1 below. As stated above, even minor structural modifications in the potent compounds (FIG. 1, top box structures) lead to a dramatic loss of the activity against *A. baumannii* in resulted closely related compounds (FIG. 1, lower box structures). This contrasts to isosteric modifications that are allowed by SAR for many other classes of bioactive agents (as reviewed by Meanwell in *J. Med. Chem.*, 2011, vol. 54, pp. 2529-2591) but disfavored for the class of tricyclic boron antibacterials provided herein.

Based on this SAR, one would expect only poor or no antibacterial potency for the tricyclic boron compounds of Examples 1, 3, 4, and 7. Thus, the antibacterial potency (MIC) data reveal the unique nature of the composition provided herein, such as compounds of Examples 1, 3, 4, and 7. The compounds provided herein are remarkably active, in face of the highly restrictive SAR that renders vast majority of other tricyclic boron compounds poorly active or entirely inactive, and thus unsuitable for therapy of Gram-negative infections in mammals.

Generally restrictive SAR for antibacterial boron compounds is further illustrated in Table 1 by a striking contrast of the potency data for the active reference compound of Example 25 vs. structurally close but essentially inactive reference compounds of Example 22 and Example 23 that incorporate two alcohol groups instead of one such group in the compound of Example 25. Aforementioned reference boron compounds incorporate a bicyclic rather than tricyclic oxaborole structure. Notably, both inactive compounds of Examples 22 and 23 would be generally related to theoretically feasible ring-opened bis-alcohol forms of compounds of Examples 1, 3, 4, and 7, which would be likewise expected to be inactive. Instead, the latter tricyclic compounds provided herein display a remarkably high activity against Gram-negative pathogens.

In addition to in vitro activity (potency determined as MIC), in vivo efficacy or ability to eradicate bacterial pathogens to the effect of survival of mammals under therapy is critical. It is well established that compounds with similar antibacterial potency in vitro (MIC) may display a dramatically different activity in vivo, resulting in a desired therapeutic effect for some efficacious compounds, or lack of any useful anti-infective effect for others, non-efficacious compounds. This critical for the actual therapy outcome is determined by multiple factors affecting the compound behavior in vivo, such as its absorption, distribution, metabolism, and excretion.

To establish the efficacy of the compounds provided herein in vivo, testing in a *P. aeruginosa* neutropenic mouse thigh infection model was performed with subcutaneous administration of test compounds analogously to the method described by Andes et al. in *Antimicrobial Agents and Chemotherapy*, 2002, 46(11), 3484-3489. In this model, a greater reduction in the bacterial colony-forming units (CFU) indicates more beneficial therapeutic effect (more bacterial eradication), while a lower CFU reduction indicates a lower effect (less bacterial eradication). The in vivo antibacterial effect is also referred to as efficacy, in contrast to the term potency commonly used for in vitro activity (expressed as MIC).

Remarkably, the compound of Example 3 displays a strikingly improved activity in the animal model of infection as compared to the tricyclic reference compound of Example 24 (with both agents administered at the identical dosing of 30 mg/kg). Thus, in the *P. aeruginosa* mouse thigh infection model, the compound of Example 3 has effected about 3.6 log (i.e., about 3981-fold) reduction in the bacterial colony-forming units (CFU), while in a side-by-side test the reference compound of Example 24 has caused only about 1.7 log (i.e., about 50-fold) CFU reduction in the bacterial infestation. Thus, the compound of Example 3 effectively causes about a dramatic over 80-fold higher degree of the desired pathogen reduction when compared to the reference compound of Example 24. This beneficial therapeutic effect is quite remarkable, since one might anticipate, at best, only a similar efficacy for these two compounds, based on generally similar in vitro activity against *P. aeruginosa* for both agents (as illustrated in Table 1 above).

Likewise, when compared to the bicyclic reference compound of Example 25 (the first investigational oxaborole antibacterial) in another *P. aeruginosa* mouse thigh infection model test, the tricyclic compound of Example 3 has effected about 3.44 log (i.e., about 2754-fold) reduction in the bacterial colony-forming units (CFU), while the reference compound of Example 25 has caused only about 2.37 log CFU reduction (i.e., about 234-fold reduction), in a side-by-side test and using identical 30 mg/kg dosing for both agents. Thus, the tricyclic boron compound of Example 3 is about 12-fold more efficient in the *P. aeruginosa* thigh infection model as compared to the reference boron compound of Example 25 described in the PCT publication WO 2008/157726.

This dramatic improvement of therapeutic activity in vivo (efficacy) for the compound of Example 3 is remarkable as no prior data directing one skilled in art to expect this beneficial effect exist anywhere. Additional related compounds provided herein display alike surprisingly improved in vivo efficacy. Thus, in the aforementioned animal infection model, the tricyclic compound of Example 1 has effected about 3.2 log (i.e., about 1584-fold) CFU reduction, while in a side-by-side test of the bicyclic reference compound of Example 10 has caused only about 1.3 log (about 20-fold) CFU reduction, revealing a dramatic 79-fold superiority in the bacterial reduction of the compound of Example 1 provided herein over generally related bicyclic boron compound of Example 10 described in the PCT publication WO 2008/157726.

To further elucidate therapeutic potential of drug compounds, pharmacokinetic (PK) data is used to establish the key parameters predictive of the therapy outcome, such as area under the curve (AUC) for a plot monitoring the change in the systemic drug concentration over time. Thus, a higher AUC value indicates a greater exposure to the drug, commonly associated with a greater therapeutic potential due to a higher amount of drug available to combat the infection in a mammal. In contrast, a lower AUC value indicates a reduced exposure to the drug under study, resulting in a reduced amount of antibiotic available to combat bacterial infestations. To that end, the compounds provided herein have been tested in the rat PK model of intravenous administration performed analogously to methods described in the monograph *Current Protocols in Pharmacology*, 2005, 7.1.1-7.1.26, John Wiley & Sons, Inc.

Quite remarkably, the pharmacokinetic data for the compound of Example 3 in a rat PK model of intravenous administration revealed a greatly improved systemic exposure for this compound over the comparator reference compound of Example 24, with the exposure (AUC) for the compounds of Example 3 and Example 24 determined as about 14100 and 5300 ng/mL*h, respectively, at identical dosing of 10 mg/kg. This remarkable result represents a striking 2.7-fold improvement in the exposure to the drug in vivo for the compound of Example 3 over the reference compound of Example 24 described in the PCT publication WO 2008/157726. This beneficial in vivo exposure effect is remarkable, since one skilled in art might anticipate, at best, only a similar exposure (AUC) for these two compounds, since both of these belong to a general class of tricyclic boron compounds (see structures in FIG. 1 above).

Likewise, the in vivo exposure for this tricyclic compound of Example 3 is greatly improved when compared to in vivo exposure for the bicyclic compound of Example 25 (the investigational oxaborole drug comparator): with AUC values of about 14100 and 6241 ng/mL*h, respectively, representing a dramatic—over 2-fold—improvement for the compound of Example 3 achieved at the identical with the reference compound of Example 25 dosing of 10 mg/kg.

This dramatic improvement of in vivo exposure (AUC) for the compound of Example 3 is remarkable, as no prior data directing one skilled in art to expect this beneficial effect exist anywhere. Additional related compounds provided herein also display alike remarkably improved in vivo exposure. Thus, pharmacokinetic data for the compound of Example 1 in a rat model of intravenous administration reveal a greatly improved systemic exposure for this compound over the comparator reference compound of Example 10, with the AUC for the compounds of Example 1 and Example 10 determined as about 11520 and 5367 ng/mL*h, respectively. This result represents more than 2-fold improvement in the exposure for the tricyclic compound of Example 1 as compared to the bicyclic reference compound of Example 10 described in the PCT publication WO 2008/157726.

In summary, above support data illustrate that the compounds provided herein (such as compounds of Examples 1, 3, 4, and 7) possess a remarkably high or improved in vitro antibacterial potency against key Gram-negative pathogens (such as *A. baumannii* and *P. aeruginosa*), contrasting a severely restricted SAR that would not lead one skilled in art to anticipate such activity. In addition, the compounds provided herein also exhibit a dramatic in vivo activity (efficacy) improvement in animal models of infection (such as *P. aeruginosa* thigh infection model). Finally, select compounds provided herein exhibit beneficial enhancement in the systemic exposure (as demonstrated in the intravenous pharmacokinetics rat model).

Above representative data taken in its entirety reveal a remarkably superior therapeutic potential for the compounds provided herein (such as the compounds of Example 1, 3, 4, and 7), with the beneficial advantages in areas of potency, efficacy, and exposure compared to other boron anti-infectives, including that of the PCT publication WO 2008/157726. The dramatic improvement in three distinctly different critical parameters for antibacterial compounds provided herein (such as compounds of Examples 1, 3, 4, and 7) offers marked potential benefits for human or mammal therapy, including but not limited to shorter therapy duration, a reduced effective drug dose, reduced possible adverse effects, and/or more convenient dosing regimen.

Administration and Pharmaceutical Formulations

In general, the compounds provided herein will be administered in a therapeutically effective amount by any of the accepted modes of administration for agents that serve similar utilities. By way of example, the compounds provided herein may be administered orally, parenterally, transdermally, topically, rectally, or intranasally. The actual amount of the compound provided herein, i.e., the active ingredient, will depend on a number of factors, such as the severity of the disease, i.e., the infection, to be treated, the age and relative health of the subject, the potency of the compound used, the route and form of administration, and other factors, all of which are within the purview of the attending clinician.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method provided herein, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

When employed as pharmaceuticals, the compounds provided herein are usually administered in the form of pharmaceutical compositions. These compounds can be administered by a variety of routes including oral, parenteral, transdermal, topical, rectal, and intranasal.

These compounds are effective as both injectable and oral compositions. Such compositions are prepared in a manner well known in the pharmaceutical art and comprise at least one active compound.

Also provided herein are pharmaceutical compositions which contain, as the active ingredient, one or more of the compounds provided herein above associated with pharmaceutically acceptable carriers. In making the compositions provided herein, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

The quantity of an active component, that is the compound provided herein, in the pharmaceutical composition and unit dosage form thereof may be varied or adjusted widely depending upon the particular application, the potency of the particular compound and the desired concentration.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound provided herein above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It, will be understood, however, that the amount of the compound actually administered will be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound provided herein. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient provided herein.

The tablets or pills provided herein may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions provided herein may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, preferably orally or nasally, from devices that deliver the formulation in an appropriate manner.

Another preferred formulation employed in the methods provided herein employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions that can transiently open the blood-brain barrier.

Other suitable formulations can be found in *Remington's Pharmaceutical Sciences*, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

What is claimed is:

1. A compound of the following formula I

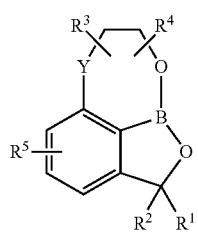

I or a pharmaceutically acceptable salt, complex, or tautomer thereof, wherein:
R$^1$ and R$^2$ are independently H, F, C$_{1-6}$alkyl, C$_{1-6}$(amino)alkyl, aminomethyl, or C$_{1-6}$alkylNH$_2$;
and wherein
R$^3$ and R$^4$ are independently a single substituent or multiple substituents independently selected from H, halo, CN, C$_{1-6}$alkyl, C$_{1-6}$(hydroxy)alkyl, C$_{1-6}$alkylamino, C$_{1-6}$alkoxy, C$_{1-6}$heteroalkyl, C$_{1-6}$haloalkyl, or C$_{1-6}$(amino)alkyl; and wherein
Y is O, S, CH$_2$, CHF, or CF$_2$; and wherein
R$^5$ is H, halo, CN, OH, or NH$_2$.

2. The compound of formula I of claim 1 and with a proviso that when R$^1$, R$^3$, R$^4$, R$^5$ are all H; and wherein R$^2$ is CH$_2$NH$_2$; then Y is other than O.

3. The compound of claim 2 wherein R$^1$ is H; and wherein the chiral group CR$^1$R$^2$ has (S)-configuration.

4. The compound of claim 1 wherein R$^1$, R$^3$, and R$^5$ are all H; R$^2$ is CH$_2$NH$_2$, and R$^4$ is CH$_2$OH group attached to the carbon atom of the ring fragment CH—O—B.

5. The compound of claim 4 wherein the chiral group CHR$^4$ has (R)-configuration.

6. The compound of claim 1 selected from the group consisting of

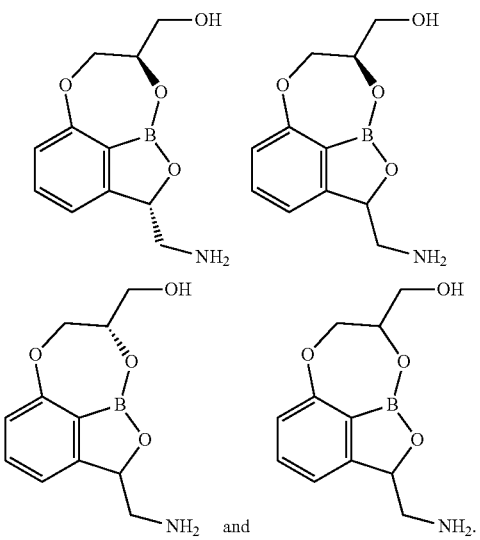

7. The compound of claim 1 selected from the group consisting of

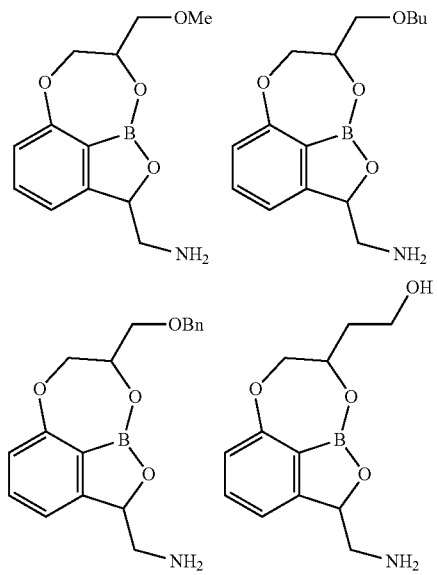

-continued

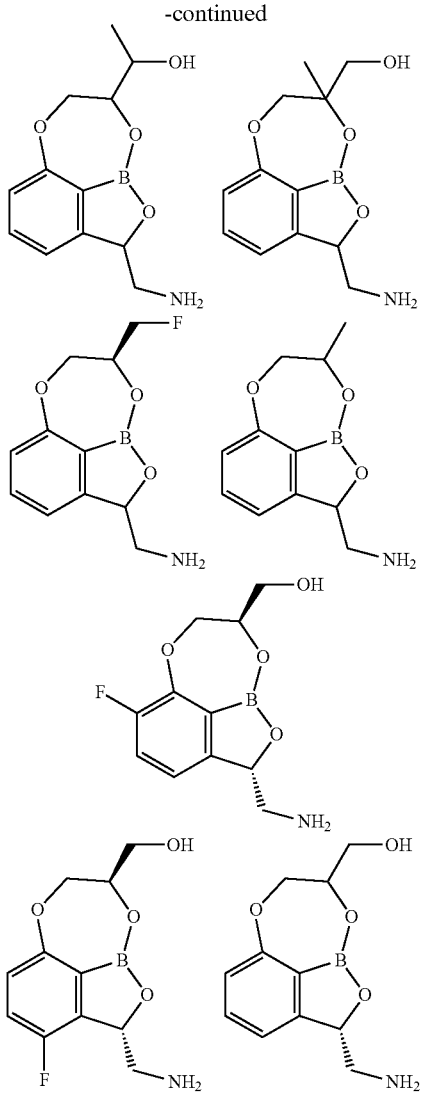

-continued

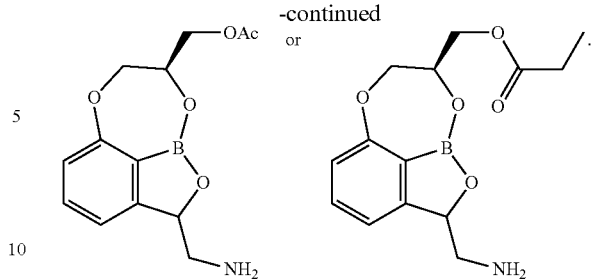

8. A method for arresting or reducing the development of a microbial infection in a mammal comprising administering to the mammal a therapeutically effective amount of a compound of claim 1.

9. The method according to claim 8, wherein the compound is administered to the mammal orally, parenterally, transdermally, topically, rectally, or intranasally in a pharmaceutical composition.

10. A method according to claim 8 wherein the microbial infection is a Gram-negative, Gram-positive, or mycobacterial infection.

11. A method according to claim 8 wherein the microbial infection is caused by microorganisms selected from *Pseudomonas aeruginosa*, *Acinetobacter baumannii*, *Escherichia coli*, or *Klebsiela pneumoniae*.

12. The method according to claim 8, wherein the infection is a skin, soft tissue, respiratory, or an eye infection.

13. The compound of claim 1 with a minimum inhibitory concentration against microorganisms *Pseudomonas aeruginosa* and *Acinetobacter baumannii* of less or equal to 4 µg/mL.

14. A pharmaceutical composition comprising a therapeutically effective amount of a compound of claim 1 and a pharmaceutically acceptable carrier.

* * * * *